US011018308B2

United States Patent
Obana et al.

(10) Patent No.: US 11,018,308 B2
(45) Date of Patent: *May 25, 2021

(54) PHOTOELECTRIC CONVERSION FILM, PHOTOELECTRIC CONVERSION ELEMENT AND ELECTRONIC DEVICE

(71) Applicant: SONY SEMICONDUCTOR SOLUTIONS CORPORATION, Kanagawa (JP)

(72) Inventors: Yoshiaki Obana, Kanagawa (JP); Yuki Negishi, Kanagawa (JP); Yuta Hasegawa, Kanagawa (JP); Ichiro Takemura, Kanagawa (JP); Osamu Enoki, Kanagawa (JP); Hideaki Mogi, Kanagawa (JP); Nobuyuki Matsuzawa, Tokyo (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/687,275

(22) Filed: Nov. 18, 2019

(65) Prior Publication Data

US 2020/0161566 A1 May 21, 2020

Related U.S. Application Data

(63) Continuation of application No. 15/308,174, filed as application No. PCT/JP2015/001986 on Apr. 8, 2015, now Pat. No. 10,672,994.

(30) Foreign Application Priority Data

May 13, 2014 (JP) .................................. 2014-099816
Jan. 6, 2015 (JP) .................................. 2015-000695

(51) Int. Cl.
| | |
|---|---|
| H01L 51/00 | (2006.01) |
| H01L 51/42 | (2006.01) |
| H01L 27/30 | (2006.01) |
| C09B 47/00 | (2006.01) |
| C09B 48/00 | (2006.01) |
| C09B 67/22 | (2006.01) |
| C07D 471/04 | (2006.01) |
| C07F 5/02 | (2006.01) |

(52) U.S. Cl.
CPC ........ *H01L 51/0078* (2013.01); *C07D 471/04* (2013.01); *C07F 5/022* (2013.01); *C09B 47/00* (2013.01); *C09B 48/00* (2013.01); *C09B 67/0033* (2013.01); *H01L 27/307* (2013.01); *H01L 51/0067* (2013.01); *H01L 51/0072* (2013.01); *H01L 51/4246* (2013.01); *H01L 27/30* (2013.01); *H01L 51/424* (2013.01); *Y02E 10/549* (2013.01)

(58) Field of Classification Search
CPC ......... H01L 27/22; H01L 43/02; H01L 43/10; H01L 43/12
See application file for complete search history.

(56) References Cited

U.S. PATENT DOCUMENTS

| | | | |
|---|---|---|---|
| 10,312,457 B2 * | 6/2019 | Obana | ................ H01L 51/0072 |
| 10,672,994 B2 * | 6/2020 | Obana | .................... C09B 48/00 |
| 2014/0097416 A1 * | 4/2014 | Lee | .................... H01L 51/0069 |
| | | | 257/40 |

\* cited by examiner

*Primary Examiner* — Mark W Tornow
(74) *Attorney, Agent, or Firm* — Sheridan Ross P.C.

(57) ABSTRACT

There is provided a photoelectric conversion film including a quinacridone derivative represented by the following General formula and a subphthalocyanine derivative represented by the following General formula.

41 Claims, 12 Drawing Sheets

(A)

(B)

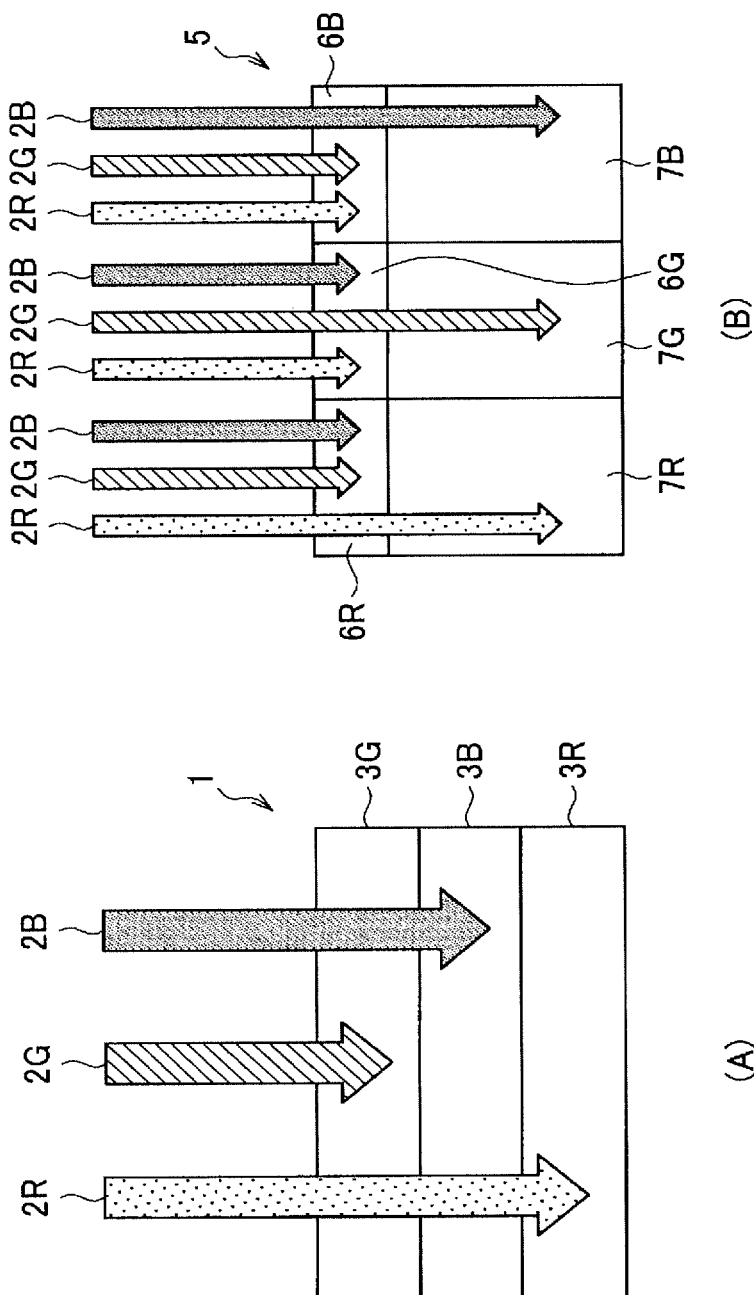
[FIG. 1]

[Fig. 2]
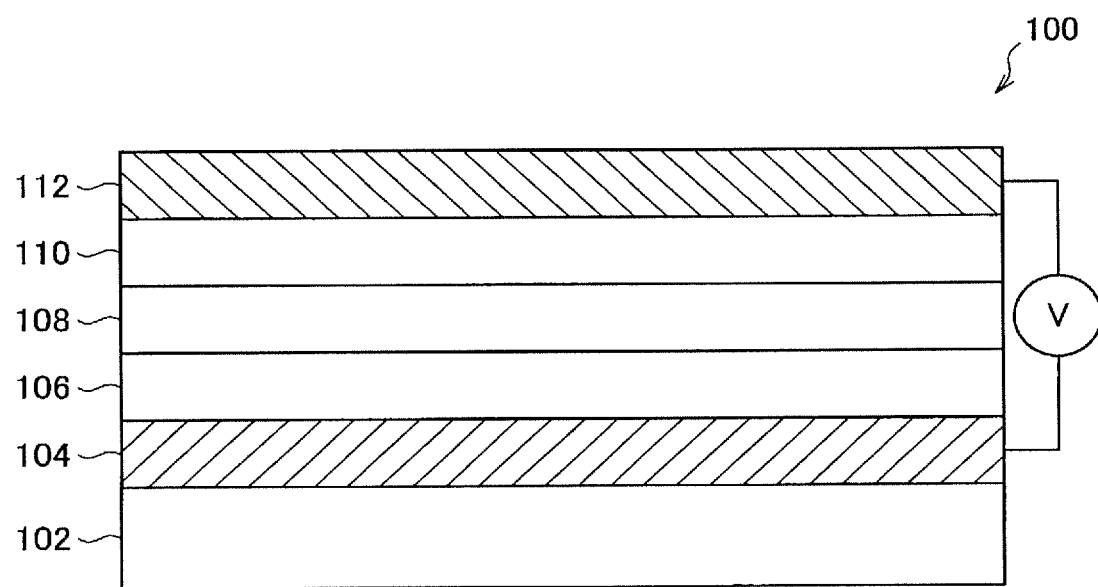

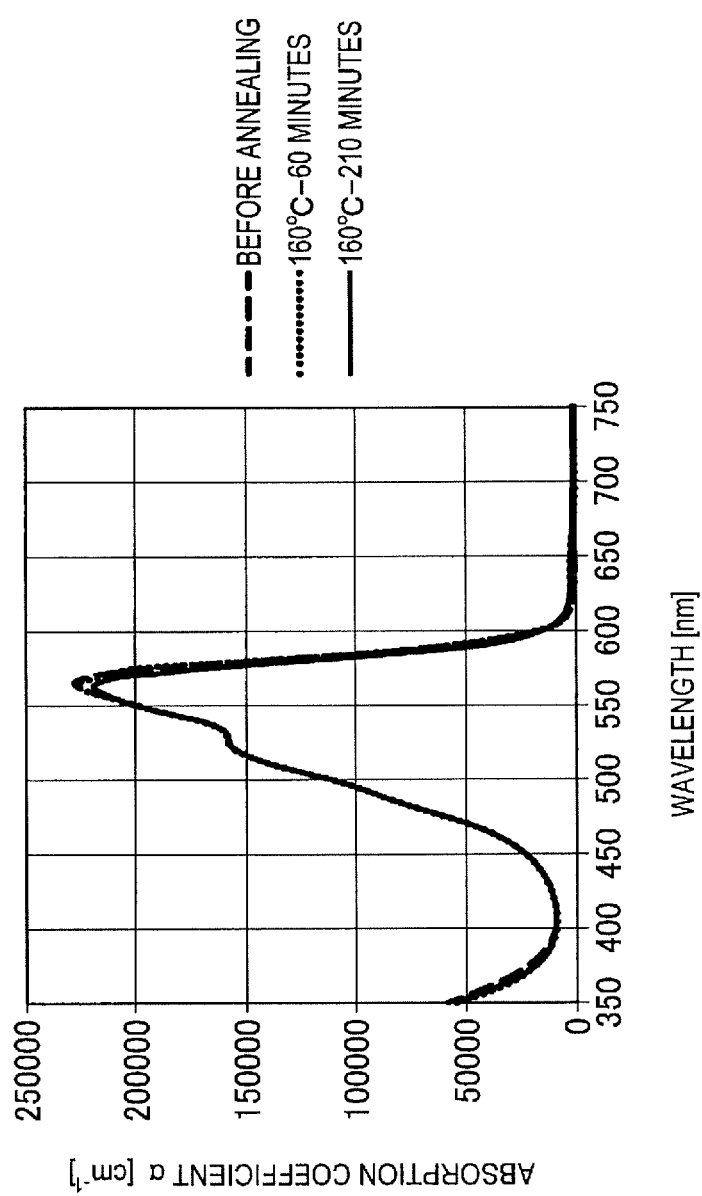
[FIG. 3A]

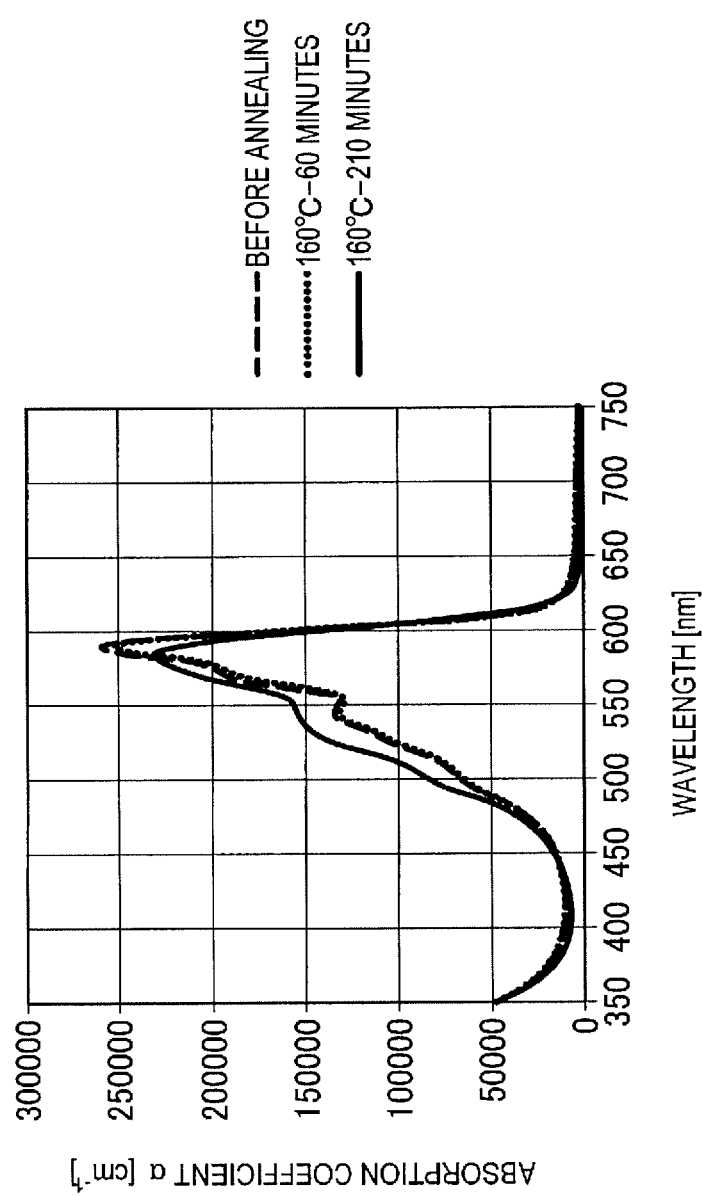
[FIG. 3B]

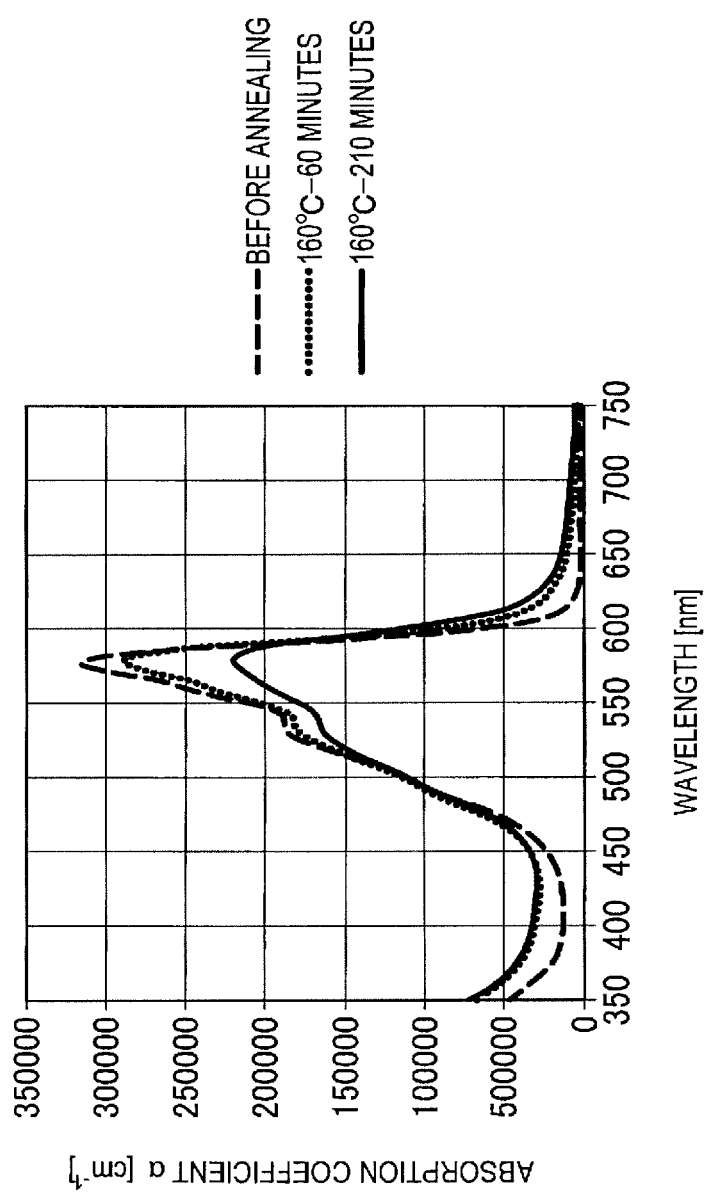
[FIG. 3C]

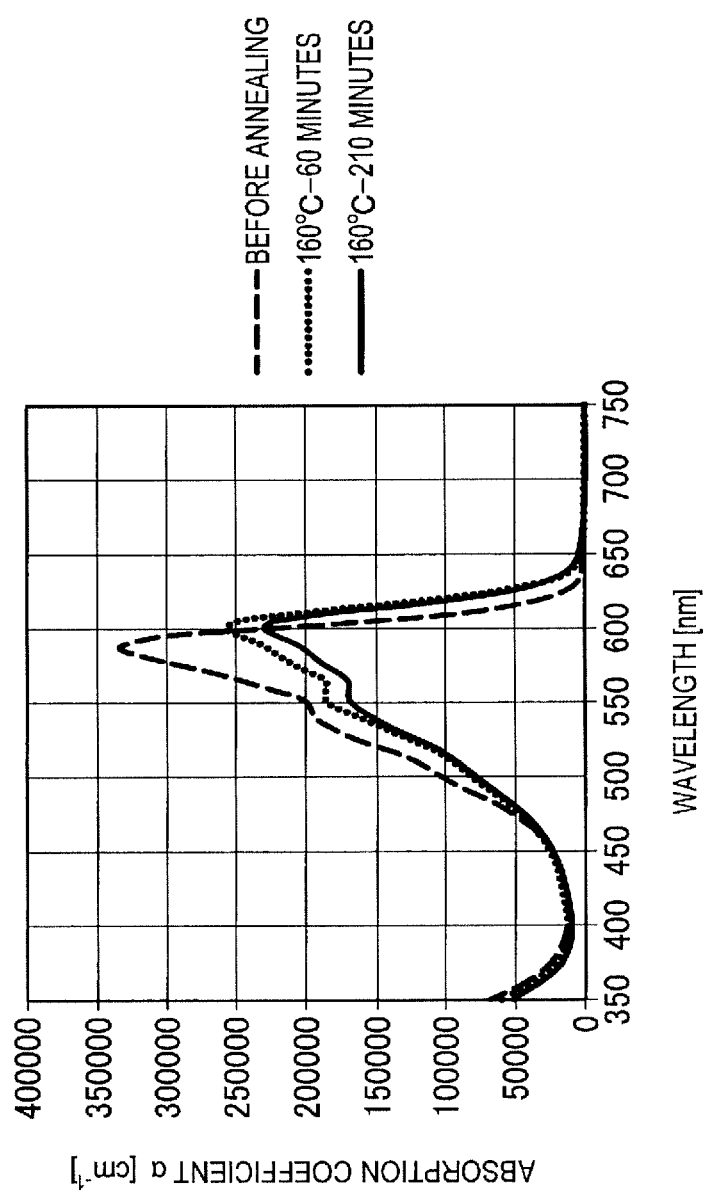
[FIG. 3D]

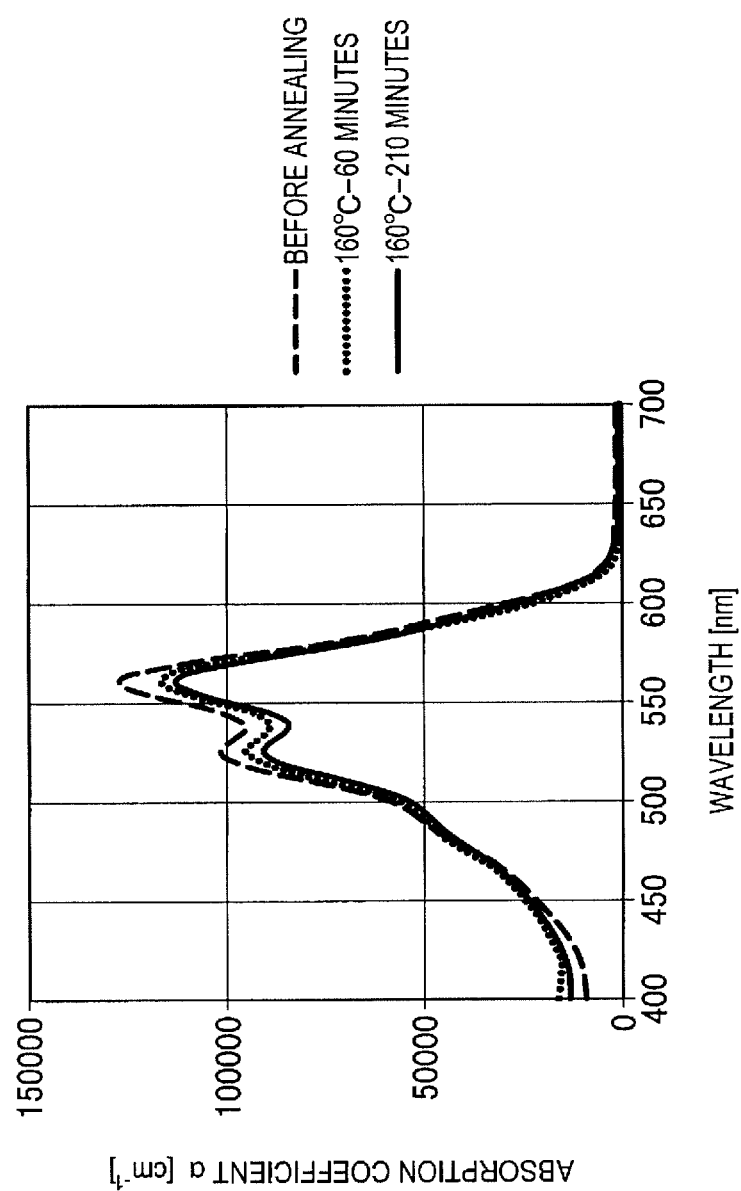
[FIG. 3E]

[Fig. 4]
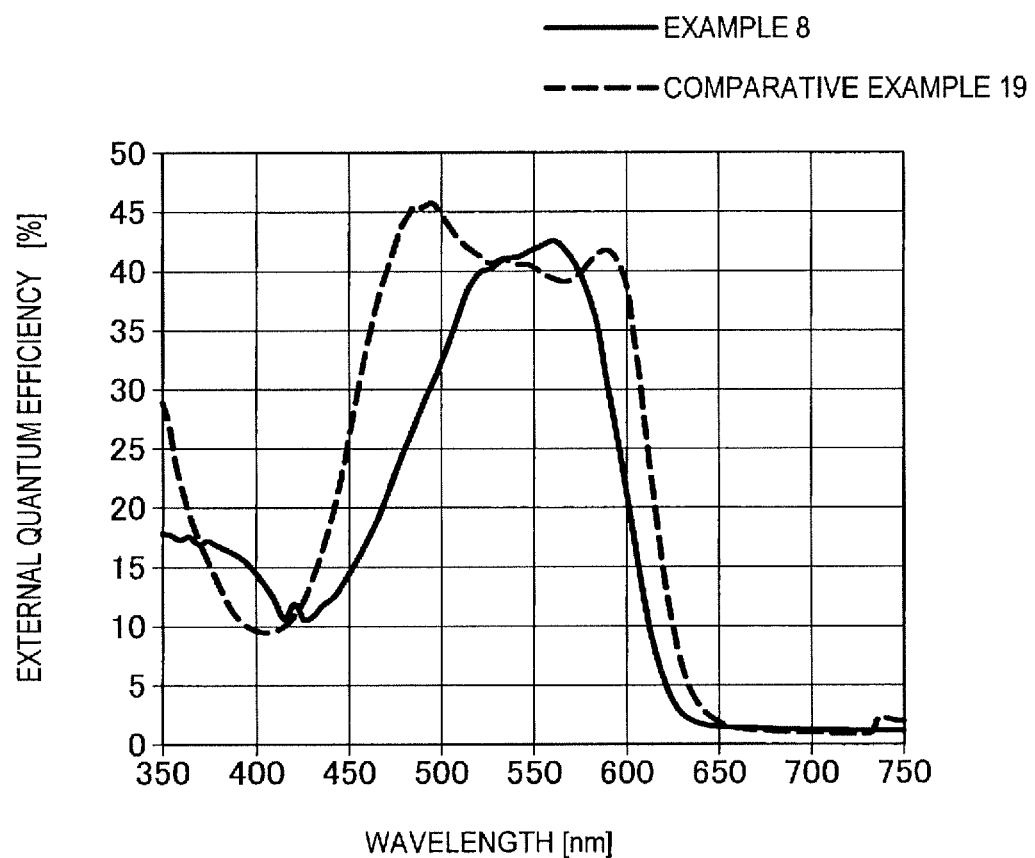

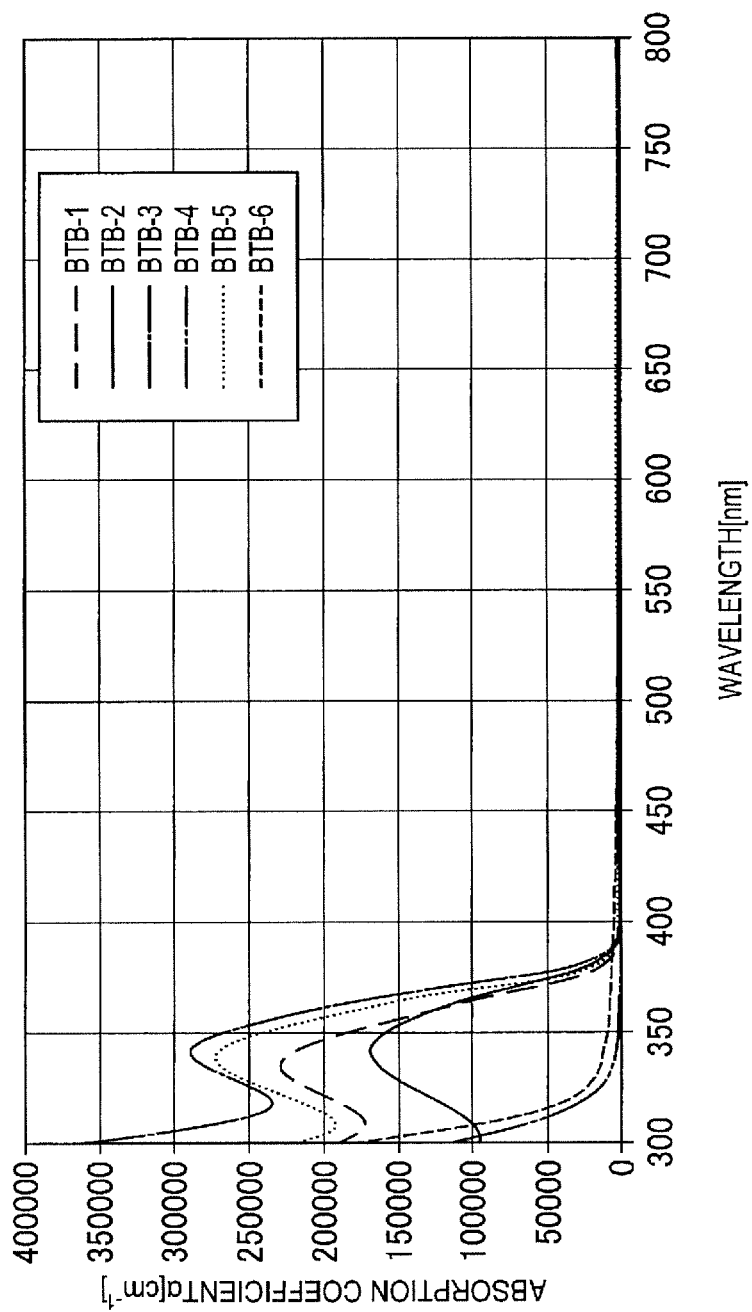
[FIG. 5]

FIG. 6
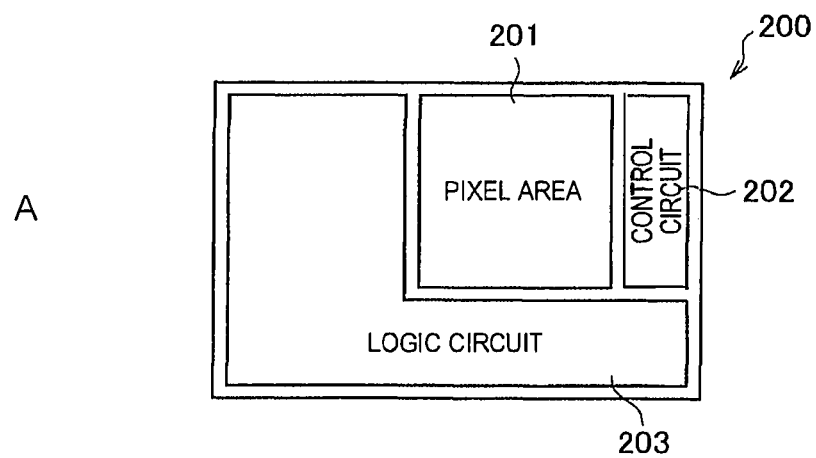
A
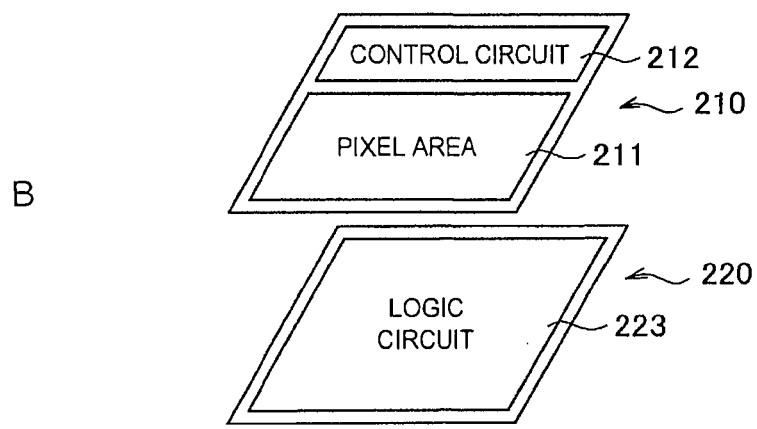
B
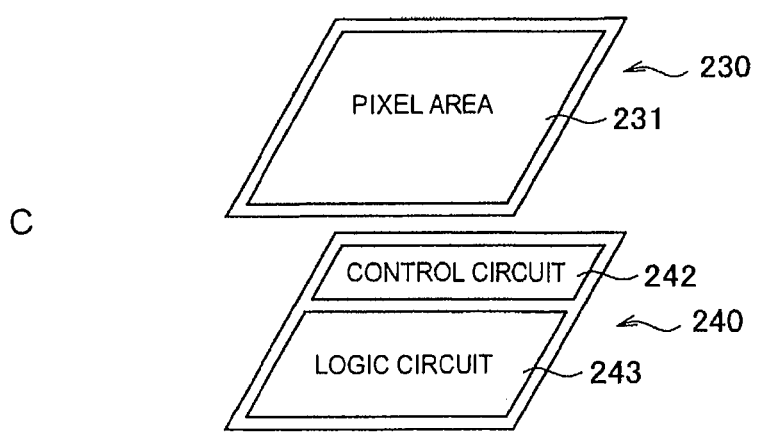
C

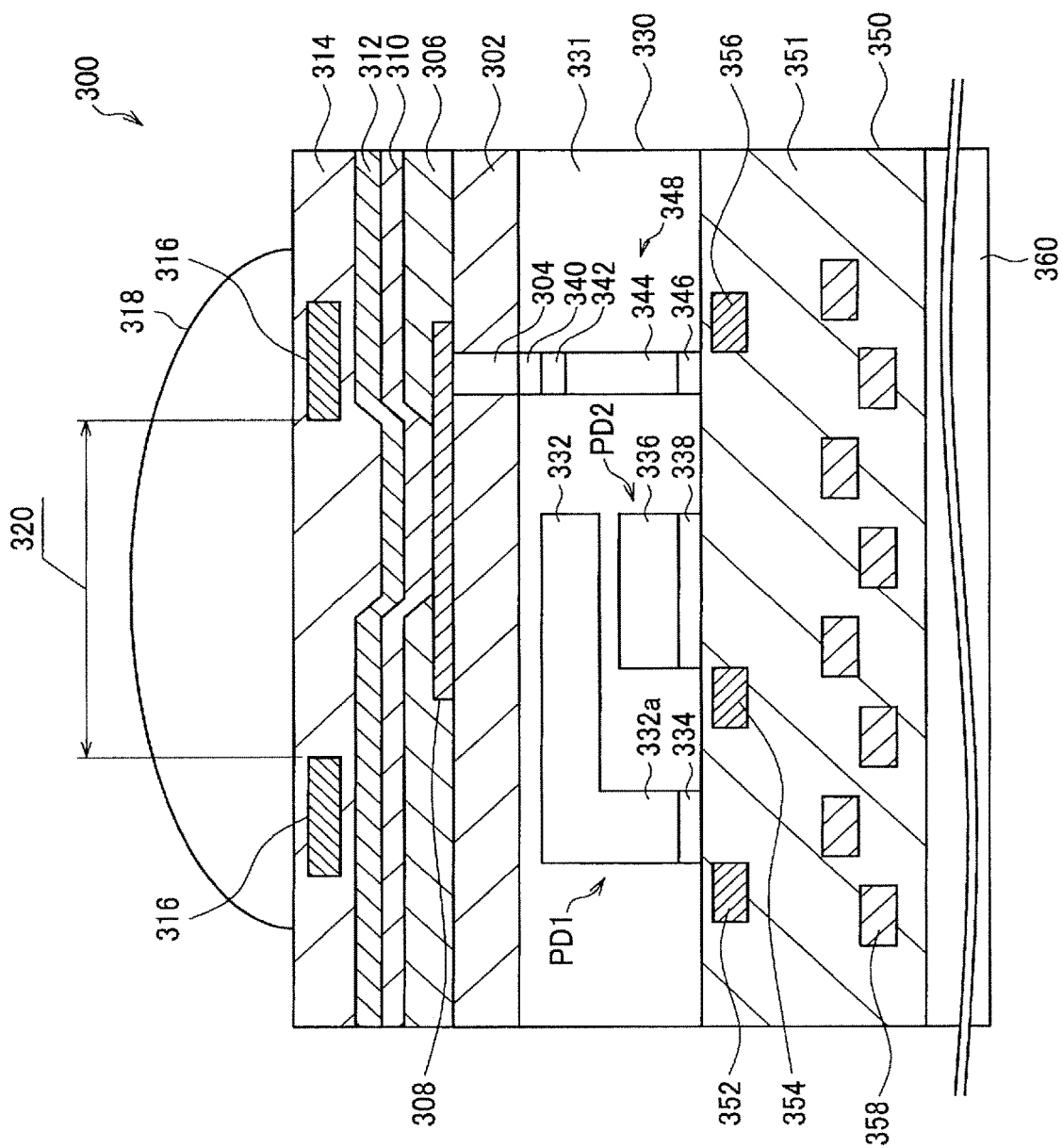
[FIG. 7]

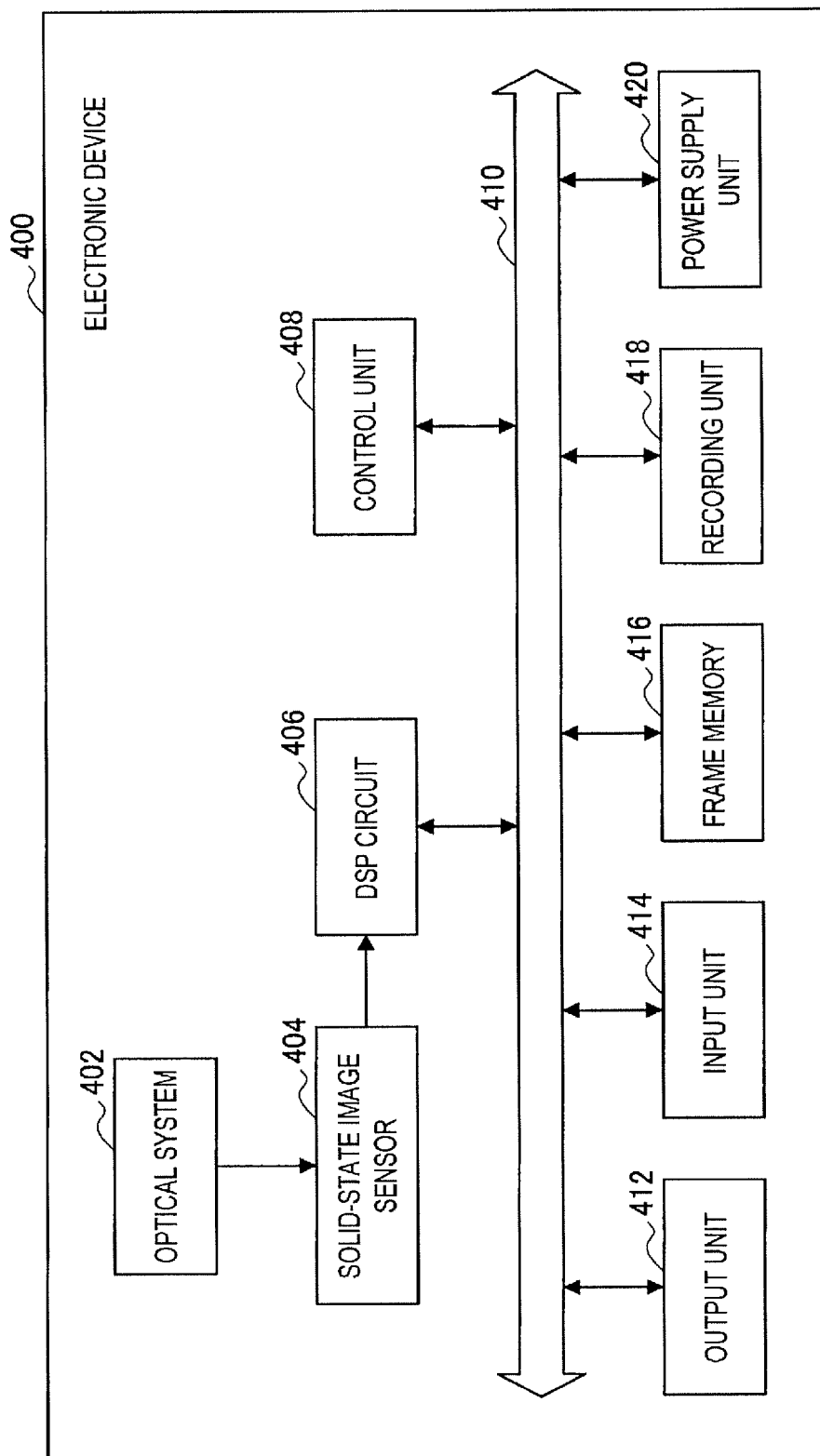
[FIG. 8]

PHOTOELECTRIC CONVERSION FILM, PHOTOELECTRIC CONVERSION ELEMENT AND ELECTRONIC DEVICE

CROSS REFERENCE TO RELATED APPLICATIONS

This application is a continuation of U.S. patent application Ser. No. 15/308,174, filed Nov. 1, 2016, which is a nation stage application under 35 U.S.C. 371 and claims the benefit of PCT Application No. PCT/JP2015/001986 having an international filing date of 8 Apr. 2015, which designated the United States, which PCT application claimed the benefit of Japanese Priority Patent Application JP2014-099816 filed May 13, 2014, and Japanese Priority Patent Application JP2015-000695 filed Jan. 6, 2015, the entire contents of each of which are incorporated herein by reference.

TECHNICAL FIELD

The present disclosure relates to a photoelectric conversion film, a photoelectric conversion element and an electronic device.

BACKGROUND ART

Recently, a solid-state image sensor having a multilayer structure in which photoelectric conversion films made of an organic material are laminated has been proposed.

For example, Patent Literature 1 discloses a solid-state image sensor in which organic photoelectric conversion films for absorbing each of blue light, green light and red light are sequentially laminated. In the solid-state image sensor disclosed in Patent Literature 1, a signal of each color is extracted by performing photoelectric conversion on light corresponding to that color in each of the organic photoelectric conversion films.

In addition, Patent Literature 2 discloses a solid-state image sensor in which an organic photoelectric conversion film for absorbing green light and a silicon photodiode are sequentially laminated. In the solid-state image sensor disclosed in Patent Literature 2, a signal of green light is extracted by an organic photoelectric conversion film, and signals of blue light and red light that are separated using a difference of a light penetration depth by the silicon photodiode are extracted.

Meanwhile, in the field of solar cells, in order to implement high photoelectric conversion efficiency, technology in which two types of organic materials are mixed such that at least one material becomes crystal fine particles and a photoelectric conversion film is formed as a bulk hetero mixed film is proposed. Specifically, as disclosed in Patent Literature 3, technology in which a p type photoelectric conversion material and an n type photoelectric conversion material are codeposited so that a photoelectric conversion film is formed as a bulk hetero mixed film is proposed.

CITATION LIST

Patent Literature

PTL 1: JP 2003-234460A
PTL 2: JP 2005-303266A
PTL 3: JP 2002-76391A

SUMMARY

Technical Problem

Here, since spectral characteristics of a photoelectric conversion film formed as a bulk hetero mixed film by two types of organic materials are influenced by spectral characteristics of the two types of mixed organic materials, a wavelength band of light to be absorbed is likely to be wider. Therefore, in the photoelectric conversion film formed as a bulk hetero mixed film, it is difficult to selectively absorb light of a specific wavelength range and it is difficult to have appropriate spectral characteristics as the photoelectric conversion film of a solid-state image sensor. Accordingly, it is difficult to increase sensitivity of such a solid-state image sensor using an organic photoelectric conversion film.

In view of the above-described problems, the present disclosure provides a new and improved photoelectric conversion film capable of increasing sensitivity of a solid-state image sensor, a solid-state image sensor including the photoelectric conversion film, and an electronic device including the solid-state image sensor.

Solution to Problem

According to an embodiment of the present disclosure, there is provided a photoelectric conversion film including a quinacridone derivative represented by General formula (1), and a subphthalocyanine derivative represented by General formula (2).

[Chem.1]

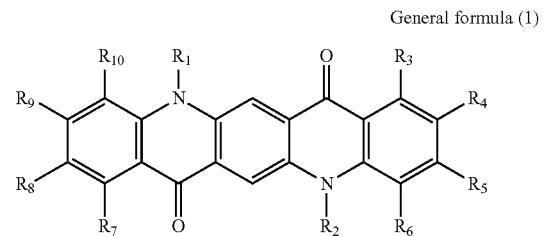

General formula (1)

In General formula (1), $R_1$ to $R_{10}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the $R_1$ to $R_{10}$ that are adjacent to one another.

[Chem.2]

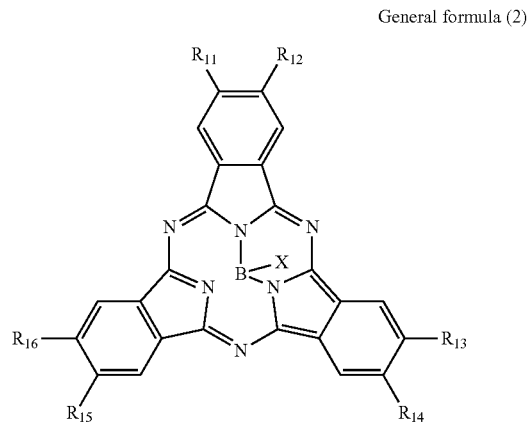

General formula (2)

In General formula (2), $R_{11}$ to $R_{16}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, where X is selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group, and where at least one of $R_{11}$ to $R_{16}$ represents fluorine.

According to another embodiment of the present disclosure, there is provided a photoelectric conversion film including a transparent compound that does not absorb visible light and that is represented by at least one of the following General formula (3) and General formula (4).

[Chem.3]

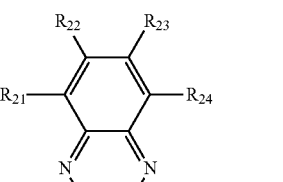

General formula (3)

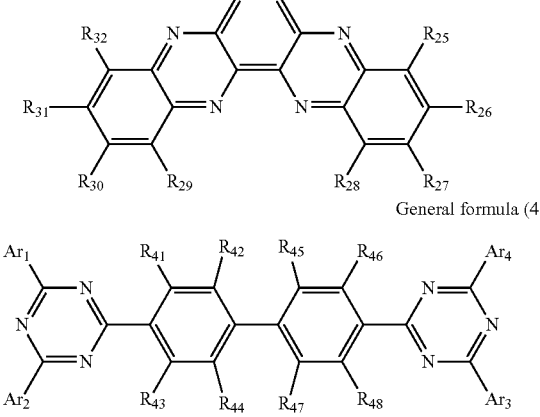

General formula (4)

In General formula (3), $R_{21}$ to $R_{32}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the $R_{21}$ to $R_{32}$ that are adjacent to one another.

In General formula (4), $R_{41}$ to $R_{48}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, an imide group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the $R_{41}$ to $R_{48}$ that are adjacent to one another, and where $Ar_1$ to $Ar_4$ are each independently one of a substituted or unsubstituted aryl group and a substituted or unsubstituted heteroaryl group.

In addition, according to another embodiment of the present disclosure, there is provided a photoelectric conversion element that includes a photoelectric conversion film; a pair of electrodes that are disposed at both sides of the photoelectric conversion film, which is interposed therebetween; and a hole blocking layer disposed between the photoelectric conversion film and one of the electrodes, where a difference between an ionization potential of the hole blocking layer and a work function of the one of the electrodes is greater than or equal to 2.3 eV.

According to another embodiment of the present disclosure, since the photoelectric conversion film can selectively absorb light of a specific wavelength band, it is possible to obtain appropriate spectral characteristics for the solid-state image sensor.

Advantageous Effects of Invention

As described above, according to one or more embodiments of the present disclosure, there are provided a photoelectric conversion film capable of increasing sensitivity of a solid-state image sensor, a solid-state image sensor including the photoelectric conversion film and an electronic device including the solid-state image sensor.

Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1 shows explanatory diagrams illustrating a solid-state image sensor (A) including a photoelectric conversion element according to an embodiment of the present disclosure and a solid-state image sensor (B) according to a comparative example.

FIG. 2 is a schematic diagram illustrating an exemplary photoelectric conversion element according to an embodiment of the present disclosure.

FIG. 3A shows the graph of evaluation results of a change in spectral characteristics of Example 4.

FIG. 3B shows the graph of evaluation results of a change in spectral characteristics of Comparative example 7.

FIG. 3C shows the graph of evaluation results of a change in spectral characteristics of Comparative example 8.

FIG. 3D shows the graph of evaluation results of a change in spectral characteristics of Comparative example 9.

FIG. 3E shows the graph of evaluation results of a change in spectral characteristics of a reference example.

FIG. 4 shows the graph of IPCE measurement results of Example 8 and Comparative example 19.

FIG. 5 shows the graph of spectral characteristics of BTB compounds.

FIG. 6 shows schematic diagrams illustrating a structure of a solid-state image sensor to which a photoelectric conversion element according to an embodiment of the present disclosure is applied.

FIG. 7 is a cross sectional view illustrating an outline in a unit pixel of a solid-state image sensor to which a photoelectric conversion element according to an embodiment of the present disclosure is applied.

FIG. 8 is a block diagram illustrating a configuration of an electronic device to which a photoelectric conversion element according to an embodiment of the present disclosure is applied.

DESCRIPTION OF EMBODIMENTS

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, description will be provided in the following order.

1. Outline of photoelectric conversion element according to an embodiment of the present disclosure
2. First embodiment
2.1. Configuration of photoelectric conversion film according to first embodiment
2.2. Configuration of photoelectric conversion element according to first embodiment
2.3. Example according to first embodiment
3. Second embodiment
3.1. Configuration of photoelectric conversion film according to second embodiment
3.2. Configuration of photoelectric conversion element according to second embodiment
3.3. Example according to second embodiment
4. Third embodiment
4.1. Configuration of photoelectric conversion element according to third embodiment
4.2 Example according to third embodiment
5. Application example of photoelectric conversion element according to an embodiment of the present disclosure
5.1. Configuration of solid-state image sensor
5.2. Configuration of electronic device
6. Summary 1. Outline of Photoelectric Conversion Element According to an Embodiment of the Present Disclosure An outline of a photoelectric conversion element according to an embodiment of the present disclosure will be described with reference to FIG. 1. (A) of FIG. 1 is an explanatory diagram illustrating a solid-state image sensor including a photoelectric conversion element according to an embodiment of the present disclosure. (B) of FIG. 1 is an explanatory diagram illustrating a solid-state image sensor according to a comparative example.

Hereinafter, in this specification, when it is described that "light of a certain wavelength is absorbed," it means that about 70% or more of light of the wavelength is absorbed. In addition, in contrast, when it is described that "light of a certain wavelength is transmitted" or "light of a certain wavelength is not absorbed," it means that about 70% or more of light of the wavelength is transmitted and about 30% or less of the light is absorbed.

First, a solid-state image sensor according to a comparative example will be described. As illustrated in (B) of FIG. 1, a solid-state image sensor 5 according to a comparative example includes photodiodes 7R, 7G and 7B, and color filters 6R, 6G and 6B formed on the photodiodes 7R, 7G and 7B.

The color filters 6R, 6G and 6B are films that selectively transmit light of a specific wavelength. For example, the color filter 6R is a film that selectively transmits red light 2R of a wavelength of greater than or equal to 600 nm. The color filter 6G is a film that selectively transmits green light 2G of a wavelength of greater than or equal to 450 nm and less than 600 nm. The color filter 6B is a film that selectively transmits blue light 2B of a wavelength of greater than or equal to 400 nm and less than 450 nm.

In addition, the photodiodes 7R, 7G and 7B are photodetectors for absorbing light of a wide wavelength band (for example, an absorption wavelength of a silicon photodiode is 190 nm to 1100 nm). For this reason, when each of the photodiodes 7R, 7G and 7B is used, it was difficult to individually extract a signal of each color such as red, green and blue. Therefore, in the solid-state image sensor according to the comparative example, light other than light corresponding to each color is absorbed by the color filters 6R, 6G and 6B, only light corresponding to each color is selectively transmitted to separate colors, and a signal of each color is extracted by the photodiodes 7R, 7G and 7B.

Accordingly, in the solid-state image sensor 5 according to the comparative example, since most light is absorbed by the color filters 6R, 6G and 6B, the photodiodes 7R, 7G and 7B may substantially use only ⅓ of incident light for photoelectric conversion. Therefore, in the solid-state image sensor 5 according to the comparative example, it was difficult to increase detection sensitivity of each color.

Next, a solid-state image sensor 1 including a photoelectric conversion element according to an embodiment of the present disclosure will be described. As illustrated in (A) of FIG. 1, the solid-state image sensor 1 including the photoelectric conversion element according to an embodiment of the present disclosure has a configuration in which a green photoelectric conversion element 3G configured to absorb the green light 2G, a blue photoelectric conversion element 3B configured to absorb the blue light 2B and a red photoelectric conversion element 3R configured to absorb the red light 2R are sequentially laminated.

For example, the green photoelectric conversion element 3G is an organic photoelectric conversion element that selectively absorbs green light having a wavelength of greater than or equal to 450 nm and less than 600 nm. The blue photoelectric conversion element 3B is an organic photoelectric conversion element that selectively absorbs blue light having a wavelength of greater than or equal to 400 nm and less than 450 nm. The red photoelectric conversion element 3R is an organic photoelectric conversion element that selectively absorbs red light having a wavelength of greater than or equal to 600 nm.

Accordingly, in the solid-state image sensor 1 according to an embodiment of the present disclosure, each of the photoelectric conversion elements can selectively absorb light of a specific wavelength band corresponding to red, green or blue. For this reason, in the solid-state image sensor 1 according to an embodiment of the present disclosure, there is no need to provide a color filter for separating incident light into each color, and all incident light can be used for photoelectric conversion. Therefore, since the solid-state image sensor 1 according to an embodiment of the present disclosure can increase light that can be used for photoelectric conversion to about three times that of the solid-state image sensor 5 according to the comparative example, it is possible to further increase detection sensitivity of each color.

Also, in the solid-state image sensor 1 according to an embodiment of the present disclosure, the blue photoelectric conversion element 3B and the red photoelectric conversion element 3R may be a silicon photodiode that performs photoelectric conversion on light of a wide wavelength band (specifically, such as 190 nm to 1100 nm). In this case, the blue photoelectric conversion element 3B and the red photoelectric conversion element 3R separate colors into the blue light 2B and the red light 2R using a difference of a penetration depth of light of each wavelength with respect to the solid-state image sensor 1. Specifically, since the red light 2R has a longer wavelength and is less easily scattered than the blue light 2B, the red light 2R penetrates to a depth separated from a surface of incidence. On the other hand, since the blue light 2B has a shorter wavelength and is more easily scattered than the red light 2R, the blue light 2B penetrates only to a depth close to the surface of incidence. Accordingly, when the red photoelectric conversion element 3R is disposed at a position away from the surface of incidence of the solid-state image sensor 1, it is possible to separately detect the red light 2R from the blue light 2B. Accordingly, even when the silicon photodiode is used as the blue photoelectric conversion element 3B and the red photoelectric conversion element 3R, the blue light 2B and the red light 2R can be separated using a difference of a penetration depth of light and a signal of each color can be extracted.

Accordingly, in the photoelectric conversion elements 3G, 3B and 3R included in the solid-state image sensor 1 according to an embodiment of the present disclosure, it is necessary to selectively absorb light of a specific wavelength band corresponding to red, green or blue and transmit light of a wavelength other than an absorption wavelength. In particular, the green photoelectric conversion element 3G that is the closest to a plane of incidence has an absorption spectrum in which a sharp peak is represented in a green band (for example, a wavelength band of 450 nm to 600 nm), it is necessary to decrease absorption in a band of less than 450 nm and a band of greater than 600 nm.

In view of the above circumstances, the inventors of the present disclosure intensively studied a photoelectric conversion film appropriate for the solid-state image sensor and completed the technology according to the present disclosure. When the photoelectric conversion film according to an embodiment of the present disclosure includes a compound to be described in the following embodiment, it is possible to selectively absorb light of a specific wavelength band and have appropriate spectral characteristics as the photoelectric conversion film of the solid-state image sensor. Therefore, when the photoelectric conversion film according to an embodiment of the present disclosure is used, it is possible to increase sensitivity and a resolution of the solid-state image sensor.

Hereinafter, such photoelectric conversion films according to first and second embodiments of the present disclosure will be described. In addition, a photoelectric conversion element according to a third embodiment of the present disclosure having an appropriate configuration as the photoelectric conversion element of the solid-state image sensor will be described.

2. First Embodiment (2.1. Configuration of Photoelectric Conversion Film According to First Embodiment)

First, the photoelectric conversion film according to the first embodiment of the present disclosure will be described. The photoelectric conversion film according to the first embodiment of the present disclosure is a photoelectric conversion film that includes a quinacridone derivative represented by the following General formula (1) and a subphthalocyanine derivative that is represented by the following General formula (2) and absorbs green light.

[Chem.4]

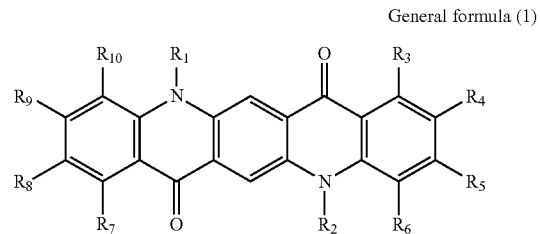

General formula (1)

In General Formula (1) above, $R_1$ to $R_{10}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, or an aryl or heteroaryl group formed by condensing at least two or more of any adjacent $R_1$ to $R_{10}$.

[Chem.5]

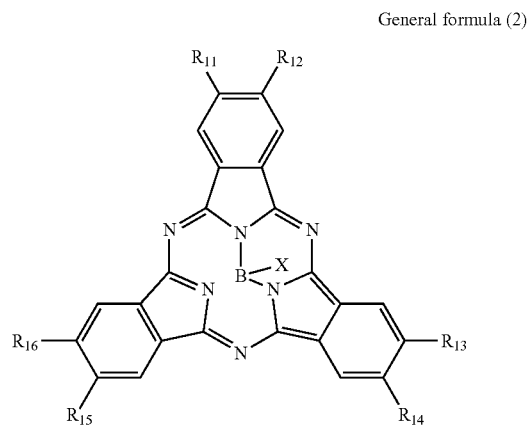

General formula (2)

In General Formula (2) above, $R_{11}$ to $R_{16}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, X represents any substituent selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group, and at least one of $R_{11}$ to $R_{16}$ represents fluorine.

Here, the photoelectric conversion film according to the first embodiment of the present disclosure may be formed as a bulk hetero mixed film. In this case, since the quinacridone derivative represented by General formula (1) serves as a p type photoelectric conversion material and the subphthalocyanine derivative represented by General formula (2) serves as an n type photoelectric conversion material, a bulk heterojunction is formed by the derivatives.

The bulk hetero mixed film is, for example, a film having a microstructure in which one of the p type photoelectric conversion material and the n type photoelectric conversion material forming a film is in a crystal fine particle state and the other thereof is in an amorphous state, and an amorphous layer uniformly covers a surface of crystal fine particles. In such a bulk hetero mixed film, since an area of a pn junction that induces charge separation is increased by the microstructure, it is possible to induce charge separation more efficiently and increase photoelectric conversion efficiency. Alternatively, the bulk hetero mixed film may be a film having a microstructure in which both the p type photoelectric conversion material and the n type photoelectric conversion material forming a film are in a fine crystalline state and mixed.

Meanwhile, spectral characteristics of such a bulk hetero mixed film are influenced by spectral characteristics of both the p type photoelectric conversion material and the n type photoelectric conversion material to be mixed. For this reason, when spectral characteristics of the p type photoelectric conversion material and the n type photoelectric conversion material forming the bulk hetero mixed film do not match, an absorption wavelength of light in the bulk hetero mixed film is likely to be wider. Accordingly, the photoelectric conversion film formed as the bulk hetero mixed film may not obtain appropriate spectral characteristics as the photoelectric conversion film in the solid-state image sensor.

When the photoelectric conversion film according to the first embodiment of the present disclosure includes the quinacridone derivative and the subphthalocyanine derivative having spectral characteristics matching the quinacridone derivative, it is possible to have appropriate spectral characteristics as the photoelectric conversion film of green light in the solid-state image sensor.

Specifically, in the subphthalocyanine derivative included in the photoelectric conversion film according to the first embodiment of the present disclosure, at least one of $R_{11}$ to $R_{16}$ is fluorine and therefore spectral characteristics match the quinacridone derivative. Specifically, the subphthalocyanine derivative in which at least one of $R_{11}$ to $R_{16}$ is fluorine decreases a maximum value of the absorption wavelength to be a shorter wavelength, and therefore absorption of light having a wavelength of greater than or equal to 600 nm can be decreased. Accordingly, since the photoelectric conversion film according to the first embodiment of the present disclosure has an absorption spectrum in which a sharp peak is represented in a green band (a wavelength band of 450 nm to 600 nm), it is possible to implement appropriate spectral characteristics as the photoelectric conversion film of green light in the solid-state image sensor.

In addition, in a process of manufacturing the photoelectric conversion element and the solid-state image sensor, a process involving heating (for example, an annealing process) may be performed. When the photoelectric conversion material included in the photoelectric conversion film has a low resistance, the photoelectric conversion material migrates and spectral characteristics may be changed due to heat in such heating treatment. In particular, since a general subphthalocyanine derivative has a low heat resistance, when the process involving heating is performed on a photoelectric conversion film including the general subphthalocyanine derivative, an absorbance significantly decreases.

In the subphthalocyanine derivative included in the photoelectric conversion film according to the first embodiment of the present disclosure, since at least one of $R_{11}$ to $R_{16}$ is fluorine, a heat resistance significantly increases. Accordingly, in the photoelectric conversion film according to the first embodiment of the present disclosure, since the photoelectric conversion material to be included has a high heat resistance, it is possible to suppress a change in spectral characteristics in heating treatment. Accordingly, in the photoelectric conversion film according to the first embodiment of the present disclosure, it is possible to increase a degree of freedom in the process of manufacturing the photoelectric conversion element and the solid-state image sensor.

In addition, in the subphthalocyanine derivative represented by General formula (2), $R_{11}$ to $R_{16}$ may be substituted with fluorine so as to have symmetry (line symmetry or point symmetry) or may be substituted with fluorine so as to have no symmetry.

In addition, in the subphthalocyanine derivative represented by General formula (2), X may be any substituent, as long as the substituent can bind to boron. However, it is more preferable that X be any substituent selected from the group consisting of a halogen, a hydroxy group, a substituted or unsubstituted alkoxy group and a substituted or unsubstituted aryloxy group.

Here, in the subphthalocyanine derivative included in the photoelectric conversion film according to the first embodiment of the present disclosure, it is preferable that all of $R_{11}$ to $R_{16}$ be fluorine. Specifically, as will be demonstrated in the following example, in the subphthalocyanine derivative in which all of $R_{11}$ to $R_{16}$ are fluorine, it is possible to further decrease a maximum value of the absorption wavelength to be a shorter wavelength. Accordingly, since the subphthalocyanine derivative represented by General formula (2) can further decrease absorption of greater than or equal to 600 nm, it is possible to absorb green light more selectively.

In addition, in the subphthalocyanine derivative represented by General formula (2), it is preferable that levels of a highest occupied molecular orbital (HOMO) and a lowest unoccupied molecular orbital (LUMO) be levels at which a photoelectric conversion mechanism can be smoothly performed on the quinacridone derivative.

Specifically, when the subphthalocyanine derivative represented by General formula (2) serves as the n type photoelectric conversion material and the quinacridone derivative represented by General formula (1) serves as the p type photoelectric conversion material, it is preferable that an LUMO level of the subphthalocyanine derivative be deeper than an LUMO level of the quinacridone derivative. In other words, it is preferable that an absolute value of the LUMO level of the subphthalocyanine derivative be greater than an absolute value of the LUMO level of the quinacridone derivative.

Here, as the photoelectric conversion mechanism in the photoelectric conversion film according to the first embodiment of the present disclosure, the following two mechanisms are considered.

One photoelectric conversion mechanism is a mechanism in which the quinacridone derivative serving as the p type photoelectric conversion material is excited due to light and excited electrons move from the quinacridone derivative to the subphthalocyanine derivative serving as the n type photoelectric conversion material. In this case, it is preferable that the LUMO level of the subphthalocyanine derivative be a level at which excited electrons that are excited in the quinacridone derivative can move to the subphthalocyanine derivative smoothly. Specifically, it is preferable that a difference between the LUMO level of the subphthalocyanine derivative represented by General formula (2) and the LUMO level of the quinacridone derivative represented by General formula (1) be greater than or equal to 0.1 eV and less than or equal to 1.0 eV. More specifically, the LUMO level of the subphthalocyanine derivative is preferably greater than or equal to −4.8 eV and less than or equal to −3.5 eV, and more preferably, greater than or equal to −4.5 eV and less than or equal to −3.8 eV.

In addition, the other photoelectric conversion mechanism is a mechanism in which the subphthalocyanine derivative serving as the n type photoelectric conversion material is excited due to light and excited electrons move to the LUMO level of the subphthalocyanine derivative. Accordingly, holes can move from the quinacridone derivative serving as the p type photoelectric conversion material to the subphthalocyanine derivative. In this case, it is preferable that an HOMO level of the subphthalocyanine derivative be a level at which holes can move from the quinacridone derivative to the subphthalocyanine derivative smoothly. Specifically, the HOMO level of the subphthalocyanine derivative is preferably greater than or equal to −7.0 eV and less than or equal to −5.5 eV, and more preferably, greater than or equal to −6.7 eV and less than or equal to −5.8 eV.

In addition, when a purpose of the photoelectric conversion film is to extract an electromotive force, such as in a solar cell, in order to increase an open end voltage, it is necessary to increase such a difference by decreasing an HOMO level of the p type photoelectric conversion material and increasing an LUMO level of the n type photoelectric conversion material. On the other hand, the purpose of the solid-state image sensor in which the photoelectric conversion film according to the first embodiment of the present disclosure is used is to extract a signal of light of a specific wavelength. For this reason, in the photoelectric conversion film according to the first embodiment of the present disclosure, it is preferable that the LUMO level of the subphthalocyanine derivative (the n type photoelectric conversion material) be set according to a relation with the LUMO level rather than an HOMO level of the quinacridone derivative (the p type photoelectric conversion material). Specifically, as described above, it is preferable that a difference between the LUMO level of the subphthalocyanine derivative and the LUMO level of the quinacridone derivative be greater than or equal to 0.1 eV and less than or equal to 1.0 eV.

Here, specific examples of the subphthalocyanine derivative represented by General formula (2) are represented by the following compounds 1 to 9. However, the subphthalocyanine derivative included in the photoelectric conversion film according to the first embodiment of the present disclosure is not limited to the following compounds.

[Chem.6]

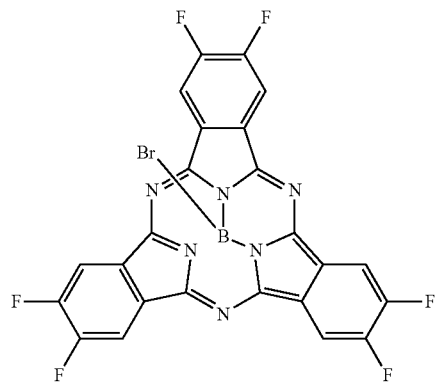

1

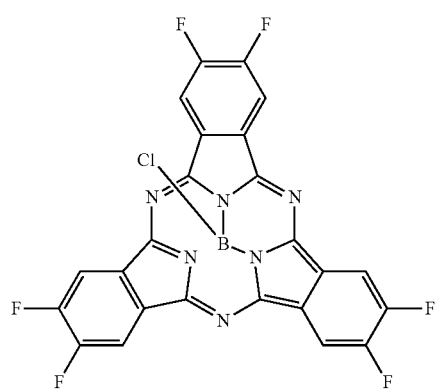

2

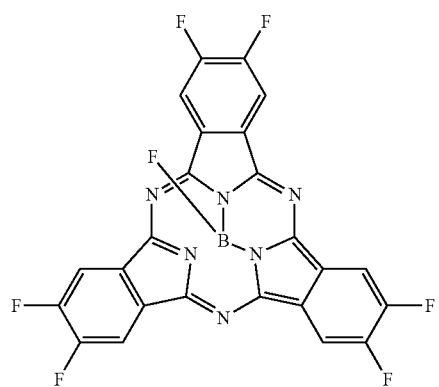

3

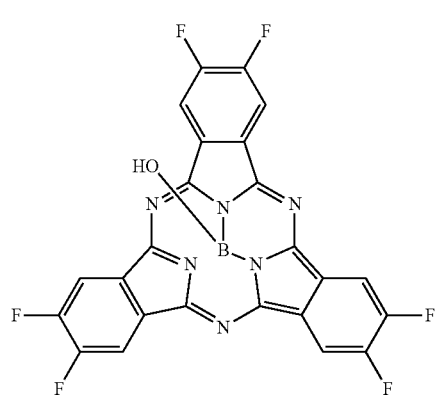

4

5
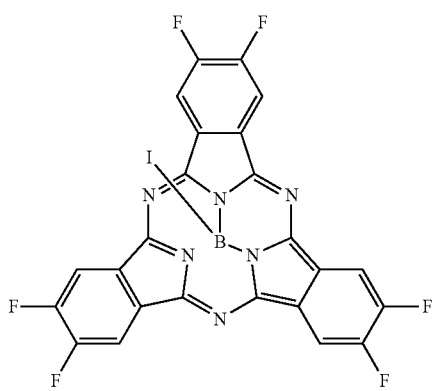

6
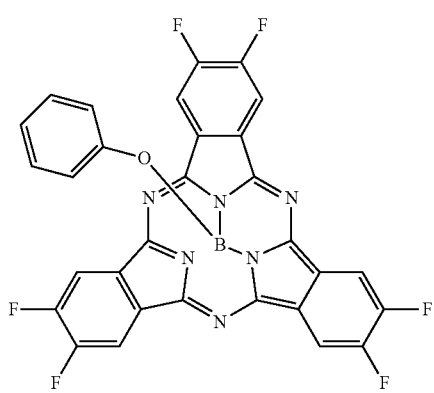

7
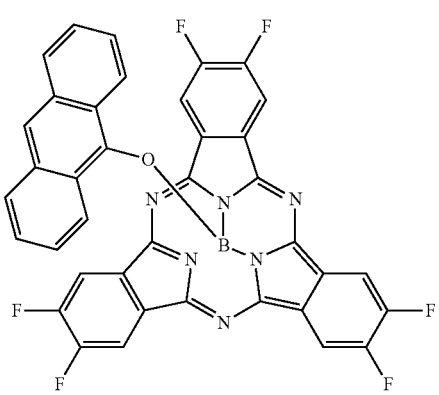

8
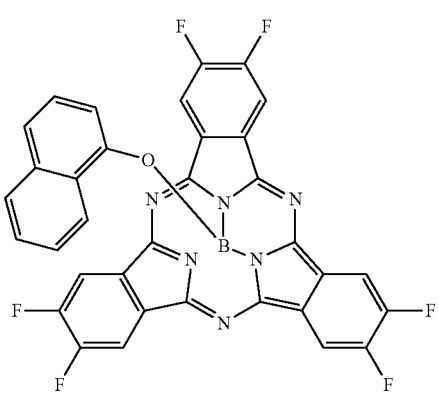

9
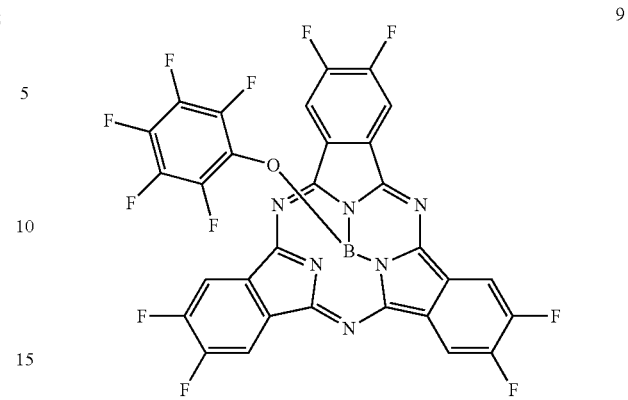

As described above, since the photoelectric conversion film according to the first embodiment of the present disclosure includes the quinacridone derivative represented by General formula (1) and the subphthalocyanine derivative represented by General formula (2), it is possible to selectively absorb green light (for example, light having a wavelength of greater than or equal to 450 nm and less than 600 nm). In addition, in the photoelectric conversion film according to the first embodiment of the present disclosure, since the quinacridone derivative and the subphthalocyanine derivative to be included have a high heat resistance, it is possible to suppress a change in spectral characteristics in the process of manufacturing the photoelectric conversion element and the solid-state image sensor. Accordingly, since the photoelectric conversion film according to the first embodiment of the present disclosure can be appropriately used for the green photoelectric conversion element of the solid-state image sensor, it is possible to increase sensitivity of the solid-state image sensor.

(2.2. Configuration of Photoelectric Conversion Element According to First Embodiment)

Next, the photoelectric conversion element according to the first embodiment of the present disclosure will be described with reference to FIG. 2. FIG. 2 is a schematic diagram illustrating an exemplary photoelectric conversion element according to the first embodiment of the present disclosure.

As illustrated in FIG. 2, a photoelectric conversion element 100 according to the first embodiment of the present disclosure includes a substrate 102, a lower electrode 104 disposed above the substrate 102, an electron blocking layer 106 disposed above the lower electrode 104, a photoelectric conversion layer 108 disposed above the electron blocking layer 106, a hole blocking layer 110 disposed above the photoelectric conversion layer 108, and an upper electrode 112 disposed above the hole blocking layer 110.

However, a structure of the photoelectric conversion element 100 illustrated in FIG. 2 is only an example. The structure of the photoelectric conversion element 100 according to the first embodiment of the present disclosure is not limited to the structure illustrated in FIG. 2. For example, either or both of the electron blocking layer 106 and the hole blocking layer 110 may not be provided.

The substrate 102 is a support in which layers forming the photoelectric conversion element 100 are laminated and disposed. As the substrate 102, a substrate used in a general photoelectric conversion element may be used. For example, the substrate 102 may be various types of glass substrates such as a high strain point glass substrate, a soda glass substrate and a borosilicate glass substrate, a quartz substrate, a semiconductor substrate, and a plastic substrate such as a polymethylmethacrylate, polyvinyl alcohol, polyimide or polycarbonate substrate. In addition, when incident light is transmitted and the transmitted incident light is received in another photoelectric conversion element again, it is preferable that the substrate 102 be made of a transparent material.

The lower electrode 104 and the upper electrode 112 are made of a conductive material, and at least one thereof is made of a transparent conductive material. Specifically, the lower electrode 104 and the upper electrode 112 may be made of indium tin oxide ($In_2O_3$—$SnO_2$:ITO), indium zinc oxide ($In_2O_3$—ZnO:IZO), and the like. In addition, when incident light is transmitted and the transmitted incident light is received in another photoelectric conversion element again, it is preferable that the lower electrode 104 and the upper electrode 112 be made of the transparent conductive material such as ITO.

Here, a bias voltage is applied to the lower electrode 104 and the upper electrode 112. For example, the bias voltage is applied to set a polarity such that electrons move to the upper electrode 112 and holes move to the lower electrode 104 among charges generated in the photoelectric conversion layer 108.

In addition, it is needless to say that the bias voltage may be applied to set a polarity such that holes move to the upper electrode 112 and electrons move to the lower electrode 104 among charges generated in the photoelectric conversion layer 108. In this case, in the photoelectric conversion element 100 illustrated in FIG. 2, positions of the electron blocking layer 106 and the hole blocking layer 110 are switched.

The electron blocking layer 106 is a layer that suppresses an increase in a dark current due to introduction of electrons from the lower electrode 104 to the photoelectric conversion layer 108 when the bias voltage is applied. Specifically, the electron blocking layer 106 may be made of an electron donating material such as arylamine, oxazole, oxadiazole, triazole, imidazole, stilbene, a polyarylalkane, porphyrin, anthracene, fluorenone and hydrazine. For example, the electron blocking layer 106 may be made of N,N'-bis(3-methylphenyl)-(1,1'-biphenyl)-4,4'-diamine (TPD), N,N'-di (1-naphthyl)-N,N'-diphenylbenzidine (alpha-NPD), 4,4',4"-tris(N-(3-methylphenyl)N-phenylamino) triphenylamine (m-MTDATA), tetraphenylporphyrin copper, phthalocyanine, or copper phthalocyanine.

The photoelectric conversion layer 108 is a layer that selectively absorbs light of a specific wavelength and performs photoelectric conversion on the absorbed light. Specifically, the photoelectric conversion layer 108 is formed of the photoelectric conversion film that has been described in the above (2.1. Configuration of photoelectric conversion film according to first embodiment). Accordingly, the photoelectric conversion layer 108 can selectively absorb green light (for example, light having a wavelength of greater than or equal to 450 nm and less than 600 nm).

The hole blocking layer 110 is a layer that suppresses an increase in a dark current due to introduction of holes from the upper electrode 112 to the photoelectric conversion layer 108 when the bias voltage is applied. Specifically, the hole blocking layer 110 may be made of an electron accepting material such as a fullerene, carbon nanotubes, oxadiazole, a triazole compound, anthraquinodimethane, diphenylquinone, distyrylarylene, and a silole compound. For example, the hole blocking layer 110 may be made of 1,3-bis(4-tert-butylphenyl-1,3,4-oxadiazolyl)phenylene (OXD-7), bathocuproine, bathophenanthroline, or tris(8-hydroxyquinolinato)aluminum (Alq3).

In addition, in the structure of the photoelectric conversion element 100 illustrated in FIG. 2, materials forming layers other than the photoelectric conversion layer 108 are not specifically limited, but a known material for the photoelectric conversion element may also be used.

Here, each of the layers in the photoelectric conversion element 100 according to the first embodiment of the present disclosure described above may be formed by an appropriate film formation method that is selected according to a material such as a deposition method, a sputtering method, and various coating methods.

For example, in each of the layers forming the photoelectric conversion element 100 according to the first embodiment of the present disclosure, the lower electrode 104 and the upper electrode 112 may be formed by a deposition method including an electron beam deposition method, a hot filament deposition method and a vacuum deposition method, a sputtering method, a chemical vapor deposition method (CVD method), a combination of an ion plating method and an etching method, various types of printing methods such as a screen printing method, an ink jet printing method and a metal mask printing method, a plating method (an electroplating method and an electroless plating method), and the like.

In addition, in each of the layers forming the photoelectric conversion element 100 according to the first embodiment of the present disclosure, an organic layer such as the electron blocking layer 106, the photoelectric conversion layer 108 and the hole blocking layer 110 may be formed by, for example, the deposition method such as the vacuum deposition method, the printing method such as the screen printing method and the ink jet printing method, a laser transfer method or the coating method such as a spin coating method.

An exemplary configuration of the photoelectric conversion element 100 according to the first embodiment of the present disclosure has been described above.

(2.3. Example According to First Embodiment)

Hereinafter, the photoelectric conversion film and the photoelectric conversion element according to the first embodiment of the present disclosure will be described in detail with reference to examples and comparative examples. However, the following examples are only examples and the photoelectric conversion film and the photoelectric conversion element according to the first embodiment of the present disclosure are not limited to the following examples.

(Simulation Analysis)

First, spectral characteristics of the subphthalocyanine derivative according to the first embodiment of the present disclosure were evaluated by simulation analysis. Specifically, the simulation analysis was performed on the subphthalocyanine derivative represented by the following structural formula and HOMO and LUMO levels and a maximum absorption wavelength lambda$_{max}$ were calculated.

Here, "F6-SubPc-Cl," "F3(C3)-SubPc-Cl," and "F3(C)-SubPc-Cl" are the subphthalocyanine derivatives according to the first embodiment of the present disclosure (Examples 1 to 3). "Bay-F6-SubPc-Cl," "F12-SubPc-Cl," "Cl6-SubPc-Cl," "BayCl6-SubPc-Cl," and "Cl12-SubPc-Cl" are subphthalocyanine derivatives (Comparative examples 1 to 5) that are not included in the first embodiment of the present disclosure.

[Chem.7]
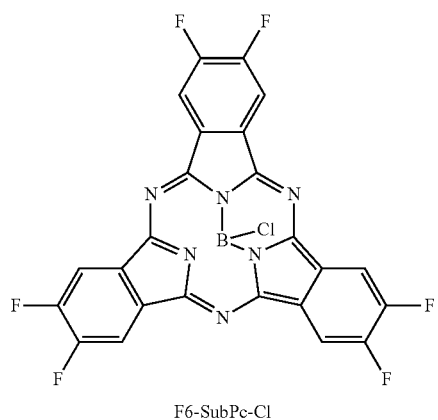
F6-SubPc-Cl
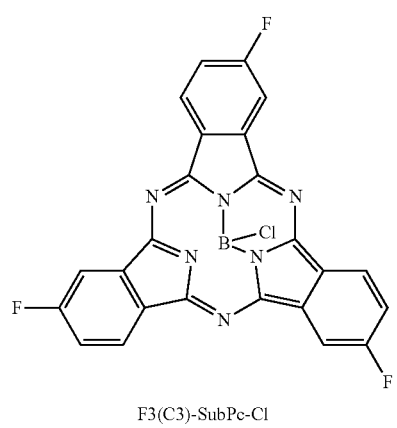
F3(C3)-SubPc-Cl
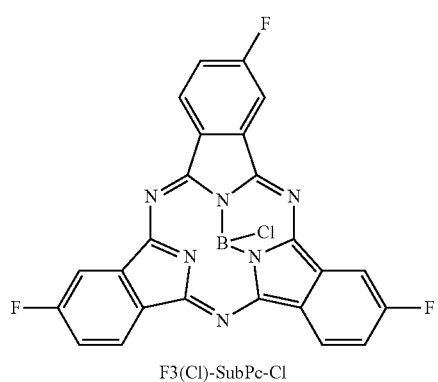
F3(Cl)-SubPc-Cl
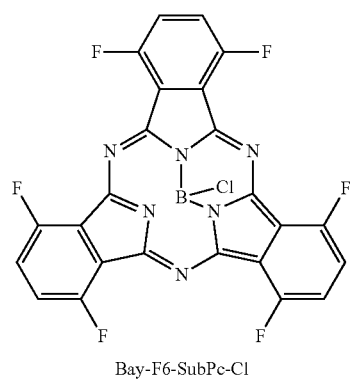
Bay-F6-SubPc-Cl
-continued
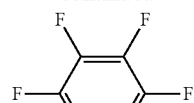
F12-SubPc-Cl
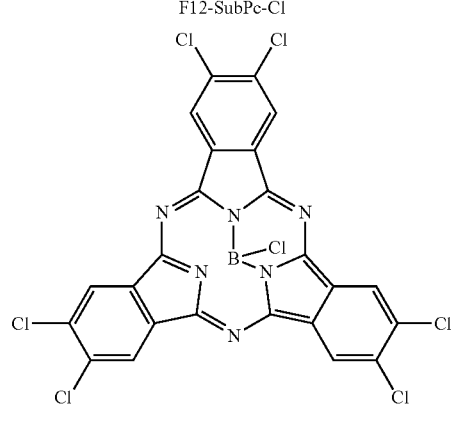
Cl6-SubPc-Cl
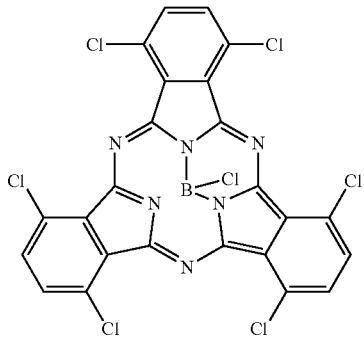
Bay-Cl6-SubPc-Cl
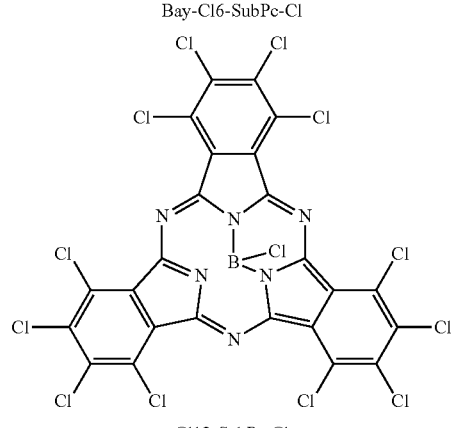
Cl12-SubPc-Cl
In addition, in the simulation analysis, calculation was performed according to a density functional theory (DFT), and Gaussian 09 was used as a calculation program and calculated at the level of "B3LYP/6-31+G**".

The HOMO and LUMO levels and the maximum absorption wavelength lambda$_{max}$ of each of the subphthalocyanine derivatives that were computed by the simulation analysis are shown in Table 1. In addition, since the HOMO and LUMO levels and the maximum absorption wavelength lambda$_{max}$ of the subphthalocyanine derivatives shown in Table 1 are simulation analysis results in a single molecule, an absolute value does not strictly match an actual measured value in a thin film to be described.

TABLE 1

|  |  | HOMO (eV) | LUMO (eV) | $\lambda_{max}$ (nm) |
|---|---|---|---|---|
| Example 1 | F6-SubPc-Cl | −6.18 | −3.44 | 492.76 |
| Example 2 | F3-C1-SubPc-Cl | −5.89 | −3.19 | 497.38 |
| Example 3 | F3-C3-SubPc-Cl | −5.89 | −3.22 | 491.27 |
| Comparative example 1 | Bay-F6-SubPc-Cl | −5.99 | −3.14 | 520.39 |
| Comparative example 2 | F12-SubPc-Cl | −6.51 | −3.9 | 513.96 |
| Comparative example 3 | C16-SubPc-Cl | −6.15 | −3.49 | 510.02 |
| Comparative example 4 | Bay-C16-SubPc-Cl | −5.98 | −3.39 | 525.73 |
| Comparative example 5 | C112-SubPc-Cl | −6.33 | −3.76 | 533.21 |

As shown in Table 1, it can be understood that the subphthalocyanine derivatives according to Examples 1 to 3 have a shorter maximum absorption wavelength lambda$_{max}$ than the subphthalocyanine derivatives according to Comparative examples 1 to 5.

Specifically, in the subphthalocyanine derivatives according to Examples 1 to 3, at least any one beta position ($R_{11}$ to $R_{16}$) of a subphthalocyanine skeleton is substituted with fluorine. Therefore, the maximum absorption wavelength lambda$_{max}$ becomes a shorter wavelength. In addition, in the subphthalocyanine derivative according to Example 1, it can be understood that, since all beta positions ($R_{11}$ to $R_{16}$) of the subphthalocyanine skeleton are substituted with fluorine, the maximum absorption wavelength lambda$_{max}$ becomes a shorter wavelength than those of the subphthalocyanine derivatives according to Examples 2 and 3 in which beta positions are partially substituted with fluorine.

On the other hand, in the subphthalocyanine derivatives according to Comparative examples 1 and 2, since an alpha position of the subphthalocyanine skeleton is substituted with fluorine, the maximum absorption wavelength lambda$_{max}$ becomes longer compared to the subphthalocyanine derivatives according to Examples 1 to 3. In addition, in the subphthalocyanine derivative according to Comparative example 2, all beta positions ($R_{11}$ to $R_{16}$) of the subphthalocyanine skeleton are substituted with fluorine, but the alpha position is also substituted with fluorine. Therefore, compared to the subphthalocyanine derivatives according to Examples 1 to 3, the maximum absorption wavelength lambda$_{max}$ becomes longer.

A change in spectral characteristics according to a position of such a substituent is considered to be caused by molecular orbitals of the HOMO level and the LUMO level that influence spectral characteristics of subphthalocyanine being present at the alpha position and the beta position of the subphthalocyanine skeleton. Accordingly, in the subphthalocyanine derivative according to the first embodiment of the present disclosure, it is considered to be important that all alpha positions be hydrogen and at least any one beta position ($R_1$ to $R_{16}$) be substituted with fluorine in the subphthalocyanine skeleton.

In addition, in the subphthalocyanine derivatives according to Comparative examples 3 to 5, the alpha position or the beta position of the subphthalocyanine skeleton is substituted with chlorine. Therefore, compared to the subphthalocyanine derivatives according to Examples 1 to 3, the maximum absorption wavelength lambda$_m$ax becomes longer. Accordingly, in the subphthalocyanine derivative according to the first embodiment of the present disclosure, it is considered to be important that a substituent for substituting the subphthalocyanine skeleton be fluorine.

(Synthesis of subphthalocyanine derivative) Next, a synthesizing method of the subphthalocyanine derivative according to the first embodiment of the present disclosure will be described. Specifically, the above-described compound 2 (F6-SubPc-Cl) and compound 9 (F6-SubPc-OC6F5) were synthesized by the following synthesizing method. The synthesized subphthalocyanine derivatives were identified using nuclear magnetic resonance ($^1$HNMR) and field desorption massspectrometry (FD-MS). However, the synthesizing method to be described below is only an example, and the synthesizing method of the subphthalocyanine derivative according to the first embodiment of the present disclosure is not limited to the following example.

Synthesis of F6-SubPc-Cl

F6-SubPc-Cl serving as the subphthalocyanine derivative according to the first embodiment of the present disclosure was synthesized through the following Reaction formula 1.

[Chem. 8]

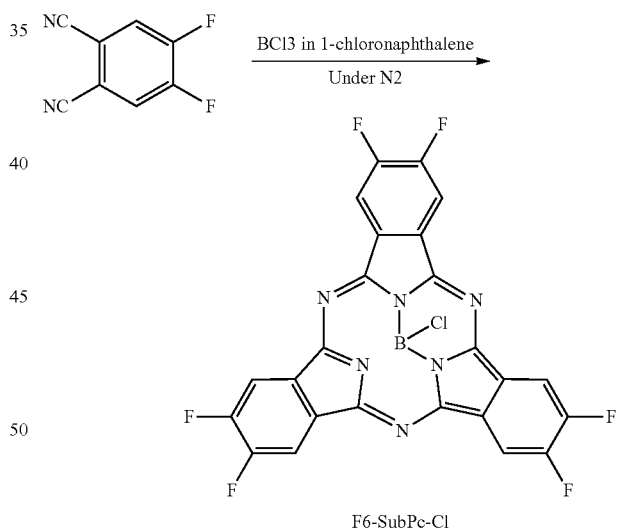

Reaction formula (1)

F6-SubPc-Cl

Difluorophthalonitrile (30 g, 183 mmol) was added to 1-chloronaphthalene (150 ml) in which BCl$_3$ (14 g, 120 mmol) was dissolved, and the mixture was heated to reflux under a nitrogen atmosphere. After cooling, the mixture was separated and purified by silica chromatography, and then a product was purified by sublimation and purification to obtain F6-SubPc-Cl (11 g, yield 34%).

Synthesis of F6-SubPc-OC6F5

F6-SubPc-OC6F5 serving as the subphthalocyanine derivative according to the first embodiment of the present disclosure was synthesized through the following Reaction formula 2.

[Chem. 9]

Reaction formula (2)

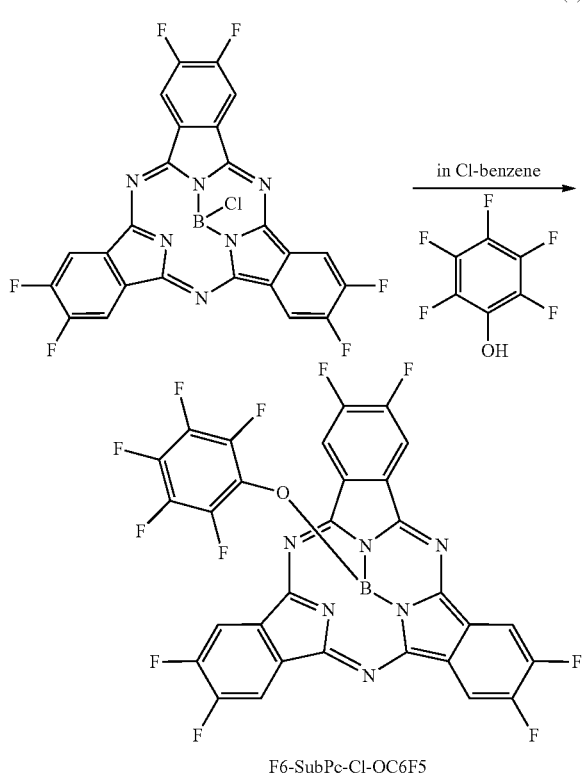

F6-SubPc-Cl-OC6F5

Pentafluorophenol (13 g, 10 mmol) was added to chlorobenzene (100 ml) in which F6-SubPc-Cl (10 g, 2.3 mmol) that was synthesized by the above synthesizing method was dissolved, and the mixture was heated to reflux. After cooling, the mixture was separated and purified by silica chromatography, and then a product was purified by sublimation and purification to obtain F6-SubPc-OC6F5 (5.9 g, yield 60%).

(Evaluation of Spectral Characteristics)

Subsequently, spectral characteristics of the subphthalocyanine derivative according to the first embodiment of the present disclosure were evaluated. Specifically, an evaluation sample including the subphthalocyanine derivative according to the first embodiment of the present disclosure was manufactured, and a change in spectral characteristics was measured before and after annealing.

Example 4

First, a glass substrate with an ITO electrode was washed by UV/ozone treatment. In addition, a film thickness of an ITO film in the glass substrate was 50 nm. Next, the glass substrate was put into an organic deposition apparatus and the synthesized F6-SubPc-Cl was deposited at a deposition rate of 0.1 nm/sec by a resistance heating method while rotating a substrate holder in a vacuum of less than or equal to $1 \times 10^{-5}$ Pa. A film thickness of the deposited F6-SubPc-Cl was 50 nm. Further, in order to cover the organic layer, the ITO film was formed at a film thickness of 50 nm by the sputtering method to manufacture a spectral characteristic evaluation sample.

Comparative Example 6

A spectral characteristic evaluation sample was manufactured by the same method as in Example 4 except that F12-SubPc-Cl to be described in the following synthesizing method was used instead of F6-SubPc-Cl used in Example 4.

Also, F12-SubPc-Cl used in Comparative example 6 was synthesized by the following reaction formula 3. In addition, the synthesized F12-SubPc-Cl was identified using NMR and FD-MS.

[Chem. 10]

Reaction formula (1)

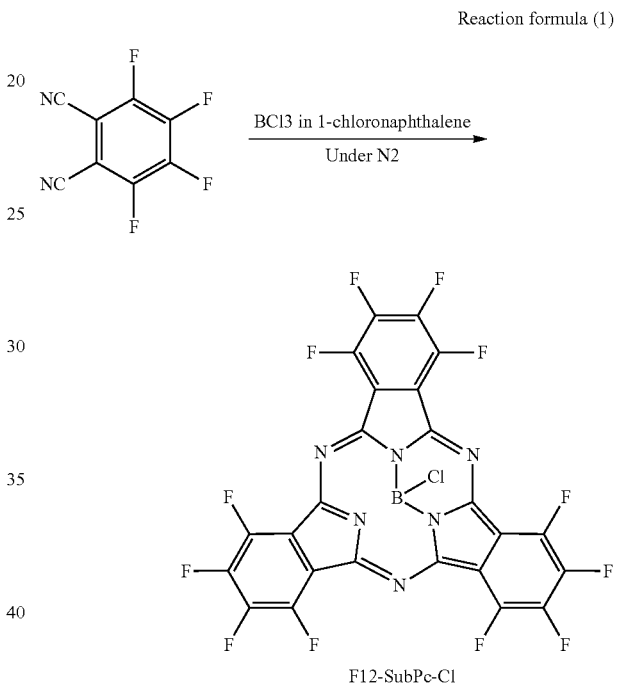

F12-SubPc-Cl

Tetrafluorophthalonitrile (37 g, 183 mmol) was added to 1-chloronaphthalene (150 ml) in which $BCl_3$ (14 g, 120 mmol) was dissolved, and the mixture was heated to reflux under a nitrogen atmosphere. After cooling, the mixture was separated and purified by silica chromatography, and then a product was purified by sublimation and purification to obtain F12-SubPc-Cl (5.3 g, yield 64%).

Comparative Example 7

A spectral characteristic evaluation sample was manufactured by the same method as in Example 4 except that SubPc-OC6F5 to be described in the following synthesizing method was used instead of F6-SubPc-Cl used in Example 4.

Also, SubPc-OC6F5 used in Comparative example 7 was synthesized by the following reaction formula 4. In addition, the synthesized SubPc-OC6F5 was identified using NMR and FD-MS.

[Chem. 11]

Reaction formula (4)

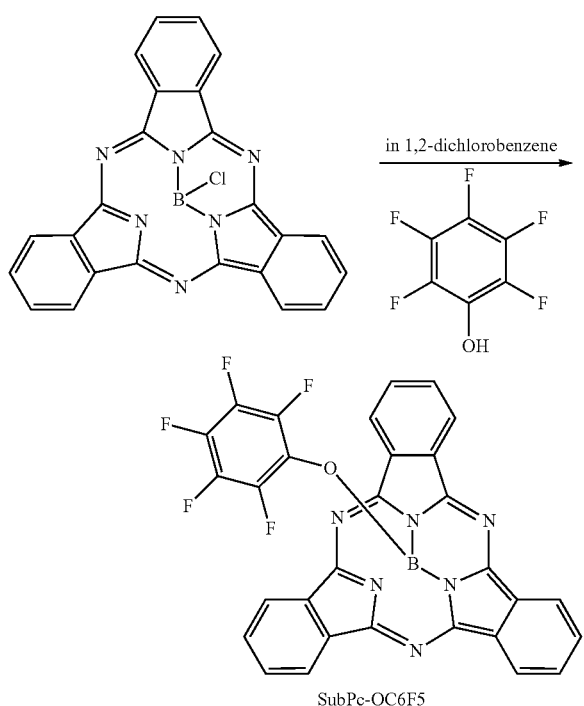

SubPc-OC6F5

Pentafluorophenol (13 g, 10 mmol) was added to 1,2-chlorobenzene (100 ml) in which the sublimated and purified subphthalocyanine (manufactured by Tokyo Chemical Industry Co., Ltd.) (10 g, 2.3 mmol) was dissolved, and the mixture was heated to reflux. After cooling, the mixture was separated and purified by silica column chromatography, and then a product was purified by sublimation and purification to obtain SubPc-OC6F5 (6.5 g, yield 65%).

Comparative Example 8

A spectral characteristic evaluation sample was manufactured by the same method as in Example 4 except that subphthalocyanine chloride (SubPc-Cl) represented by the following structural formula was used instead of F6-SubPc-Cl used in Example 4. In addition, as the subphthalocyanine chloride, a sublimated and purified product purchased from Tokyo Chemical Industry Co., Ltd. was used.

[Chem.12]

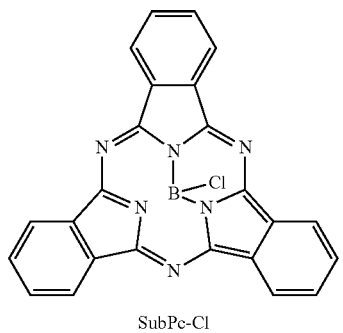

SubPc-Cl

Reference Example

A spectral characteristic evaluation sample was manufactured by the same method as in Example 4 except that quinacridone (QD) represented by the following structural formula was used instead of F6-SubPc-Cl used in Example 4. In addition, as the quinacridone, a sublimated and purified product purchased from Tokyo Chemical Industry Co., Ltd. was used.

[Chem.13]

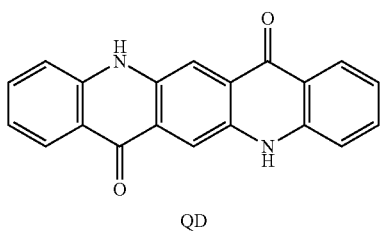

QD

A change in spectral characteristics before and after annealing was evaluated for the manufactured spectral characteristic evaluation samples of Example 4, Comparative examples 7 to 9 and the reference example using an ultraviolet and visible spectrophotometer. Specifically, before annealing, after annealing for 60 minutes at 160 degrees Celsius and after annealing for 210 minutes at 160 degrees Celsius, spectral characteristics of Example 4, Comparative examples 7 to 9 and the reference example were measured. The evaluation results of changes in spectral characteristics are shown in FIGS. 3A to 3E.

Here, FIG. 3A shows the graph of evaluation results of a change in spectral characteristics of Example 4 (F6-SubPc-Cl). In addition, FIG. 3B shows the graph of evaluation results of a change in spectral characteristics of Comparative example 7 (F12-SubPc-Cl). FIG. 3C shows the graph of evaluation results of a change in spectral characteristics of Comparative example 8 (SubPc-OC6F5). FIG. 3D shows the graph of evaluation results of a change in spectral characteristics of Comparative example 9 (SubPc-Cl). In addition, FIG. 3E shows the graph of evaluation results of a change in spectral characteristics of the reference example (QD).

Referring to FIG. 3A, it can be understood in Example 4 that absorption of red light having a wavelength of greater than or equal to 600 nm is low and green light can be selectively absorbed. In addition, it can be understood in Example 4 that an absorption coefficient had almost no change before and after annealing and a heat resistance was high.

On the other hand, as shown in FIGS. 3C to 3E, it can be understood in Comparative example 7 (F12-SubPc-Cl), Comparative example 8 (SubPc-OC6F5) and Comparative example 9 (SubPc-Cl) that absorption of a wavelength of greater than or equal to 600 nm is high and red light is absorbed. In addition, it can be understood in Comparative examples 7 to 9 that an absorption coefficient is significantly changed both before and after annealing and a heat resistance is also low.

Further, it can be understood that Example 4 had spectral characteristics similar to spectral characteristics of the reference example (quinacridone) shown in FIG. 3E. Accordingly, it can be understood that, when the subphthalocyanine derivative according to the first embodiment of the present disclosure forms the bulk hetero mixed film with the quinacridone derivative, a wavelength band of light to be absorbed does not become wider and it is possible to form the photoelectric conversion film having a sharp absorption peak in the green band.

Based on the above results, it can be understood that, since the subphthalocyanine derivative according to the first embodiment of the present disclosure can selectively absorb green light, it is appropriate for a material of a green photoelectric conversion film of the solid-state image sensor.

(Evaluation of Photoelectric Conversion Element)

In addition, the photoelectric conversion element according to the first embodiment of the present disclosure was manufactured by the following manufacturing methods. However, structures and manufacturing methods of photoelectric conversion elements to be described below are only examples. The structure and the manufacturing method of the photoelectric conversion element according to the first embodiment of the present disclosure are not limited to the following examples.

Here, in the following examples, F6-SubPc-Cl, F6-SubPc-OC6F5, F12-SubPc-Cl and SubPc-OC6F5 were synthesized, sublimated and purified by the above-described method, and used. In addition, as SubPc-Cl, quinacridone and N,N'-dimethylquinacridone, sublimated and purified products purchased from Tokyo Chemical Industry Co., Ltd. were used.

Example 5

First, a glass substrate with an ITO electrode was washed by UV/ozone treatment. In addition, a film thickness of an ITO film corresponding to a lower electrode in the glass substrate was 50 nm. Next, the glass substrate was put into an organic deposition apparatus, a pressure was decreased to less than or equal to $1 \times 10^{-5}$ Pa, and F6-SubPc-Cl and quinacridone were deposited by a resistance heating method while rotating a substrate holder. In addition, deposition was performed at a deposition rate of 0.1 nm/sec such that a ratio of F6-SubPc-Cl and quinacridone became 1:1, and a film of 100 nm in total was formed to form the photoelectric conversion layer.

Further, a film of AlSiCu was formed above the photoelectric conversion layer at a film thickness of 100 nm by the deposition method to form an upper electrode. By the above manufacturing method, the photoelectric conversion element including a photoelectric conversion area of 1 mm×1 mm was manufactured.

Example 6

A photoelectric conversion element was manufactured by the same method as in Example 5 except that F6-SubPc-OC6F5 was used instead of F6-SubPc-Cl used in Example 5.

Example 7

A photoelectric conversion element was manufactured by the same method as in Example 5 except that N,N'-dimethylquinacridone (DMQD) represented by the following structural formula was used instead of quinacridone used in Example 5.

[Chem.14]

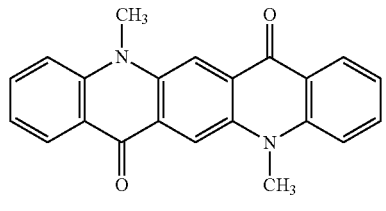

DMQD

Comparative Example 10

A photoelectric conversion element was manufactured by the same method as in Example 5 except that SubPc-Cl was used instead of F6-SubPc-Cl used in Example 5.

Comparative Example 11

A photoelectric conversion element was manufactured by the same method as in Example 5 except that SubPc-OC6F5 was used instead of F6-SubPc-Cl used in Example 5.

Comparative Example 12

A photoelectric conversion element was manufactured by the same method as in Example 5 except that F12-SubPc-Cl was used instead of F6-SubPc-Cl used in Example 5.

Comparative Example 13

A photoelectric conversion element was manufactured by the same method as in Example 5 except that N, N'-dimethylquinacridone and SubPc-Cl were used instead of quinacridone and F6-SubPc-Cl used in Example 5.

Comparative Example 14

A photoelectric conversion element was manufactured by the same method as in Example 5 except that N, N'-dimethylquinacridone and SubPc-OC6F5 were used instead of quinacridone and F6-SubPc-Cl used in Example 5.

Comparative Example 15

A photoelectric conversion element was manufactured by the same method as in Example 5 except that SubPc-Cl was used instead of quinacridone used in Example 5.

(Evaluation Result)

First, photoelectric conversion efficiency and spectral characteristics were evaluated for the photoelectric conversion elements according to Examples 5 to 7 and Comparative examples 10 to 15 manufactured as described above.

Photoelectric conversion efficiency was evaluated by measuring external quantum efficiency using a semiconductor parameter analyzer. Specifically, light having an intensity of 1.62 microwatts per square centimeter was radiated to the photoelectric conversion element from a light source through a filter, and external quantum efficiency was computed from a light current value and a dark current value when the bias voltage applied between electrodes was set to −1 V. Such external quantum efficiency was measured before and after annealing for 210 minutes at 160 degrees Celsius, and external quantum efficiency after annealing was divided by external quantum efficiency before annealing to compute an annealing resistance.

In addition, spectral characteristics were evaluated using the ultraviolet and visible spectrophotometer. An absorption coefficient at 600 nm was divided by an absorption coefficient at a maximum absorption wavelength lambda$_{max}$, to compute an absorption rate at 600 nm.

The results of the above evaluation are shown in the following Table 2. In Table 2, "QD" represents quinacridone, and "DMQD" represents N,N'-dimethylquinacridone.

TABLE 2

|  | Photoelectric conversion layer | External quantum efficiency | | | Spectral characteristics |
|---|---|---|---|---|---|
|  |  | Before annealing (%) | After annealing (%) | Annealing resistance (%) | 600 nm/λ$_{max}$ (%) |
| Example 5 | QD:F6-SubPc-Cl | 66 | 68 | 103 | 20 |
| Example 6 | QD:F6-SubPc-OC6F5 | 72 | 68 | 94 | 18 |
| Example 7 | DMQD:F6-SubPc-Cl | 43 | 42 | 98 | 25 |
| Comparative example 10 | QD:SubPc-Cl | 45 | 44 | 98 | 45 |
| Comparative example 11 | QD:SubPc-OC6F5 | 56 | 23 | 41 | 44 |
| Comparative example 12 | QD:F12-SubPc-Cl | 64 | 40 | 63 | 60 |
| Comparative example 13 | DMQD:SubPc-Cl | 36 | 24 | 67 | 54 |
| Comparative example 14 | DMQD:SubPc-OC6F5 | 52 | 28 | 54 | 52 |
| Comparative example 15 | SubPc-Cl:F6-SubPc-Cl | 13 | 11 | 85 | 71 |

As shown in the results in Table 2, it can be understood that Examples 5 to 7 including the photoelectric conversion element according to the first embodiment of the present disclosure have a lower absorption rate at 600 nm and a higher annealing resistance than Comparative examples 10 to 15. In addition, it can be understood that Examples 5 to 7 have a generally higher external quantum efficiency after annealing than Comparative examples 10 to 15.

Specifically, it can be understood that Examples 5 to 7 include the subphthalocyanine derivative and the quinacridone derivative according to the first embodiment of the present disclosure and therefore have a lower absorption rate at 600 nm and a higher annealing resistance than Comparative examples 11 to 15. In addition, since Comparative example 10 has a high annealing resistance but an absorption rate at 600 nm is high, it is not preferable.

Subsequently, in Examples 5 to 7 and Comparative examples 10 to 15, HOMO levels and LUMO levels of the subphthalocyanine derivative and the quinacridone derivative used in the photoelectric conversion layer were measured.

In addition, in order to measure the HOMO level, a sample in which each organic material was formed into a 20 nm film by the deposition method on a silicon substrate that had been treated with UV/ozone was used. The HOMO level was computed for the sample in which each organic material was formed into a film using an ultraviolet photoelectron spectroscopy (UPS) method.

In addition, in order to measure the LUMO level, a sample in which each organic material was formed into a 50 nm film by the deposition method on a quartz substrate that had been treated with UV/ozone was used. First, a transmittance and a reflectance of the sample were measured by a spectrophotometer (JASCO V-570), and an absorption coefficient alpha with respect to a wavelength was computed. Next, an absorption end of a visible light area of the computed absorption coefficient alpha was computed as an HOMO-LUMO gap, and the HOMO-LUMO gap was subtracted from the HOMO level to compute the LUMO level.

The measured HOMO levels, LUMO levels and maximum absorption wavelengths lambda$_{max}$ of the subphthalocyanine derivatives and the quinacridone derivatives are shown in the following Table 3. In Table 3, "QD" represents quinacridone, and "DMQD" represents N,N'-dimethylquinacridone.

TABLE 3

|  | HOMO (eV) | LUMO (eV) | λ$_{max}$ (nm) |
|---|---|---|---|
| F6-SubPc-Cl | −6.3 | −4.2 | 566 |
| SubPc-Cl | −5.7 | −3.7 | 587 |
| SubPc-OC6F5 | −5.7 | −3.7 | 577 |
| F12-SubPc-Cl | −6.6 | −4.6 | 584 |
| QD | −5.55 | −3.55 | 561 |
| DMQD | −5.5 | −3.3 | 532 |

As shown in the results in Table 3, it can be understood that "F6-SubPc-Cl" serving as the subphthalocyanine derivative according to the first embodiment of the present disclosure has a shorter maximum absorption wavelength lambda$_{max}$ even in a thin film than "SubPc-Cl," "SubPc-OC6F5," and "F12-SubPc-Cl" serving as the subphthalocyanine derivative according to the comparative example.

In addition, it can be understood that, in "F6-SubPc-Cl" serving as the subphthalocyanine derivative according to the first embodiment of the present disclosure, an LUMO level difference between "QD" and "DMQD" that form the bulk hetero mixed film in Example 5 or 7 is included in a preferable range (greater than or equal to 0.1 eV and less than or equal to 1.0 eV) in the first embodiment of the present disclosure.

As can be understood from the above results, when the photoelectric conversion film according to the first embodiment of the present disclosure includes the quinacridone derivative represented by General formula (1) and the subphthalocyanine derivative represented by General formula (2), it is possible to increase a heat resistance and selectively absorb green light. Accordingly, since the photoelectric conversion film according to the first embodiment of the present disclosure can be appropriately used as the green photoelectric conversion film in the solid-state image sensor, it is possible to increase sensitivity of the solid-state image sensor.

3. Second Embodiment (3.1. Configuration of photoelectric conversion film according to second embodiment) Next, the photoelectric conversion film according to the second embodiment of the present disclosure will be described. The photoelectric conversion film according to the second embodiment of the present disclosure is a photoelectric conversion film including a transparent compound that is represented by the following General formula (3) or (4) and does not absorb visible light.

[Chem.15]

General formula (3)

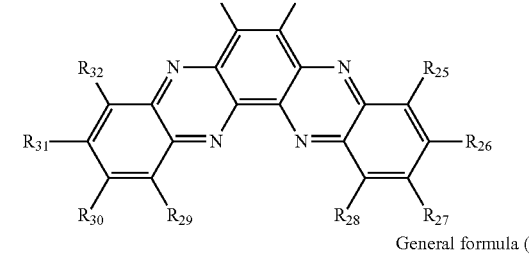

General formula (4)

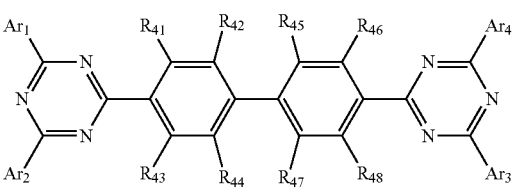

In General Formula (3) above, $R_{21}$ to $R_{32}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, or an aryl or heteroaryl group formed by condensing at least two or more of any adjacent $R_{21}$ to $R_{32}$.

In General Formula (4) above, $R_{41}$ to $R_{48}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, an imide group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, or an aryl or heteroaryl group formed by condensing at least two or more of any adjacent $R_{41}$ to $R_{48}$, and $Ar_1$ to $Ar_4$ each independently represent a substituted or unsubstituted aryl group or a substituted or unsubstituted heteroaryl group.

Here, the photoelectric conversion film according to the second embodiment of the present disclosure may further include an organic dye compound and may be formed as the bulk hetero mixed film similar to the first embodiment. In this case, for example, since the organic dye compound serves as the p type photoelectric conversion material and the transparent compound represented by General formula (3) or (4) serves as the n type photoelectric conversion material, a bulk heterojunction is formed therebetween.

Here, as described in the first embodiment of the present disclosure, in the bulk hetero mixed film, spectral characteristics are influenced by both spectral characteristics of the p type photoelectric conversion material and the n type photoelectric conversion material to be mixed. Accordingly, when spectral characteristics of the p type photoelectric conversion material and the n type photoelectric conversion material do not match, the photoelectric conversion film formed as the bulk hetero mixed film has a wide wavelength band of light to be absorbed, and appropriate spectral characteristics as the photoelectric conversion film in the solid-state image sensor may not be obtained.

In the photoelectric conversion film according to the second embodiment of the present disclosure, when the transparent compound that is a transparent compound that does not absorb visible light and is represented by General formula (3) or (4) is used, it is possible to prevent a wavelength band of light to be absorbed in the photoelectric conversion film from becoming wider. Specifically, in the photoelectric conversion film according to the second embodiment of the present disclosure, since the transparent compound represented by General formula (3) or (4) does not absorb visible light, it is possible to have spectral characteristics in which spectral characteristics of the organic dye compound to be included are reflected.

As the organic dye compound included in the photoelectric conversion film according to the second embodiment of the present disclosure, anything can be used. For example, as the organic dye compound, cyanine dyes, styryl dyes, hemicyanine dyes, merocyanine dyes (includes zeromethinemerocyanine and simple merocyanine), trinuclear merocyanine dyes, tetranuclear merocyanine dyes, rhodacyanine dyes, complex cyanine dyes, complex merocyanine dyes, allopolar dyes, oxonol dyes, hemi oxonol dyes, squalium dyes, croconium dyes, azamethine dyes, coumarin dyes, arylidene dyes, anthraquinone dyes, triphenylmethane dyes, azo dyes, azomethine dyes, spiro compounds, metallocene dyes, fluorenone dyes, fulgide dyes, perylene dyes, perynone dyes, phenazine dyes, phenothiazine dyes, quinone dyes, diphenylmethane dyes, polyene dyes, acridine dyes, acridinone dyes, diphenylamine dyes, quinacridone dyes, quinophthalone dyes, phenoxazine dyes, phthaloperylene dyes, diketopyrrolopyrrole dyes, dioxane dyes, porphyrin dyes, chlorophyll dyes, phthalocyanine dyes, metal complex dyes, or condensed aromatic carbocyclic system dyes (such as naphthalene derivatives, anthracene derivatives, phenanthrene derivatives, tetracene derivatives, pyrene derivatives, perylene derivatives and fluoranthene derivatives) are preferably used. In addition, in the second embodiment of the present disclosure, as the organic dye compound, the quinacridone derivative is more preferably used.

For example, when the photoelectric conversion film according to the second embodiment of the present disclosure includes the quinacridone derivative represented by General formula (1), it is possible to have spectral characteristics in which spectral characteristics of the quinacridone derivative represented by General formula (1) are reflected. In this case, since the photoelectric conversion film according to the second embodiment of the present disclosure can selectively absorb green light similar to the quinacridone derivative represented by General formula (1), it is possible to implement appropriate spectral characteristics as the photoelectric conversion film of green light in the solid-state image sensor.

In addition, the transparent compound represented by General formula (3) or (4) can form a bulk hetero mixed layer that includes crystal fine particles of sizes that are appropriate for charge separation with the quinacridone derivative represented by General formula (1). Accordingly, in the photoelectric conversion film according to the second embodiment of the present disclosure, charge separation of excitons generated when the quinacridone derivative absorbs light can be quickly performed at each interface. In particular, since the transparent compound represented by General formula (3) or (4) has an electron accepting ability and has a high electron mobility, charge separation is performed on the bulk hetero mixed film with high efficiency, and photoelectric conversion efficiency of the photoelectric conversion film can be increased.

In the photoelectric conversion film according to the second embodiment of the present disclosure, a mixing ratio of the transparent compound represented by General formula (3) or (4) and the organic dye compound may be any ratio, but, for example, transparent compound:organic dye compound=10:90 to 90:10 (volume ratio) is preferable and 20:80 to 50:50 (volume ratio) is more preferable. On the other hand, when an absolute amount of the organic dye compound included in the photoelectric conversion film is too small, since there is a possibility of insufficient absorption of incident light by the dye, it is not preferable. In addition, when an absolute amount of the transparent compound included in the photoelectric conversion film is too small, since a conductive path between the transparent compound and the organic dye compound that is necessary for generated carriers (that is, electrons and holes) to move to corresponding electrodes smoothly is not formed, it is not preferable.

Here, in General formula (3), $R_{21}$ to $R_{32}$ are hydrogen or any substituent, and preferably, all of $R_{21}$, $R_{24}$, $R_{25}$, $R_{28}$, $R_{29}$, and $R_{32}$ may be hydrogen.

For example, as a specific example of the transparent compound represented by General formula (3), a compound represented by the following structural formula can be exemplified. However, the transparent compound represented by General formula (3) according to the second embodiment of the present disclosure is not limited to the following exemplary compounds.

[Chem.16]

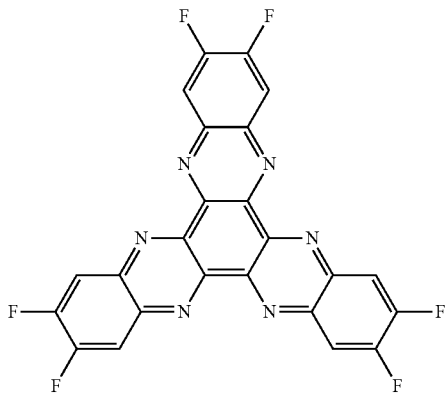

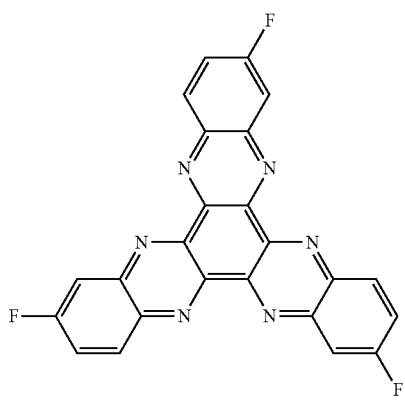

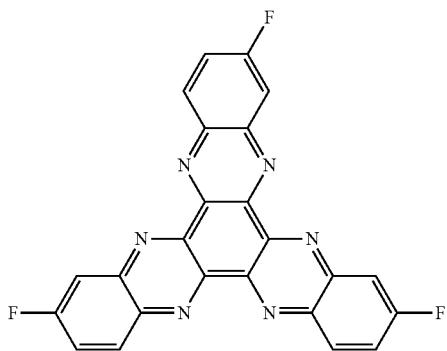

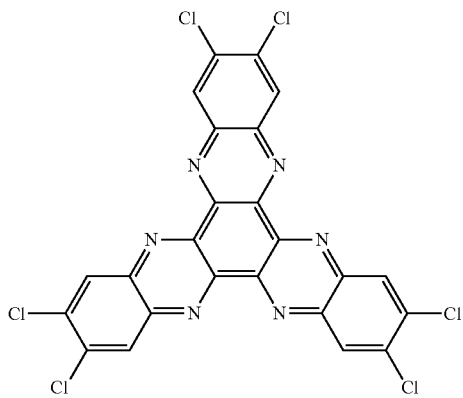

-continued

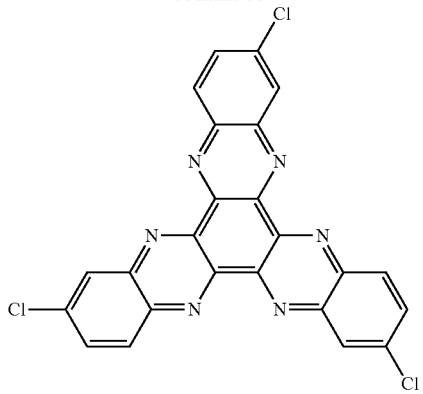

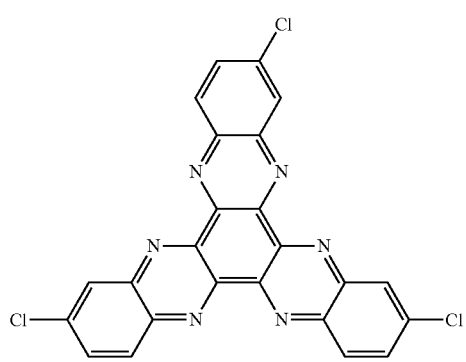

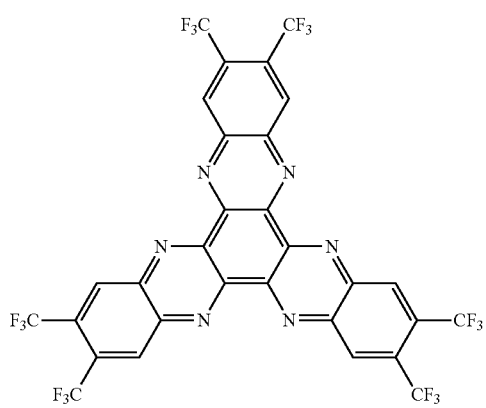

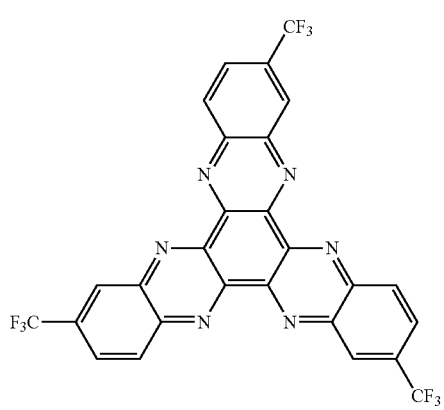

-continued

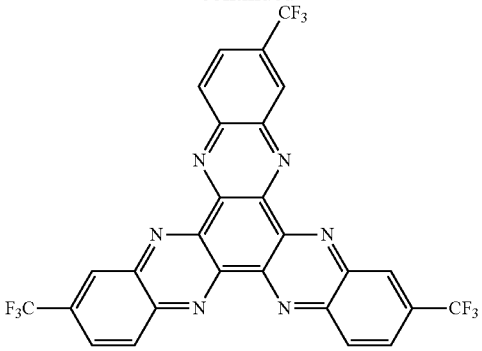 [SMILES: FC(F)(F)c1ccc2nc3c4nc5ccc(C(F)(F)F)cc5nc4c4nc5cc(C(F)(F)F)ccc5nc4c3nc2c1]

In addition, in General formula (4), $R_{41}$ to $R_{48}$ each independently represent hydrogen or any substituent, and $Ar_1$ to $Ar_4$ each independently represent a substituted or unsubstituted aryl group or a substituted or unsubstituted heteroaryl group.

As an aryl group that can be obtained by $Ar_1$ to $Ar_4$, a phenyl group, a biphenyl group, a terphenyl group, a naphthyl group, an anthryl group, a phenanthrenyl group, a fluorenyl group, and an indenyl group are exemplified. In addition, as a heteroaryl group that can be obtained by $Ar_1$ to $Ar_4$, a thienyl group, a furanyl group, a pyrrolyl group, a thiazolyl group, a thiadiazolyl group, an imidazolyl group, an oxazolyl group, an oxadiazolyl group, a pyridinyl group and a pyrimidinyl group are exemplified.

In addition, $Ar_1$ to $Ar_4$ may be an aryl or heteroaryl group having a substituent. As the substituent of $Ar_1$ to $Ar_4$, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group and a carboalkoxy group are exemplified.

In General formula (4), it is preferable that at least one of substituents of $Ar_1$ to $Ar_4$ and $R_{41}$ to $R_{48}$ be an electron attracting group. In other words, the transparent compound represented by General formula (4) has preferably at least one electron attracting group as the substituent. In this case, in the transparent compound represented by General formula (4), since the LUMO level becomes deeper (an absolute value increases) and becomes an LUMO level at which charge separation from the organic dye compound can be efficiently performed, it is possible to increase photoelectric conversion efficiency.

In addition, in order to set the LUMO level of the transparent compound represented by General formula (4) to a more appropriate value, it is preferable that the transparent compound represented by General formula (4) include more electron attracting groups, and it is preferable that the substituent to be included have a higher electron withdrawing ability. Further, when $Ar_1$ to $Ar_4$ include an electron attracting group as the substituent, a substitution position of the electron attracting group is preferably a position of a para position with respect to binding positions of $Ar_1$ to $Ar_4$ and a triazine ring. In this case, since the transparent compound represented by General formula (4) has an LUMO level at which charge separation from the organic dye compound can be more efficiently performed, it is possible to increase photoelectric conversion efficiency of the photoelectric conversion film.

In the above description, the electron attracting group may be, for example, a halogen, a cyano group, a nitro group, a sulfonyl group, an arylsulfonyl group, an alkylsulfonyl group, an acyl group, an acylamino group, an acyloxy group, an imide group, a carboxy group, a carboxamido group, a carboalkoxy group, a halogenated alkyl group, and a halogenated aryl group.

As a preferable specific example of the transparent compound represented by General formula (4), a compound represented by the following structural formula can be exemplified. However, the transparent compound represented by General formula (4) according to the second embodiment of the present disclosure is not limited to the following exemplary compounds. In addition, referring to the following exemplary compounds, it can be understood that, when $Ar_1$ to $Ar_4$ are a heteroaryl group serving as an electron donor, $R_{41}$ to $R_{48}$ are preferably an electron attracting group serving as an electron acceptor.

[Chem. 17]

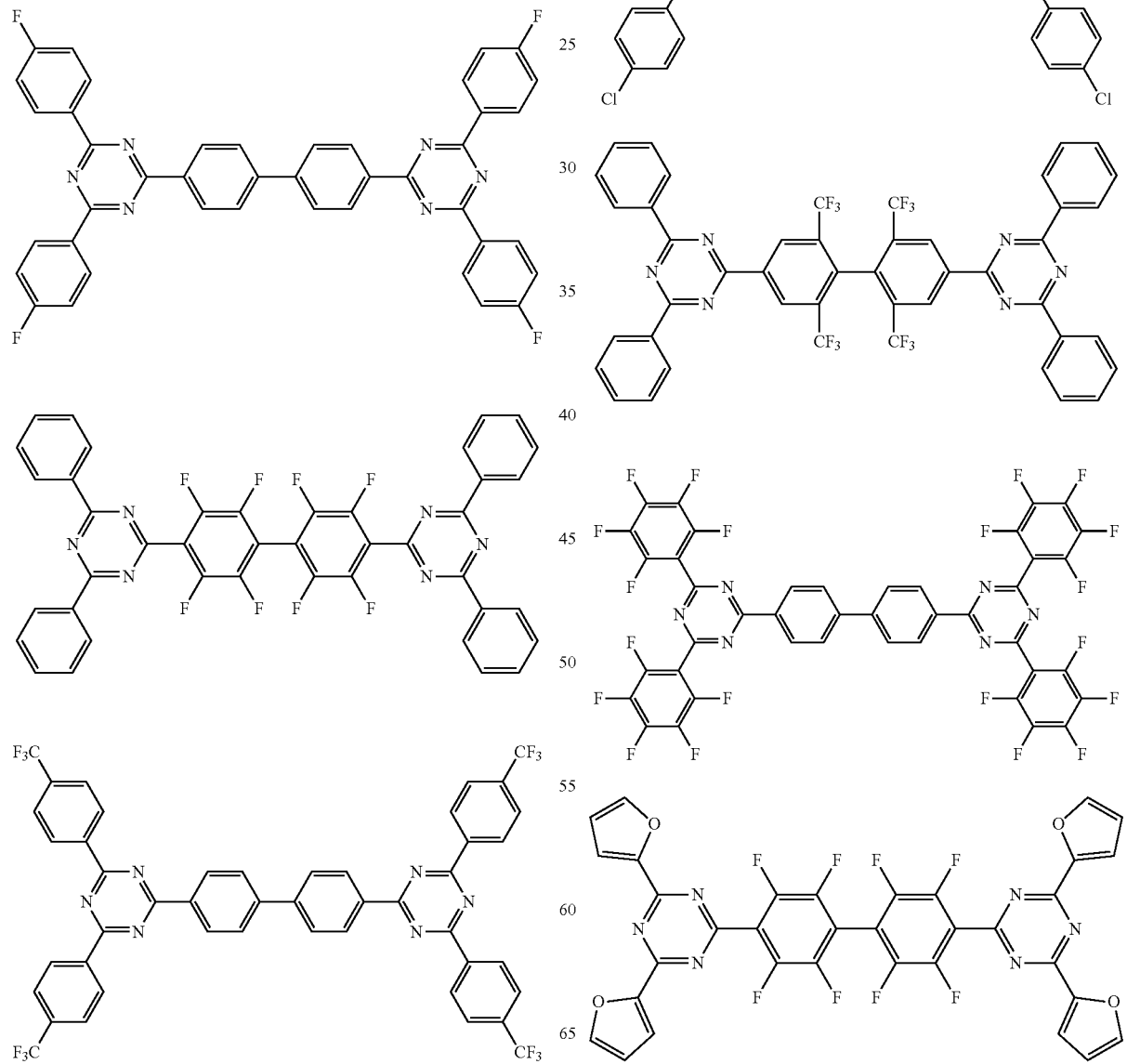

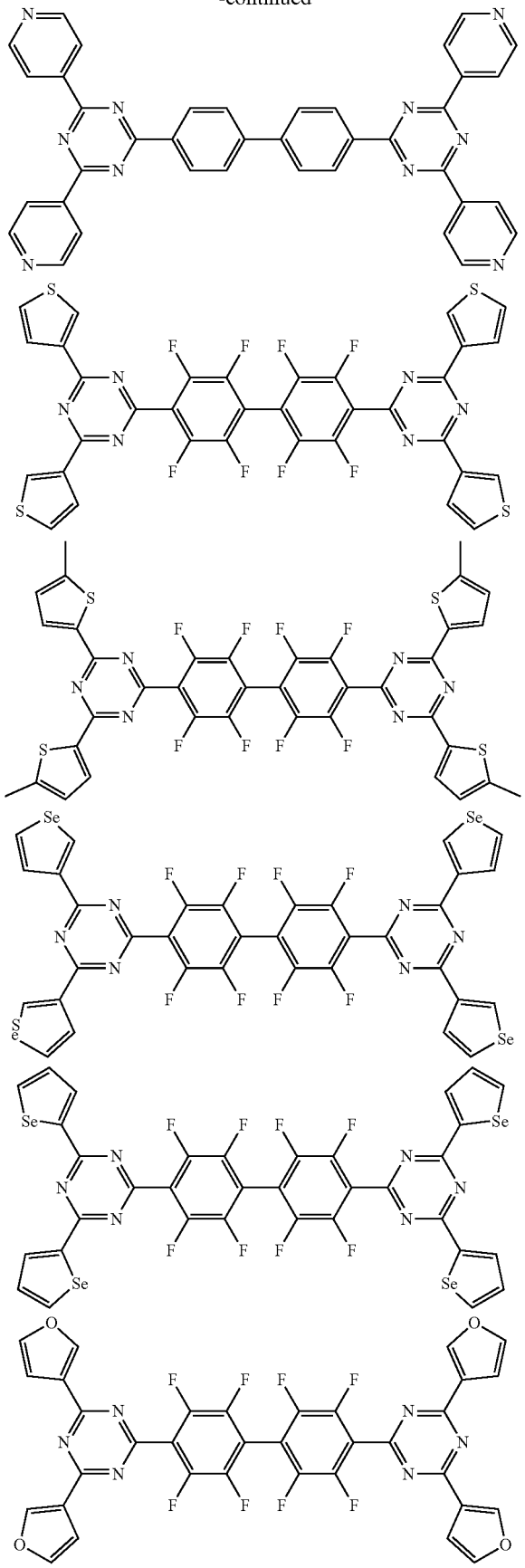
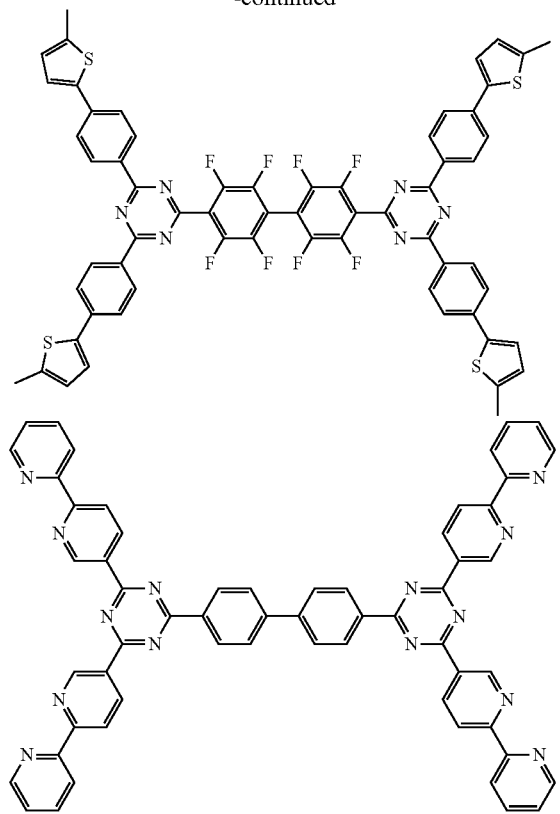

In addition, HOMO and LUMO levels of the transparent compound represented by General formula (3) or (4) are preferably levels at which the photoelectric conversion mechanism can be smoothly performed on the organic dye compound.

Specifically, in order for the transparent compound represented by General formula (3) or (4) to serve as the n type photoelectric conversion material and the organic dye compound to serve as the p type photoelectric conversion material, it is preferable that the LUMO level of the transparent compound represented by General formula (3) or (4) be lower than the LUMO level of the organic dye compound.

Here, as the photoelectric conversion mechanism in the photoelectric conversion film according to the second embodiment of the present disclosure, the following mechanism is specifically considered. That is, when the organic dye compound serving as the p type photoelectric conversion material absorbs light to excite and excited electrons move to the transparent compound that serves as the n type photoelectric conversion material and is represented by General formula (3) or (4), charge separation is performed. In this case, the LUMO level of the transparent compound represented by General formula (3) or (4) is preferably a level at which excited electrons in the organic dye compound can move to the transparent compound represented by General formula (3) or (4) smoothly.

Specifically, it is preferable that a difference between the LUMO level of the transparent compound represented by General formula (3) or (4) and the LUMO level of the organic dye compound represented by General formula (1) be greater than or equal to 0.1 eV and less than or equal to 1.0 eV.

For example, when the quinacridone derivative represented by the following General formula (1) is used as the organic dye compound, in consideration of the LUMO level of the quinacridone derivative, the LUMO level of the transparent compound represented by General formula (3) or (4) is preferably greater than or equal to −4.8 eV and less than or equal to −3.5 eV, and more preferably, greater than or equal to −4.5 eV and less than or equal to −3.8 eV.

In addition, the HOMO level of the transparent compound represented by General formula (3) or (4) is preferably, for example, greater than or equal to −7.8 eV and less than or equal to −6.5 eV, and more preferably, greater than or equal to −7.5 eV and less than or equal to −6.8 cV.

Here, as a compound having the same hexaazatriphenylene skeleton as the transparent compound represented by General formula (3), for example, hexaazatriphenylenehexacarbonitrile (HAT-CN) represented by the following structural formula can be exemplified.

[Chem.18]

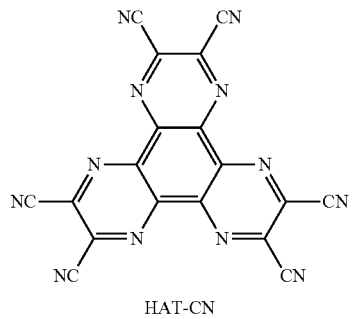

HAT-CN

HAT-CN is, for example, a compound that is used as a charge transport material in an organic electroluminescence element. However, since HAT-CN has an LUMO level of about −5.58 eV, it has a great difference from the LUMO level of the organic dye compound forming the bulk hetero mixed film in the photoelectric conversion film. Accordingly, in the photoelectric conversion film, when HAT-CN is used as the n type photoelectric conversion material, it is difficult to move excited electrons smoothly at an interface between HAT-CN and the organic dye compound.

Therefore, in the transparent compound included in the photoelectric conversion film according to the second embodiment of the present disclosure, among compounds having a structure represented by General formula (3) or (4), a compound having an LUMO level that is relatively close to that of the organic dye compound forming the bulk hetero mixed film is preferable. Specifically, it is preferable that the transparent compound represented by General formula (3) or (4) have a structure that has a difference of greater than or equal to 0.1 eV and less than or equal to 1.0 eV of the LUMO level from the organic dye compound.

As described above, when the photoelectric conversion film according to the second embodiment of the present disclosure includes the organic dye compound and the transparent compound represented by General formula (3) or (4), it is possible to selectively perform photoelectric conversion on light that is absorbed by the organic dye compound. For example, when the quinacridone derivative represented by General formula (1) is used as the organic dye compound, the photoelectric conversion film according to the second embodiment of the present disclosure can selectively perform photoelectric conversion on green light (for example, light having a wavelength of greater than or equal to 450 nm and less than 600 nm).

In addition, since the transparent compound represented by General formula (3) or (4) has a high electron mobility and can form the bulk hetero mixed film with the organic dye compound with high charge separation efficiency, it is possible to increase photoelectric conversion efficiency of the photoelectric conversion film. Accordingly, the photoelectric conversion film according to the second embodiment of the present disclosure can be appropriately used for the photoelectric conversion film of the solid-state image sensor and it is possible to increase sensitivity of the solid-state image sensor.

(3.2. Configuration of Photoelectric Conversion Element According to Second Embodiment)

Since a configuration of the photoelectric conversion element according to the second embodiment of the present disclosure is substantially the same as the configuration described in the first embodiment of the present disclosure, detailed description thereof will be omitted.

That is, the photoelectric conversion element according to the second embodiment of the present disclosure is different from the first embodiment in that the photoelectric conversion layer 108 is configured as the photoelectric conversion film including the transparent compound represented by General formula (3) or (4).

(3.3. Example According to Second Embodiment)

Hereinafter, the photoelectric conversion film according to the second embodiment of the present disclosure will be described in detail with reference to examples and comparative examples. However, the following examples are only examples and the photoelectric conversion film according to the second embodiment of the present disclosure are not limited to the following examples.

(Manufacturing of Photoelectric Conversion Clement)

In addition, the photoelectric conversion element according to the second embodiment of the present disclosure was manufactured by the following manufacturing methods. However, structures and manufacturing methods of photoelectric conversion elements to be described below are only examples. The structure and the manufacturing method of the photoelectric conversion element according to the second embodiment of the present disclosure are not limited to the following examples.

Example 8

First, a glass substrate with an ITO electrode was washed by UV/ozone treatment. In addition, a film thickness of an ITO film corresponding to a lower electrode in the glass substrate was 50 nm. Next, the glass substrate was put into an organic deposition apparatus, a pressure was decreased to less than or equal to $1 \times 10^{-4}$ Pa, and 5,6,11,12,17,18-hexaazatrinaphthylene (HATNA) represented by the following structural formula and quinacridone was deposited by the resistance heating method while rotating a substrate holder. In addition, deposition was performed at a deposition rate of 0.1 nm/sec such that a ratio of HATNA and quinacridone became 1:1, and a film of 100 nm in total was formed to form the photoelectric conversion layer. HATNA is a transparent compound that has a structure represented by General formula (3).

Further, a film of AlSiCu was formed above the photoelectric conversion layer at a film thickness of 100 nm by the deposition method to form an upper electrode. By the above manufacturing method, the photoelectric conversion element including a photoelectric conversion area of 1 mm×1 mm was manufactured.

[Chem.19]

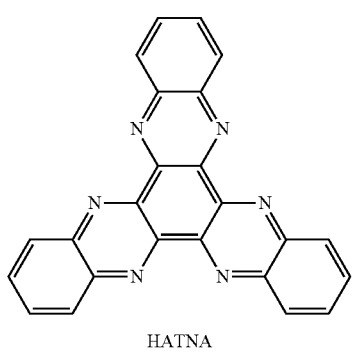

HATNA

Example 9

A photoelectric conversion element was manufactured by the same method as in Example 8 except that 2,3,8,9,14,15-hexachloro-5,6,11,12,17,18-hexaazatrinaphthylene (Cl6-HATNA) represented by the following structural formula was used instead of HATNA used in Example 8. Cl6-HATNA is a transparent compound that has a structure represented by General formula (3).

[Chem.20]

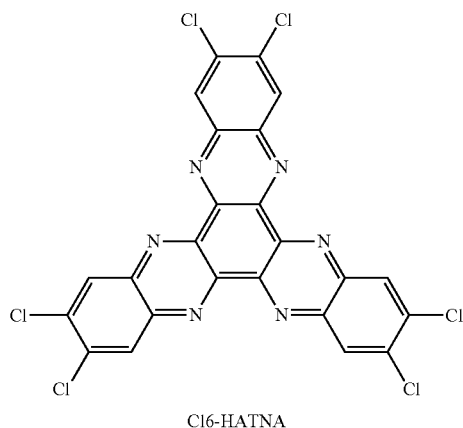

Cl6-HATNA

Example 10

A photoelectric conversion element was manufactured by the same method as in Example 8 except that 4,4'-bis(4,6-diphenyl-1,3,5-triazin-2-yl)biphenyl (BTB) represented by the following structural formula was used instead of HATNA used in Example 8. BTB is a transparent compound that has a structure represented by General formula (4).

[Chem. 21]

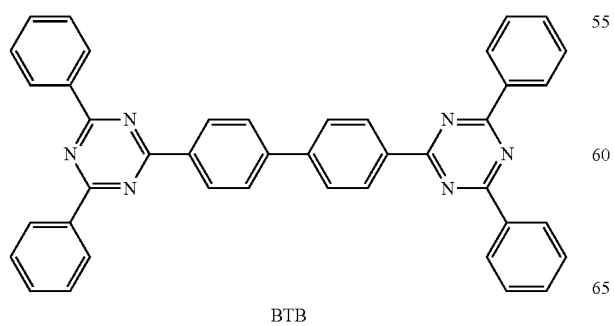

BTB

Comparative Example 16

A photoelectric conversion element was manufactured by the same method as in Example 8 except that a photoelectric conversion layer was formed at a film thickness of 100 nm using only quinacridone instead of using HATNA and quinacridone used in Example 8.

Comparative Example 17

A photoelectric conversion element was manufactured by the same method as in Example 8 except that 4,6-bis(3,5-di(pyridin-4-yl)phenyl)-2-methyl pyrimidine (B4PyMPM) represented by the following structural formula was used instead of HATNA used in Example 8. In addition, B4PyMPM is a transparent compound having a value of an LUMO level that is close to an LUMO level of HATNA.

[Chem. 22]

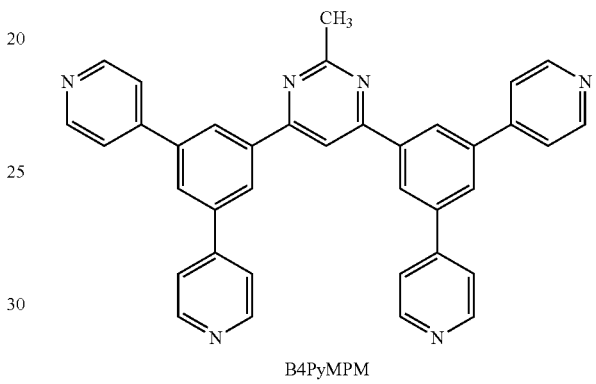

B4PyMPM

Comparative Example 18

A photoelectric conversion element was manufactured by the same method as in Example 8 except that a photoelectric conversion layer was formed at a film thickness of 100 nm using only subphthalocyanine chloride (SubPc-Cl) represented by the following structural formula instead of HATNA and quinacridone used in Example 8. In addition, SubPc-Cl is a compound having a value of an LUMO level that is close to an LUMO level of HATNA, but absorbs light of a visible light band.

[Chem. 23]

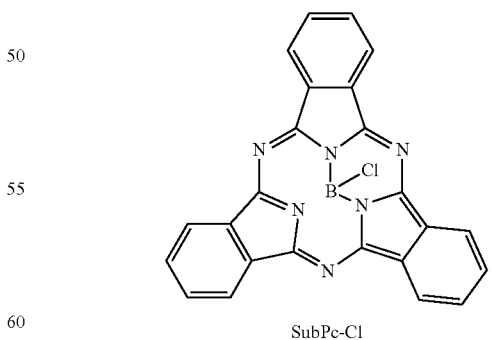

SubPc-Cl

Comparative Example 19

A photoelectric conversion element was manufactured by the same method as in Example 8 except that SubPc-Cl was used instead of HATNA used in Example 8.

In addition, in the above example, as quinacridone and SubPc-Cl, sublimated and purified products purchased from Tokyo Chemical Industry Co., Ltd. were used. In addition, as HATNA, Cl6-HATNA and BTB, sublimated and purified products purchased from Lumtec Corp. (Taiwan) were used.

(Evaluation of Optical Conversion Characteristics)

First, photoelectric conversion efficiency and spectral characteristics were evaluated for the above manufactured photoelectric conversion elements according to Examples 8 to 10 and Comparative examples 16 to 19.

Here, photoelectric conversion efficiency was evaluated by measuring external quantum efficiency using the semiconductor parameter analyzer. Specifically, light having a wavelength of 565 nm was radiated to the photoelectric conversion element at an intensity of 1.62 microwatts per square centimeter from a light source through a filter, and external quantum efficiency was computed from a light current value and a dark current value when the bias voltage applied between electrodes was set to −1 V.

In addition, spectral characteristics were evaluated using an incident photon to current conversion efficiency (IPCE) measuring device such that a change rate of external quantum efficiency with respect to a wavelength was measured and a full width at half maximum of a peak was computed. Specifically, light of 1.62 microwatts per square centimeter was radiated to the photoelectric conversion element from a light source through a filter, and external quantum efficiency was computed from a light current value and a dark current value when the bias voltage applied between electrodes was set to −1 V. In addition, the above external quantum efficiency was computed for each wavelength and a full width at half maximum of a peak was calculated.

The above evaluation results are shown in the following Table 4. In addition, IPCE measurement results of Example 8 and Comparative example 19 are shown in FIG. 4. In Table 4, "QD" represents quinacridone, and "—" represents that no corresponding material was added. FIG. 4 shows the graph of IPCE measurement results of Example 8 and Comparative example 19, a solid line represents Example 8 and a dashed line represents Comparative example 19.

TABLE 4

| | P type photoelectric conversion material | N type photoelectric conversion material | External quantum efficiency (%) | Full width at half maximum of peak (nm) |
|---|---|---|---|---|
| Example 8 | QD | HATNA | 43 | 130 |
| Example 9 | QD | C16-HATNA | 28 | 130 |
| Example 10 | QD | BTB | 37 | 130 |
| Comparative example 16 | QD | — | 9 | 135 |
| Comparative example 17 | QD | B4PyMPM | 2.3 | 140 |
| Comparative example 18 | SubPc-Cl | — | 3 | 165 |
| Comparative example 19 | QD | SubPc-Cl | 39 | 180 |

As shown in the results in Table 4, it can be understood that Examples 8 to 10 serving as the photoelectric conversion element according to the second embodiment of the present disclosure have significantly higher external quantum efficiency than Comparative examples 16 to 18.

Here, Comparative example 19 has high external quantum efficiency similar to Examples 8 to 10, but SubPc-Cl absorbing visible light was used as the n type photoelectric conversion material. For this reason, since a full width at half maximum of a peak according to IPCE measurement in Comparative example 19 is wider than those of Examples 8 to 10, it is not preferable. Specifically, as shown in FIG. 4, since a peak of a profile of external quantum efficiency with respect to a wavelength in Comparative example 19 is wider than a peak of Example 8, red light having a wavelength of greater than or equal to 600 nm or blue light having a wavelength of less than 450 nm can also be absorbed, it is not preferable.

On the other hand, as shown in FIG. 4, it can be understood that Example 8 has a sharper peak of a profile of external quantum efficiency with respect to a wavelength than Comparative example 19, and can absorb green light having a wavelength of greater than or equal to 450 nm and less than 600 nm more selectively, and perform photoelectric conversion. Accordingly, it can be understood that, since Example 8 has higher selectivity of a wavelength of light to be absorbed than Comparative example 19, it is appropriate for the photoelectric conversion element of the solid-state image sensor.

Subsequently, in Examples 8 to 10 and Comparative examples 16 to 19, HOMO levels and LUMO levels of the p type photoelectric conversion material and the n type photoelectric conversion material used in the photoelectric conversion layer were measured.

In addition, in order to measure the HOMO level, a sample in which each organic material was formed into a 20 nm film by the deposition method on a silicon substrate that had been treated with UV/ozone was used. The HOMO level was computed for the sample in which each organic material was formed into a film using the UPS method.

In addition, in order to measure the LUMO level, a sample in which each organic material was formed into a 50 nm film by the deposition method on a quartz substrate that had been treated with UV/ozone was used. First, a transmittance and a reflectance of the sample were measured and an absorption coefficient alpha with respect to a wavelength was computed. Next, an absorption end of a visible light area of the computed absorption coefficient alpha was computed as an HOMO-LUMO gap, and the HOMO-LUMO gap was subtracted from the HOMO level to compute the LUMO level.

The measured HOMO level and LUMO level of the p type photoelectric conversion material and the n type photoelectric conversion material are shown in the following Table 5. In Table 5, "QD" represents quinacridone.

TABLE 5

| | HOMO (eV) | LUMO (eV) |
|---|---|---|
| HATNA | −6.9 | −3.8 |
| C16-HATNA | −7.8 | −5.1 |
| BTB | −6.9 | −3.6 |
| B4PyMPM | −7.6 | −4.05 |
| SubPc-Cl | −5.7 | −3.7 |
| QD | −5.55 | −3.55 |

As shown in the results in Table 5, an LUMO level difference between "HATNA" and "QD" used in Example 8 is 0.25 eV. An LUMO level difference between "Cl6-HATNA" and "QD" used in Example 9 is 1.55 eV. An LUMO level difference between "BTB" and "QD" used in Example 10 is 0.05 eV. As shown in the results in Table 4, it can be understood that Example 8 has an LUMO level difference that is included in a preferable range (greater than or equal to 0.1 eV and less than or equal to 1.0 eV) in the second embodiment of the present disclosure and has higher external quantum efficiency than Examples 9 and 10 having LUMO level differences outside of the preferable range.

In addition, "B4PyMPM" used in Comparative example 17 is a transparent compound that has an LUMO level close to that of "HATNA" serving as the transparent material according to the second embodiment of the present disclosure. However, Comparative example 17 has significantly lower external quantum efficiency than Examples 8 to 10. Accordingly, it can be understood that, in the photoelectric conversion film according to the second embodiment of the present disclosure, it is important that the transparent compound have a structure represented by General formula (3) or (4) in order to increase external quantum efficiency.

Specifically, when the transparent compound represented by General formula (3) or (4) forms the bulk hetero mixed film with the organic dye compound, crystal fine particles of sizes that are appropriate for charge separation can be formed. Accordingly, external quantum efficiency is considered to increase in the photoelectric conversion film using the transparent compound represented by General formula (3) or (4). On the other hand, since "B4PyMPM" having no structure represented by General formula (3) or (4) is unable to form crystal fine particles of sizes that are appropriate for charge separation, it is considered difficult to increase external quantum efficiency.

(Detailed Examination of Transparent Compound Represented by General Formula (4))

Hereinafter, a more preferable structure of the transparent compound represented by General formula (4) was examined.

(Synthesis of Transparent Compound Represented by General Formula (4))

First, a synthesizing method of BTB-1 to BTB-6 that are the transparent compound represented by General formula (4) and represented by the following structure will be described. Purity of the synthesized BTB-1 to BTB-6 was examined using high performance liquid chromatography (HPLC), and $^1$HNMR and matrix assisted laser desorption/ionization-time of flight massspectrometry (MALDI-TOFMS) were used for identification. However, the following synthesizing method to be described is only an example, and the synthesizing method of the transparent compound represented by General formula (4) is not limited to the following example.

[Chem. 24]

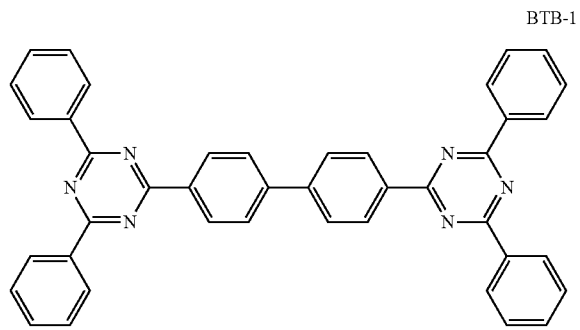
BTB-1

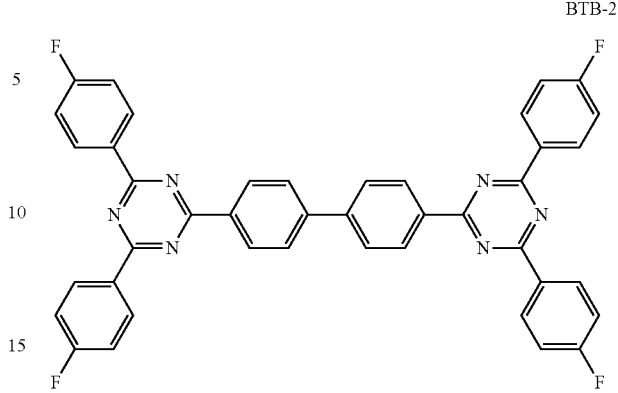
BTB-2

-continued

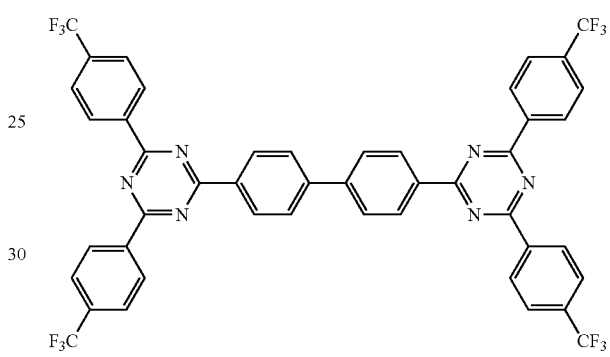
BTB-3

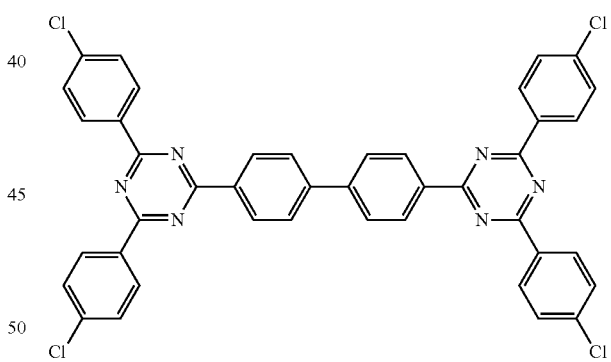
BTB-4

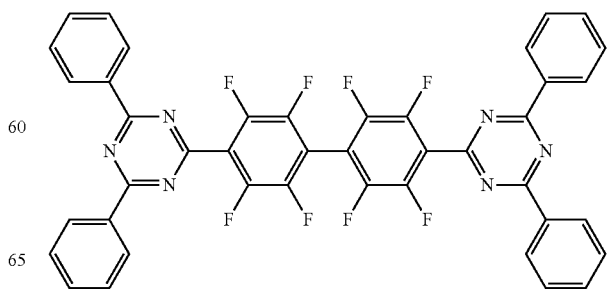
BTB-5

-continued

BTB-6

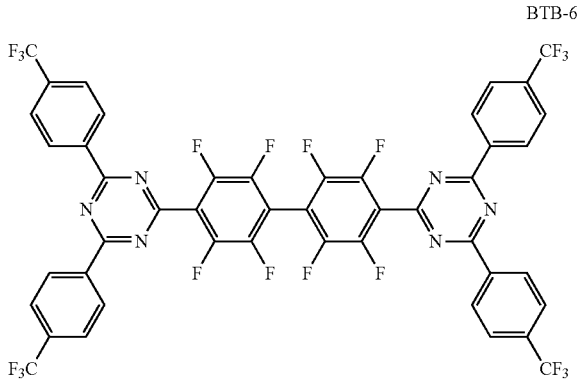 [SMILES: Fc1c(F)c(-c2c(F)c(F)c(-c3nc(-c4ccc(C(F)(F)F)cc4)nc(-c4ccc(C(F)(F)F)cc4)n3)c(F)c2F)c(F)c(F)c1-c1nc(-c2ccc(C(F)(F)F)cc2)nc(-c2ccc(C(F)(F)F)cc2)n1]

Synthesis of BTB-1
BTB-1 was synthesized through the following Reaction formula 5.

[Chem. 25]

Reaction formula (5)

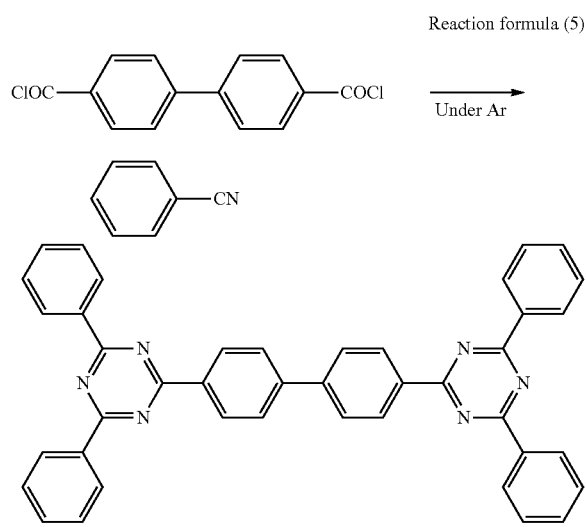

Biphenyl dicarbonyl dichloride (28.8 g, 103 mmol), thionyl chloride ($SOCl_2$) (8.43 g, 70.9 mmol), orthodichlorobenzene (405 mL), aluminum chloride (30.6 g, 230 mmol), and benzonitrile (61.1 g, 444 mmol) were added to a four-neck flask under an argon (Ar) atmosphere. The mixture was sufficiently stirred and then was heated and stirred for 30 minutes at 150 degrees Celsius. Subsequently, a temperature was decreased to 120 degrees Celsius, ammonium chloride (23.1 g, 432 mmol) was added, and the mixture was heated and stirred again for 4 hours at 170 degrees Celsius.

After a temperature was cooled to room temperature, a reaction solution was mixed with a solution in which 28% ammonia water (400 mL) and methanol (3 L) were mixed, and a precipitated solid was extracted by filtration. The precipitated solid was suspended and washed with pure water (1 L), and suspended and washed again with methanol (1 L) to obtain a gray solid. Additionally, the obtained gray solid was sublimated and purified twice to obtain BTB-1 (11.4 g, yield 18%) that is a target compound.

Synthesis of BTB-2
BTB-2 was synthesized by the same method as in the above Reaction formula 5 except that 4-fluoro-benzonitrile was used instead of benzonitrile.

Synthesis of BTB-3
BTB-3 was synthesized by the same method as in the above Reaction formula 5 except that 4-trifluoromethyl benzonitrile was used instead of benzonitrile.

Synthesis of BTB-4
BTB-4 was synthesized by the same method as in the above Reaction formula 5 except that 4-chloro-benzonitrile was used instead of benzonitrile.

Synthesis of BTB-5
BTB-5 was synthesized by the same method as in the above Reaction formula 5 except that tetra fluoro diphenyl carbonyl chloride was used instead of diphenyl carbonyl chloride.

Synthesis of BTB-6
BTB-6 was synthesized by the same method as in the above Reaction formula 5 except that tetra fluoro diphenyl carbonyl chloride was used instead of diphenyl carbonyl chloride and 4-chloro-benzonitrile was used instead of benzonitrile.

(Evaluation of Spectral Characteristics of Transparent Compound Represented by General Formula (4))

Next, a monolayer film sample of the transparent compound represented by General formula (4) was manufactured and spectral characteristics of the transparent compound represented by General formula (4) were identified.

Specifically, a sample in which each organic material (BTB-1 to BTB-6) was formed into a 50 nm film by the deposition method on a quartz substrate that had been treated with UV/ozone at a deposition rate of 0.05 nm/sec was manufactured. Next, a transmittance and a reflectance of the manufactured sample were measured by the spectrophotometer (JASCO V-570), and an absorption coefficient alpha with respect to a wavelength was computed. Measurement results of the absorption coefficient alpha are shown in FIG. 5. FIG. 5 shows the graph of the absorption coefficient alpha in a band of 300 nm to 800 nm of BTB-1 to BTB-6.

As shown in FIG. 5, it can be understood that all of BTB-1 to BTB-6 of the transparent compound represented by General formula (4) have a low absorption coefficient in a wavelength band of 400 nm to 800 nm. In other words, it can be understood that BTB-1 to BTB-6 of the transparent compound represented by General formula (4) are transparent compounds that do not absorb light of a visible light band.

(Evaluation of Electrical Characteristics of Transparent Compound Represented by General Formula (4))

Subsequently, a photoelectric conversion element was manufactured using the transparent compound represented by General formula (4) and electrical characteristics of the photoelectric conversion element were evaluated.

Example 11

First, a glass substrate with an ITO electrode was washed by UV/ozone treatment. In addition, a film thickness of an ITO film corresponding to a lower electrode in the glass substrate was 50 nm. Next, the glass substrate was put into an organic deposition apparatus, a pressure was decreased to less than or equal to $1 \times 10^{-5}$ Pa, and the above synthesized BTB-1 and quinacridone (a sublimated and purified product manufactured by Tokyo Chemical Industry Co., Ltd.) were deposited by the resistance heating method while rotating a substrate holder. In addition, deposition was performed at a deposition rate of 0.03 nm/sec and 0.07 nm/sec such that a ratio of BTB-1 and quinacridone became 3:7, and a film of 120 nm in total was formed to form the photoelectric conversion layer.

Subsequently, a film of LiF of 0.5 nm was deposited and formed above the photoelectric conversion layer at 0.002 nm/sec, and further a film of AlSiCu was formed at a film thickness of 100 nm by the deposition method to form an upper electrode. By the above method, the photoelectric conversion element including a photoelectric conversion area of 1 mm×1 mm was manufactured.

Examples 12 to 16

A photoelectric conversion element was manufactured by the same method as in Example 11 except that BTB-2 to BTB-6 were used instead of BTB-1 used in Example 11.

Comparative Example 20

A photoelectric conversion element was manufactured by the same method as in Example 11 except that quinacridone was used instead of BTB-1 used in Example 11 and only quinacridone was used to form the photoelectric conversion layer.

Photoelectric conversion efficiency was evaluated for the above manufactured photoelectric conversion elements according to Examples 11 to 16 and Comparative example 20. Here, photoelectric conversion efficiency was evaluated by measuring external quantum efficiency using the semiconductor parameter analyzer. Specifically, light was radiated to the photoelectric conversion element at an intensity of 1.62 microwatts per square centimeter from a light source through a filter, and external quantum efficiency was computed from a light current value and a dark current value when the bias voltage applied between electrodes was set to −1 V.

Evaluation results are shown in the following Table 6. In Table 6, "QD" represents quinacridone and "-" represents that no corresponding material was added.

In addition, external quantum efficiency was evaluated before and after annealing treatment. The annealing treatment was performed by heating the photoelectric conversion element using a hot plate in a glove box. Here, a heating temperature was 160 degrees Celsius and a heating time was 210 minutes.

and after annealing, BTB-1 to BTB-6 of the transparent compound represented by General formula (4) have a high heat resistance.

Further, comparing Example 11 and Examples 12 to 16, it can be understood that Examples 12 to 16 using BTB-2 to BTB-6 including an electron attracting group as a substituent have higher external quantum efficiency than Example 11 using BTB-1 including no electron attracting group as a substituent. Accordingly, it is understood that the transparent compound represented by General formula (4) preferably includes an electron attracting group as a substituent. Specifically, it can be understood in General formula (4) that at least one of substituents of $Ar_1$ to $Ar_4$ and $R_{41}$ to $R_{48}$ is preferably the electron attracting group.

As can be understood from the above results, when the photoelectric conversion element according to the second embodiment of the present disclosure includes the transparent compound represented by General formula (3) or (4), it is possible to increase photoelectric conversion efficiency while selectively absorbing light of a specific wavelength. Accordingly, since the photoelectric conversion element according to the second embodiment of the present disclosure can be appropriately used as the photoelectric conversion element in the solid-state image sensor, it is possible to increase sensitivity of the solid-state image sensor.

4. Third Embodiment (4.1. Configuration of Photoelectric Conversion Element According to Third Embodiment)

Next, the photoelectric conversion element according to the third embodiment of the present disclosure will be described. The photoelectric conversion element according to the third embodiment of the present disclosure is a photoelectric conversion element that includes a hole blocking layer and a difference between an ionization potential of the hole blocking layer and a work function of an electrode that is adjacent to the hole blocking layer is greater than or equal to 2.3 eV.

Specifically, same as the first embodiment of the present disclosure, a photoelectric conversion element according to the third embodiment of the present disclosure includes a substrate 102, a lower electrode 104 disposed above the substrate 102, an electron blocking layer 106 disposed above the lower electrode 104, a photoelectric conversion layer

TABLE 6

| | P type photoelectric conversion material | N type photoelectric conversion Material | Before annealing | | After annealing | |
|---|---|---|---|---|---|---|
| | | | External quantum efficiency (%) | Dark current (A/cm$^2$) | External quantum efficiency (%) | Dark current (A/cm$^2$) |
| Example 11 | QD | BTB-1 | 21 | $1.40 \times 10^{-9}$ | 20 | $9.40 \times 10^{-10}$ |
| Example 12 | QD | BTB-2 | 34 | $8.85 \times 10^{-10}$ | 31 | $4.20 \times 10^{-10}$ |
| Example 13 | QD | BTB-3 | 37 | $8.40 \times 10^{-10}$ | 52 | $3.00 \times 10^{-10}$ |
| Example 14 | QD | BTB-4 | 33 | $1.20 \times 10^{-9}$ | 33 | $4.60 \times 10^{-10}$ |
| Example 15 | QD | BTB-5 | 34 | $9.60 \times 10^{-10}$ | 31 | $4.90 \times 10^{-10}$ |
| Example 16 | QD | BTB-6 | 41 | $7.50 \times 10^{-10}$ | 45 | $4.20 \times 10^{-10}$ |
| Comparative example 20 | QD | — | 8 | $1.40 \times 10^{-9}$ | 6 | $9.90 \times 10^{-10}$ |

As shown in the results in Table 6, it can be understood that Examples 11 to 16 have higher external quantum efficiency than Comparative example 20. In addition, it can be understood that, since Examples 11 to 16 have external quantum efficiency that is not significantly decreased before 108 disposed above the electron blocking layer 106, a hole blocking layer 110 disposed above the photoelectric conversion layer 108, and an upper electrode 112 disposed above the hole blocking layer 110. In addition, in the photoelectric conversion element according to the third embodiment of the present disclosure, the difference between the ionization potential of the hole blocking layer 110 and the work function of the upper electrode 112 is greater than or equal to 2.3 eV. In addition, the ionization potential of the hole blocking layer 110 corresponds to an absolute value of energy of the HOMO level of the compound forming the hole blocking layer 110.

In general, in the photoelectric conversion element used in the solid-state image sensor, in many cases, in order to increase sensitivity, a voltage is applied from the outside to increase photoelectric conversion efficiency and a response speed. However, when the voltage is applied to the photoelectric conversion element from the outside, since the number of holes and electrons introduced from the electrode due to an external electric field increases, regardless of incidence of light, a flowing dark current increases. In the photoelectric conversion element used in the solid-state image sensor, in order to extract a difference between a dark current when no light is incident and a light current when light is incident as a signal, when the dark current is increased, an S/N ratio may decrease.

In particular, when a temperature of a usage environment is high (for example, greater than or equal to 50 degrees Celsius), since the dark current flowing in the photoelectric conversion element increases according to an increase in the temperature, it is necessary to suppress the dark current.

In the photoelectric conversion element according to the third embodiment of the present disclosure, by use of the hole blocking layer in which the difference between the ionization potential of the hole blocking layer and the work function the adjacent electrode is greater than or equal to 2.3 eV, it is possible to suppress the dark current. In particular, in the photoelectric conversion element according to the third embodiment of the present disclosure, even in a high temperature environment (for example, greater than or equal to 50 degrees Celsius), it is possible to suppress the dark current from increasing.

In addition, it is preferable that an energy difference between the ionization potential (that is, an absolute value of the HOMO level of the compound forming the hole blocking layer 110) of the hole blocking layer 110 and the work function of the adjacent electrode be higher. Accordingly, an upper limit of the energy difference between the ionization potential of the hole blocking layer 110 and the work function of the adjacent electrode is not particularly limited, but may be, for example, less than or equal to 3.0 eV.

For example, when the upper electrode 112 adjacent to the hole blocking layer 110 is formed of indium tin oxide (ITO) that is a transparent conductive material, since a work function of the indium tin oxide is 4.8 eV, the HOMO level of the compound forming the hole blocking layer 110 is preferably less than or equal to −6.8 eV, and more preferably, less than or equal to −7.1 eV.

In addition, the upper electrode 112 adjacent to the hole blocking layer 110 may be formed of a conductive material, but the material forming the upper electrode 112 is not limited to the above indium tin oxide. For example, the upper electrode 112 may be formed of a transparent conductive material, and may be formed of indium zinc oxide (IZO), a graphene transparent electrode or the like.

In addition, the LUMO level of the compound forming the hole blocking layer 110 is preferably the same as or shallower (an absolute value is smaller) than that of the n type photoelectric conversion material of the adjacent photoelectric conversion layer 108. In this case, the hole blocking layer 110 can efficiently move electrons generated in the photoelectric conversion layer 108 due to photoelectric conversion to the upper electrode 112. In addition, in order to more efficiently move electrons generated in the photoelectric conversion layer 108 to the upper electrode 112, it is preferable that a difference between the LUMO level of the compound forming the hole blocking layer 110 and the LUMO level of the n type photoelectric conversion material of the adjacent photoelectric conversion layer 108 be smaller.

For example, when the n type photoelectric conversion material included in the photoelectric conversion layer 108 is the subphthalocyanine derivative, the LUMO level of the compound forming the hole blocking layer 110 is preferably greater than or equal to −5.5 eV and less than or equal to −3.3 eV, and more preferably, greater than or equal to −5.0 eV and less than or equal to −3.5 eV.

Further, a film thickness of the hole blocking layer 110 is preferably greater than or equal to 1 nm and less than or equal to 50 nm, more preferably greater than or equal to 2 nm and less than or equal to 30 nm, and most preferably greater than or equal to 5 nm and less than or equal to 10 nm. When a film thickness of the hole blocking layer 110 is within the above range, the hole blocking layer 110 can efficiently move electrons from the photoelectric conversion layer 108 to the upper electrode 112 while suppressing holes from being introduced from the upper electrode 112.

Here, it is preferable that the hole blocking layer 110 include the compound represented by the following General formula (5).

[Chem. 26]

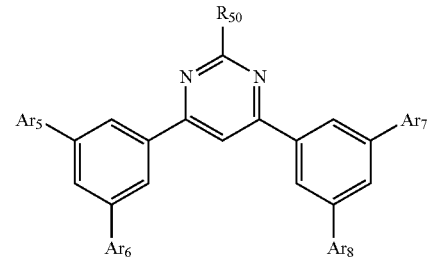

General formula (5)

In General Formula (5) above, $R_{50}$ represents any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, and $Ar_5$ to $Ar_8$ represent a substituted or unsubstituted heteroaryl group.

The compound represented by the above General formula (5) has a deep HOMO level (an absolute value of energy of the HOMO level is high) and a high ionization potential. Accordingly, in the compound represented by General formula (5), it is possible to set a difference between the ionization potential of the hole blocking layer 110 and a work function of the adjacent upper electrode 112 to greater than or equal to 2.3 eV. Therefore, the hole blocking layer 110 can suppress holes from being introduced from the upper electrode 112 due to an external electric field and it is possible to suppress the dark current even in a high temperature environment.

In addition, in General formula (5), it is preferable that at least one of substituents of $Ar_5$ to $Ar_5$ and $R_{50}$ be an electron attracting group. In other words, the compound represented by General formula (5) preferably has at least one electron attracting group as the substituent. In this case, in the compound represented by General formula (5), since the HOMO level becomes deeper (an absolute value increases) and the ionization potential increases, a difference from a work function of the adjacent upper electrode 112 can become greater. Since the hole blocking layer 110 including the compound represented by General formula (5) can further suppress holes from being introduced from the upper electrode 112, it is possible to further suppress the dark current.

In addition, in order to set the HOMO level of the compound represented by General formula (5) to a deeper value, it is preferable that the compound represented by General formula (5) include more electron attracting groups and it is preferable that an electron withdrawing ability of the substituent to be included be set to be higher. In this case, since the compound represented by General formula (5) can further suppress holes from being introduced from the upper electrode 112, it is possible to further suppress the dark current.

In the above description, the electron attracting groups may be, for example, a halogen, a cyano group, a nitro group, a sulfonyl group, an arylsulfonyl group, an alkylsulfonyl group, an acyl group, an acylamino group, an acyloxy group, an imide group, a carboxy group, a carboxamido group, a carboalkoxy group, a halogenated alkyl group, and a halogenated aryl group.

As a preferable specific example of the compound represented by General formula (5) above, a compound represented by the following structural formula can be exemplified. However, the compound represented by General formula (5) according to the third embodiment of the present disclosure is not limited to the following exemplary compounds.

[Chem. 27]

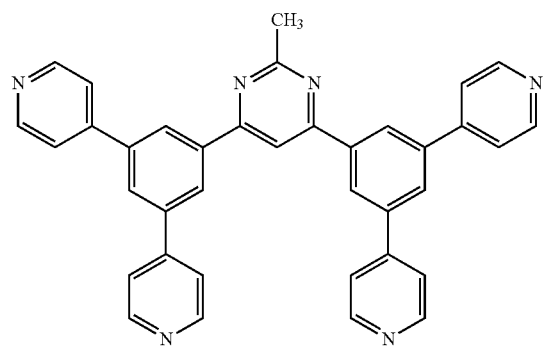

-continued

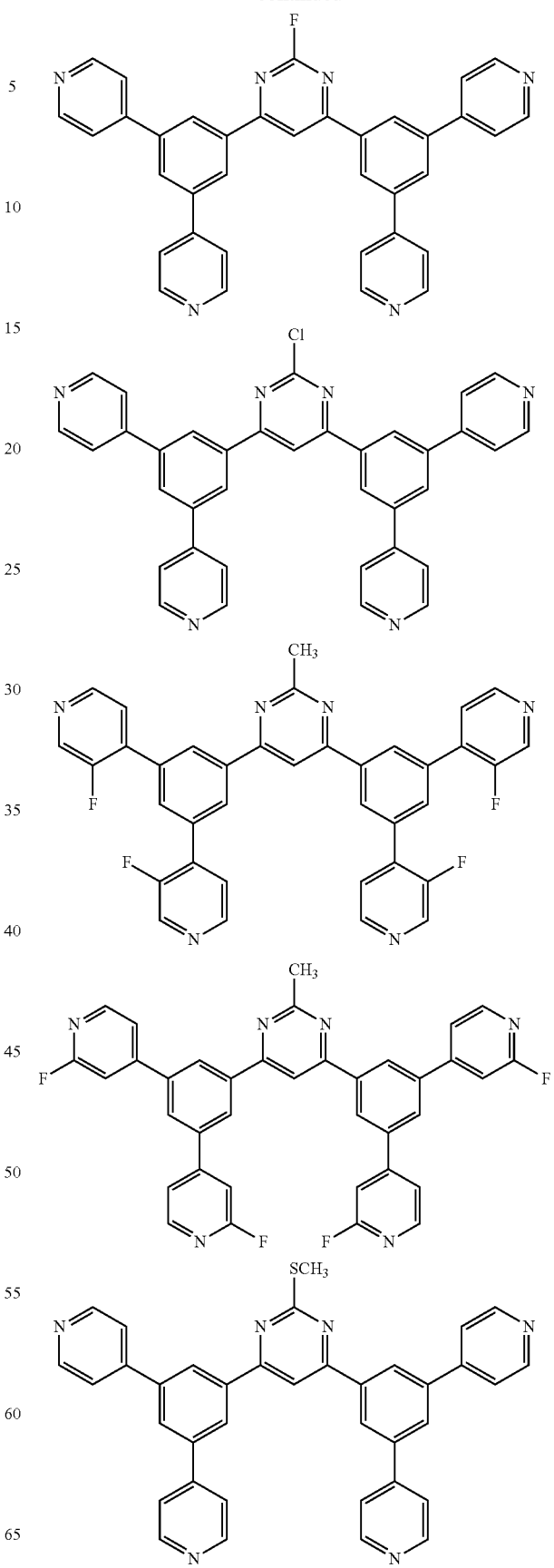

-continued

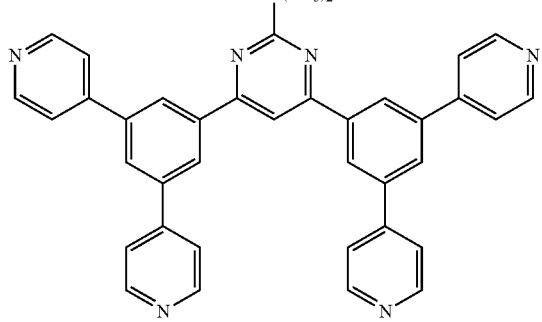

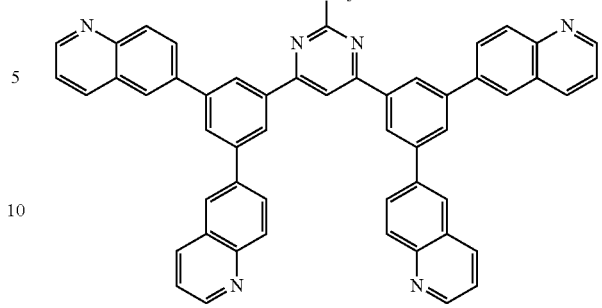

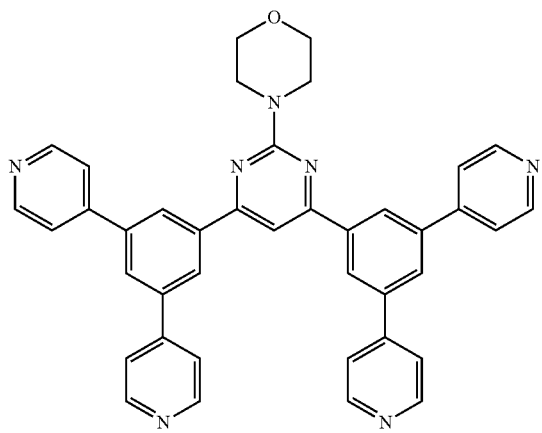

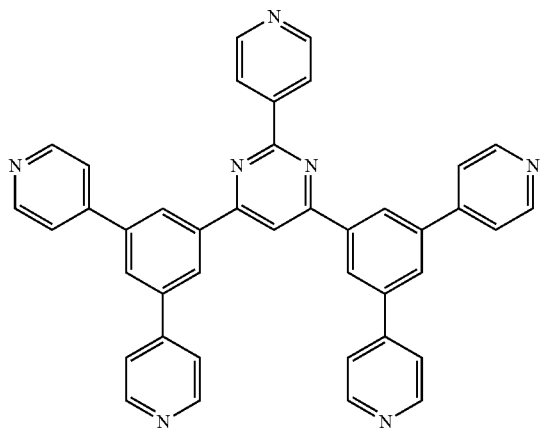

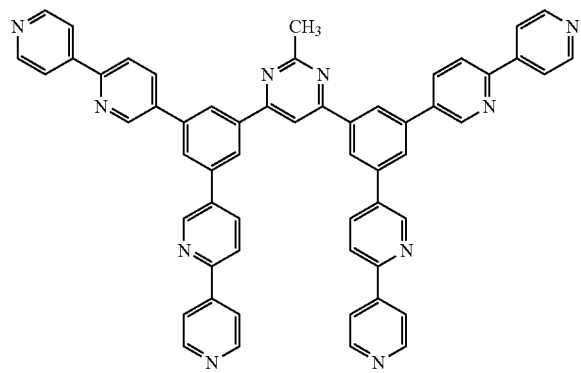

In addition, in the photoelectric conversion element according to the third embodiment of the present disclosure, since a configuration of the substrate 102, the lower electrode 104, the electron blocking layer 106, the photoelectric conversion layer 108 and the upper electrode 112 is substantially the same as that of the first embodiment, detailed description thereof will be omitted. However, the photoelectric conversion layer 108 is preferably formed in the above-described photoelectric conversion film according to the first and second embodiments.

As described above, the photoelectric conversion element according to the third embodiment of the present disclosure is possible to suppress the dark current when a hole blocking layer having an ionization potential that has a difference of greater than or equal to 2.3 eV from the work function of the adjacent electrode is used, In particular, in the photoelectric conversion element according to the third embodiment of the present disclosure, even in a high temperature environment (for example, greater than or equal to 50 degrees Celsius), it is possible to suppress the dark current from increasing.

In addition, in the photoelectric conversion element according to the third embodiment of the present disclosure, when the compound represented by General formula (5) is used in the hole blocking layer, it is possible to set an energy difference between the ionization potential of the hole blocking layer and the work function of the adjacent electrode to greater than or equal to 2.3 eV. Accordingly, in the photoelectric conversion element according to the third embodiment of the present disclosure, it is possible to suppress the dark current while maintaining high photoelectric conversion efficiency.

(4.2. Example According to Third Embodiment)

Hereinafter, the photoelectric conversion film according to the third embodiment of the present disclosure will be described in detail with reference to examples and comparative examples. However, the following examples are only examples and the photoelectric conversion film according to the third embodiment of the present disclosure are not limited to the following examples.

(Synthesis of Compound Represented by General Formula (5))

First, a synthesizing method of the compound represented by General formula (5) will be described. Specifically, B4PyMPM and B3PyMPM represented by the following structural formulae were synthesized. The synthesized B4PyMPM and B3PyMPM were identified using $^1$HNMR and FD-MS. However, the synthesizing method to be described below is only an example, and the synthesizing method of the compound represented by General formula (5) is not limited to the following example.

[Chem. 28]

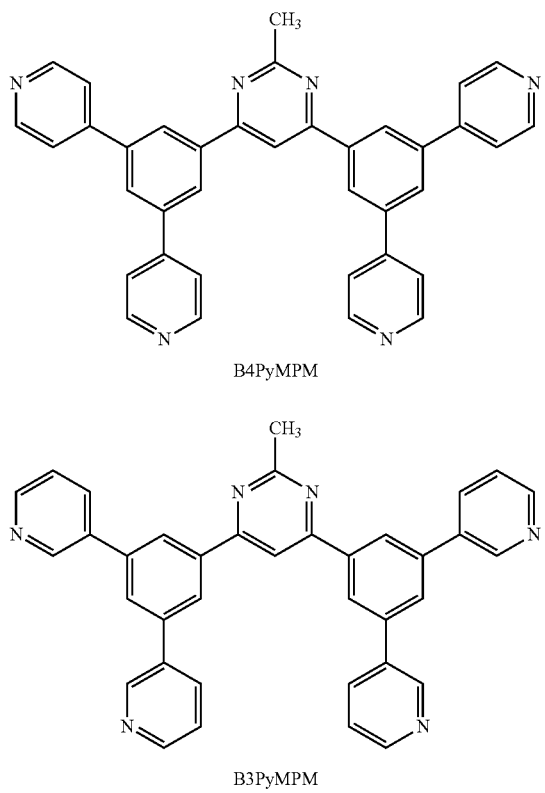

B4PyMPM

B3PyMPM

Synthesis of B4PyMPM

B4PyMPM was synthesized through the following reaction formulae 6 and 7.

[Chem. 29]

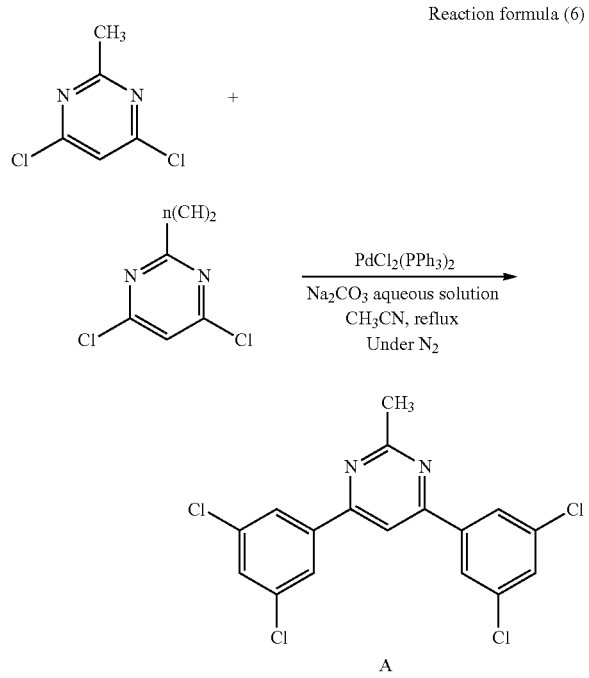

Reaction formula (6)

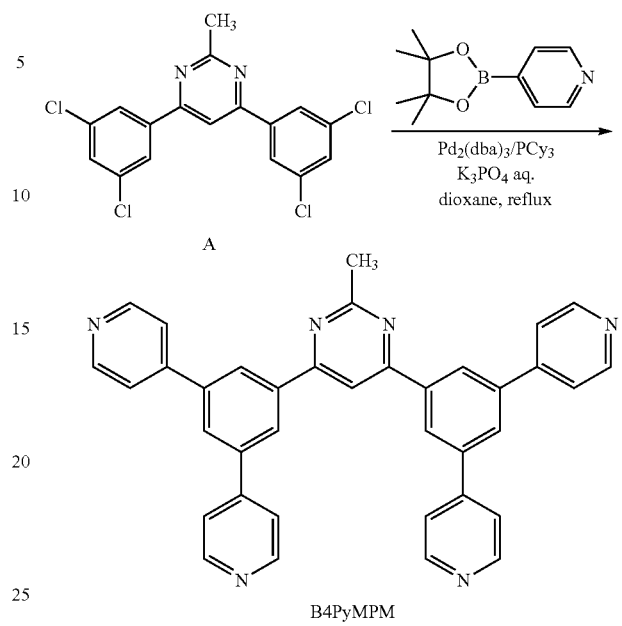

Reaction formula (7)

B4PyMPM

First, 4,6-dichloro-2-methyl-pyrimidine (5.0 g, 30.7 mmol), 3,5-dichlorophenyl boronic acid (12.9 g, 67.7 mmol), dichlorobis(triphenylphosphine)palladium(II) (PdCl$_2$ (PPh$_3$)$_2$) (1.07 g, 0.96 mmol), and a sodium carbonate aqueous solution (1.0 mol/L, 150 ml) were added to a three-neck flask under a nitrogen atmosphere, and the mixture was stirred for 10 minutes in an acetonitrile (500 ml) solvent. A reaction solution was mixed with water, and a precipitated solid was extracted by filtration. The precipitated solid was suspended and washed with pure water to obtain a white solid. Additionally, the obtained white solid was recrystallized to obtain an intermediate compound A (11.8 g, yield 72%).

Next, the intermediate compound A (4.6 g, 11.9 mmol), 4-pyridineboronic acid pinacol ester (10.8 g, 52.6 mmol), tris(dibenzylideneacetone)dipalladium(0) (Pd$_2$(dba)$_3$) (0.43 g, 0.48 mmol), tricyclohexylphosphine (PCy$_3$) (0.322 g, 1.15 mmol), and a potassium phosphate aqueous solution (1.35 mol/L, 138 ml) were added to a three-neck flask under a nitrogen atmosphere, and the mixture was stirred for 24 hours in a dioxane (440 ml) solvent. A reaction solution was mixed with water, and a precipitated solid was extracted by filtration. The precipitated solid was suspended and washed with pure water to obtain a white solid. Additionally, the obtained white solid was sublimated and purified to obtain B4PyMPM (6.67 g, yield 77%) that is a target compound.

Synthesis of B3PyMPM

In Reaction formula 7, B3PyMPM was synthesized by the same method as in Reaction formula 6 or 7 except that 3-pyridylboronic acid pinacol ester was used instead of 4-Pyridineboronic acid pinacol ester.

(Evaluation of Photoelectric Conversion Element)

In addition, the photoelectric conversion element according to the third embodiment of the present disclosure was manufactured by the following manufacturing methods. However, structures and manufacturing methods of photoelectric conversion elements to be described below are only examples. The structure and the manufacturing method of the photoelectric conversion element according to the third embodiment of the present disclosure are not limited to the following examples.

Example 17

First, a Si substrate with an ITO electrode was washed by UV/ozone treatment. In addition, a film thickness of an ITO film corresponding to a lower electrode in the Si substrate was 100 nm. Next, the Si substrate was put into an organic deposition apparatus, a pressure was decreased to less than or equal to $1\times10^{-5}$ Pa, and F6-SubPc-Cl (a sublimated and purified product manufactured) and t-butyl quinacridone (a sublimated and purified product manufactured by Tokyo Chemical Industry Co., Ltd.) were deposited by a resistance heating method while rotating a substrate holder. In addition, deposition was performed at a deposition rate of 0.05 nm/sec such that a ratio of F6-SubPc-Cl and t-butyl quinacridone (BQD) became 1:1, and a film of 120 nm in total was formed to form the photoelectric conversion layer.

Next, the above synthesized B4PyMPM was deposited above the photoelectric conversion layer by the resistance heating method. A deposition rate was 0.05 nm/sec, and a 5 nm film was formed to form the hole blocking layer. Subsequently, an ITO film was formed above the hole blocking layer by the sputtering method at a film thickness of 50 nm, thereby forming the upper electrode. In addition, the lower electrode and the upper electrode were formed to have a photoelectric conversion area of 0.5 mm×0.5 mm. Further, heat treatment of an element forming the upper electrode was performed for 3.5 hours at 160 degrees Celsius on a hot plate in a glove box replaced with nitrogen to manufacture the photoelectric conversion element. Hereinafter, structural formulae of F6-SubPc-Cl and t-butyl quinacridone (BQD) used in the photoelectric conversion layer will be illustrated.

[Chem. 30]

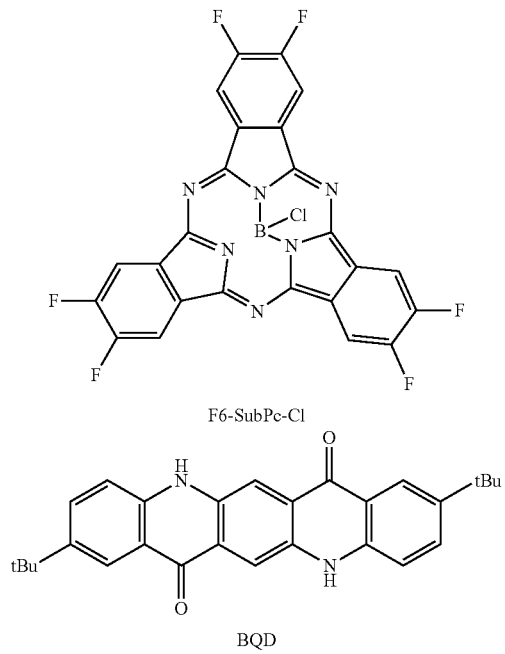

F6-SubPc-Cl

BQD

Example 18

A photoelectric conversion element was manufactured by the same method as in Example 17 except that the hole blocking layer was formed into a 10 nm film.

Example 19

A photoelectric conversion element was manufactured by the same method as in Example 17 except that the hole blocking layer was formed into a 20 nm film.

Example 20

A photoelectric conversion element was manufactured by the same method as in Example 17 except that the hole blocking layer was formed using B3PyMPM instead of B4PyMPM.

Example 21

A photoelectric conversion element was manufactured by the same method as in Example 17 except that the hole blocking layer was formed using HATNA represented by the following structural formula instead of B4PyMPM.

Example 22

A photoelectric conversion element was manufactured by the same method as in Example 17 except that the hole blocking layer was formed using Me6-HATNA represented by the following structural formula instead of B4PyMPM.

[Chem. 31]

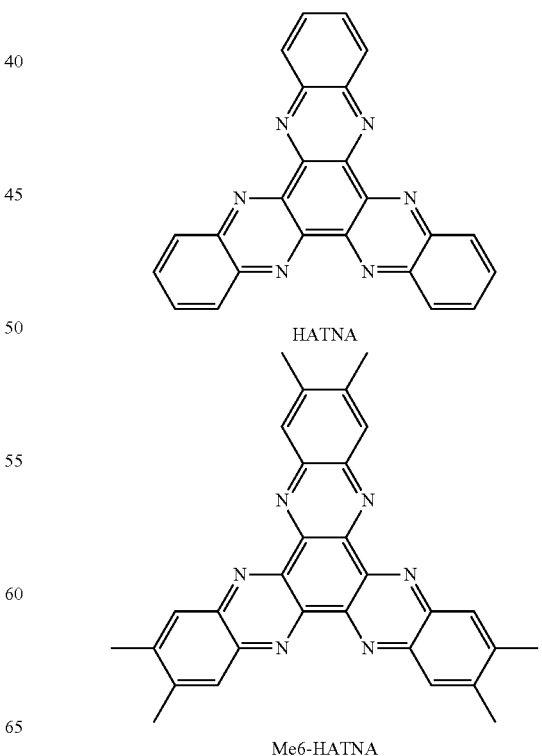

HATNA

Me6-HATNA

Comparative Example 23

A photoelectric conversion element was manufactured by the same method as in Example 17 except that no hole blocking layer was formed.
(Evaluation Result)
First, HOMO levels and LUMO levels of the compounds (B4PyMPM, B3PyMPM, HATNA, Me6-HATNA, F6-SubPc-Cl and BQD) used in each layer of the photoelectric conversion element according to Examples 17 to 20 and Comparative examples 21 to 23 were measured.

In addition, in order to measure the HOMO level, a sample in which each compound was formed into a 20 nm film by the deposition method on a silicon substrate that had been treated with UV/ozone was used. The HOMO level was computed for the sample in which each compound was formed into a film using the UPS method.

In addition, in order to measure the LUMO level, a sample in which each organic material was formed into a 50 nm film by the deposition method on a quartz substrate that had been treated with UV/ozone was used. First, a transmittance and a reflectance of the sample were measured and an absorption coefficient alpha with respect to a wavelength was computed. Next, an absorption end of a visible light area of the computed absorption coefficient alpha was computed as an HOMO-LUMO gap, and the HOMO-LUMO gap was subtracted from the HOMO level to compute the LUMO level.

The measured HOMO level and LUMO level of each compound are shown in the following Table 7. In addition, a work function of ITO used in the upper electrode was 4.8 eV.

TABLE 7

|  | HOMO (eV) | LUMO (eV) |
|---|---|---|
| B4PyMPM | −7.6 | −4.05 |
| B3PyMPM | −7.2 | −3.65 |
| HATNA | −6.9 | −3.8 |
| Me6-HATNA | −6.3 | −3.5 |
| F6-SubPc-Cl | −6.3 | 4.2 |
| BQD | −5.65 | −3.55 |

As shown in the results in Table 7, it can be understood that a difference between an ionization potential (an absolute value of the HOMO level) of B4PyMPM used in the hole blocking layer of Examples 17 to 19 and a work function of the upper electrode (ITO) is 2.8 eV and is included in a preferable range in the third embodiment of the present disclosure. In addition, it can be understood that a difference between an ionization potential of B3PyMPM used in the hole blocking layer of Example 20 and a work function of the upper electrode is 2.4 eV and is included in a preferable range in the third embodiment of the present disclosure.

On the other hand, it can be understood that a difference between an ionization potential of HATNA used in the hole blocking layer of Comparative example 21 and a work function of the upper electrode is 2.1 eV and is outside of a preferable range in the third embodiment of the present disclosure. In addition, it can be understood that a difference between an ionization potential of Me6-HATNA used in the hole blocking layer of Comparative example 22 and a work function of the upper electrode is 1.5 eV and is outside of a preferable range in the third embodiment of the present disclosure.

In addition, photoelectric conversion efficiency was evaluated for the above manufactured photoelectric conversion elements according to Examples 17 to 20 and Comparative examples 21 to 23. In addition, all evaluations of the photoelectric conversion elements according to Examples 17 to 20 and Comparative examples 21 to 23 were performed under a high temperature environment at 60 degrees Celsius.

Photoelectric conversion efficiency was evaluated by measuring external quantum efficiency using a semiconductor parameter analyzer. Specifically, light having a wavelength of 565 nm was radiated to the photoelectric conversion element from a light source at an intensity of 1.62 microwatts per square centimeter through a filter, and external quantum efficiency was computed from a light current value and a dark current value when the bias voltage applied between electrodes was set to −1 V or −5 V. Here, the condition in which the bias voltage applied between electrodes is set to −5 V may increase external quantum efficiency, but also increase the dark current.

The above evaluation results are shown in the following Table 8. In Table 8, "-" represents that no corresponding layer was formed. In addition, "energy difference" represents an energy difference between the ionization potential of the hole blocking layer and a work function of the upper electrode and was computed by obtaining a difference between an absolute value of the HOMO level of each compound forming the hole blocking layer and a work function (4.8 eV) of the upper electrode (ITO) formed by ITO.

TABLE 8

| | Hole blocking layer | | | Bias voltage −1 V | | Bias voltage −5 V | |
|---|---|---|---|---|---|---|---|
| | Compound | Energy difference (eV) | Film thickness (nm) | External quantum efficiency (%) | Dark current (A/cm²) | External quantum efficiency (%) | Dark current (A/cm²) |
| Example 17 | B4PyMPM | 2.8 | 5 | 48 | $5.0 \times 10^{-11}$ | 65 | $2.0 \times 10^{-10}$ |
| Example 18 | B4PyMPM | 2.8 | 10 | 47 | $4.0 \times 10^{-11}$ | 64 | $1.2 \times 10^{-10}$ |
| Example 19 | B4PyMPM | 2.8 | 20 | 45 | $3.0 \times 10^{-11}$ | 60 | $9.0 \times 10^{-11}$ |
| Example 20 | B3Py/MPM | 2.4 | 5 | 46 | $5.0 \times 10^{-11}$ | 62 | $3.0 \times 10^{-10}$ |
| Comparative example 21 | HATNA | 2.1 | 5 | 47 | $9.0 \times 10^{-11}$ | 64 | $4.7 \times 10^{-9}$ |
| Comparative example 22 | Me6-HATNA | 1.5 | 5 | 45 | $4.0 \times 10^{-10}$ | 60 | $6.1 \times 10^{-9}$ |
| Comparative example 23 | — | — | — | 45 | $1.8 \times 10^{-10}$ | 58 | $5.8 \times 10^{-9}$ |

As shown in the results in Tables 7 and 8, it can be understood that, in Examples 17 to 20 according to the third embodiment of the present disclosure, the dark current can be decreased at both of the bias voltages −1 V and −5 V, compared to Comparative example 23 in which no hole blocking layer was provided. In addition, it can be understood that Examples 17 to 20 can increase external quantum efficiency at both of the bias voltages −1 V and −5 V to the same or a greater extent than Comparative example 23. However, Example 19 in which the hole blocking layer was formed into a 20 nm film can decrease the dark current more than Examples 17 and 18, but has the same external quantum efficiency as Comparative example 23 in which no hole blocking layer was provided. Accordingly, it can be understood that a preferable film thickness of the hole blocking layer that can decrease the dark current and increase external quantum efficiency is less than or equal to 20 nm.

In addition, it can be understood that, in Comparative examples 21 and 22, since an energy difference between the ionization potential of the hole blocking layer and the work function of the upper electrode is outside of a preferable range in the third embodiment of the present disclosure, the dark current at the bias voltage −5 V increases compared to Examples 17 to 20, and it is not preferable.

Further, comparing Example 17 and Example 20, it can be understood that Example 17 can increase external quantum efficiency. The LUMO level of B4PyMPM used in the hole blocking layer of Example 17 is considered to be more preferable than the LUMO level of B3PyMPM used in the hole blocking layer of Example 20. Specifically, since the LUMO level (−4.05 eV) of B4PyMPM is closer to the LUMO level (−4.2 eV) of F6-SubPc-Cl used as the n type photoelectric conversion material of the photoelectric conversion layer than the LUMO level (−3.65 eV) of B3PyMPM, electrons generated by photoelectric conversion are considered to be more efficiently moved to the electrode. Accordingly, it is understood that the LUMO level of the compound used in the hole blocking layer is shallower (an absolute value is small) than the LUMO level of the n type photoelectric conversion material of the photoelectric conversion layer, and a difference with the LUMO level of the n type photoelectric conversion material is preferably small.

As can be understood from the above results, in the photoelectric conversion element according to the third embodiment of the present disclosure, when there is provided a hole blocking layer in which the difference between an ionization potential of the hole blocking layer and the work function of the adjacent electrode is greater than or equal to 2.3 eV, it is possible to suppress the dark current. In particular, the photoelectric conversion element according to the third embodiment of the present disclosure can suppress the dark current from increasing under a high temperature (for example, greater than or equal to 50 degrees Celsius) condition and under a high bias voltage condition.

5. Application Example of Photoelectric Conversion Element According to an Embodiment of the Present Disclosure Hereinafter, an application example of the photoelectric conversion element including the photoelectric conversion film according to an embodiment of the present disclosure will be described with reference to FIGS. 6 to 8.

(5.1. Configuration of Solid-State Image Sensor)

First, a configuration of the solid-state image sensor to which the photoelectric conversion element according to an embodiment of the present disclosure is applied will be described with reference to FIGS. 6 and 7. FIG. 6 is a schematic diagram illustrating a structure of a solid-state image sensor to which the photoelectric conversion element according to an embodiment of the present disclosure is applied.

Here, in FIG. 6, pixel areas 201, 211 and 231 are areas in which the photoelectric conversion element including the photoelectric conversion film according to an embodiment of the present disclosure are disposed. In addition, control circuits 202, 212 and 242 are arithmetic processing circuits configured to control each component of the solid-state image sensor. Logic circuits 203, 223 and 243 are signal processing circuits configured to process a signal obtained by photoelectric conversion of the photoelectric conversion element in the pixel area.

For example, as illustrated in (A) of FIG. 6, in the solid-state image sensor to which the photoelectric conversion element according to an embodiment of the present disclosure is applied, the pixel area 201, the control circuit 202 and the logic circuit 203 may be formed in one semiconductor chip 200.

In addition, as illustrated in (B) of FIG. 6, the solid-state image sensor to which the photoelectric conversion element according to an embodiment of the present disclosure is applied may be a laminated type solid-state image sensor in which the pixel area 211 and the control circuit 212 are formed in a first semiconductor chip 210, and the logic circuit 223 is formed in a second semiconductor chip 220.

Further, as illustrated in (C) of FIG. 6, the solid-state image sensor to which the photoelectric conversion element according to an embodiment of the present disclosure is applied may be a laminated type solid-state image sensor in which the pixel area 231 is formed in a first semiconductor chip 230 and the control circuit 242 and the logic circuit 243 are formed in a second semiconductor chip 240.

In the solid-state image sensors illustrated in (B) and (C) of FIG. 6, at least one of the control circuit and the logic circuit is formed in a separate semiconductor chip from the semiconductor chip in which the pixel area is formed. Accordingly, since the solid-state image sensors illustrated in (B) and (C) of FIG. 6 can extend the pixel area more than the solid-state image sensor illustrated in (A) of FIG. 6, the number of pixels accommodated in the pixel area is increased. Therefore, it is possible to increase a plane resolution. For this reason, it is more preferable that the solid-state image sensor to which the photoelectric conversion element according to an embodiment of the present disclosure is applied be the laminated type solid-state image sensor illustrated in (B) and (C) of FIG. 6.

Subsequently, a specific structure of a solid-state image sensor to which the photoelectric conversion element according to an embodiment of the present disclosure is applied will be described with reference to FIG. 7. FIG. 7 is a cross sectional view illustrating an outline in a unit pixel of a solid-state image sensor to which the photoelectric conversion element according to an embodiment of the present disclosure is applied. In addition, a solid-state image sensor 300 illustrated in FIG. 7 is a rear surface irradiation type solid-state image sensor in which light is incident from a surface opposite to a surface in which a pixel transistor and the like are formed. In addition, in FIG. 7, with respect to the drawing, an upper side is a light receiving surface, and a lower side is a circuit forming surface in which the pixel transistor and a peripheral circuit are formed.

As illustrated in FIG. 7, the solid-state image sensor 300 has a configuration in which, in a photoelectric conversion area 320, a photoelectric conversion element including a first photodiode PD1 formed in a semiconductor substrate 330, a photoelectric conversion element including a second photodiode PD2 formed in the semiconductor substrate 330 and a photoelectric conversion element including an organic photoelectric conversion film 310 formed at a rear surface side of the semiconductor substrate 330 are laminated in a direction of incidence of light.

The first photodiode PD1 and the second photodiode PD2 are formed in a well area 331 that is a first conductivity type (for example, a p type) semiconductor area of the semiconductor substrate 330 made of silicon.

The first photodiode PD1 includes an n type semiconductor area 332 according to a second conductivity type (for example, an n type) impurity formed at a light receiving surface side of the semiconductor substrate 330 and an extending portion 332a that is formed by extending a part thereof to reach a surface side of the semiconductor substrate 330. A high concentration p type semiconductor area 334 serving as a charge accumulation layer is formed on a surface of the extending portion 332a. In addition, the extending portion 332a is formed as an extraction layer for extracting a signal charge accumulated in the n type semiconductor area 332 of the first photodiode PD1 to a surface side of the semiconductor substrate 330.

The second photodiode PD2 includes an n type semiconductor area 336 formed at a light receiving surface side of the semiconductor substrate 330 and a high concentration p type semiconductor area 338 that is formed at a surface side of the semiconductor substrate 330 and serves as a charge accumulation layer.

In the first photodiode PD1 and the second photodiode PD2, when the p type semiconductor area is formed at an interface of the semiconductor substrate 330, it is possible to suppress the dark current generated at the interface of the semiconductor substrate 330.

Here, the second photodiode PD2 formed in an area that is farthest from the light receiving surface is, for example, a red photoelectric conversion element that absorbs red light and performs photoelectric conversion. In addition, the first photodiode PD1 formed closer to the light receiving surface side than the second photodiode PD2 is, for example, a blue photoelectric conversion element that absorbs blue light and performs photoelectric conversion.

The organic photoelectric conversion film 310 is formed on a rear surface of the semiconductor substrate 330 through an antireflection film 302 and an insulation film 306. In addition, the organic photoelectric conversion film 310 is interposed between an upper electrode 312 and a lower electrode 308 to form the photoelectric conversion element. Here, the organic photoelectric conversion film 310 is, for example, an organic film that absorbs green light and performs photoelectric conversion and is formed as the photoelectric conversion film according to an embodiment of the present disclosure described above. In addition, the upper electrode 312 and the lower electrode 308 are made of, for example, a transparent conductive material such as indium tin oxide and indium zinc oxide.

In addition, the lower electrode 308 is connected to a vertical transfer path 348 that is formed from the rear surface side to the surface side of the semiconductor substrate 330 through a contact plug 304 penetrating the antireflection film 302. The vertical transfer path 348 is formed to have a structure in which a connecting portion 340, a potential barrier layer 342, a charge accumulation layer 344 and a p type semiconductor area 346 are laminated from the rear surface side of the semiconductor substrate 330.

The connecting portion 340 includes an n type impurity area of a high impurity concentration that is formed at the rear surface side of the semiconductor substrate 330 and is formed for an ohmic contact with the contact plug 304. The potential barrier layer 342 includes a p type impurity area of a low concentration and forms a potential barrier between the connecting portion 340 and the charge accumulation layer 344. The charge accumulation layer 344 accumulates a signal charge transmitted from the organic photoelectric conversion film 310 and is formed in an n type impurity area of a lower concentration than the connecting portion 340. In addition, the p type semiconductor area 346 of a high concentration is formed on a surface of the semiconductor substrate 330. With this p type semiconductor area 346, it is possible to suppress the dark current generated at the interface of the semiconductor substrate 330.

Here, at the surface side of the semiconductor substrate 330, a multilayer wiring layer 350 including wires 358 laminated in a plurality of layers is formed through an interlayer insulating layer 351. In addition, in the vicinity of the surface of the semiconductor substrate 330, read circuits 352, 354 and 356 corresponding to the first photodiode PD1, the second photodiode PD2 and the organic photoelectric conversion film 310 are formed. The read circuits 352, 354 and 356 read a signal output from each photoelectric conversion element and transmit the signal to the logic circuit (not illustrated). Further, a supporting substrate 360 is formed on a surface of the multilayer wiring layer 350.

On the other hand, at a light receiving surface side of the upper electrode 312, a light shielding film 316 is formed to shield the extending portion 332a of the first photodiode PD1 and the vertical transfer path 348. Here, a separate area between the light shielding films 316 is the photoelectric conversion area 320. In addition, an onchip lens 318 is formed above the light shielding film 316 through a flattening film 314.

The solid-state image sensor 300 to which the photoelectric conversion element according to an embodiment of the present disclosure is applied has been described above. In addition, in the solid-state image sensor 300 to which the photoelectric conversion element according to an embodiment of the present disclosure is applied, since color separation is performed on a unit pixel in a longitudinal direction, a color filter and the like are not provided.

(5.2. Configuration of Electronic Device)

Next, a configuration of an electronic device to which the photoelectric conversion element according to an embodiment of the present disclosure is applied will be described with reference to FIG. 8. FIG. 8 is a block diagram illustrating a configuration of an electronic device to which the photoelectric conversion element according to an embodiment of the present disclosure is applied.

As illustrated in FIG. 8, an electronic device 400 includes an optical system 402, a solid-state image sensor 404, a digital signal processor (DSP) circuit 406, a control unit 408, an output unit 412, an input unit 414, a frame memory 416, a recording unit 418 and a power supply unit 420.

Here, the DSP circuit 406, the control unit 408, the output unit 412, the input unit 414, the frame memory 416, the recording unit 418 and the power supply unit 420 are connected to each other via a bus line 410.

The optical system 402 obtains incident light from an object and forms an image on an imaging surface of the solid-state image sensor 404. In addition, the solid-state image sensor 404 includes the photoelectric conversion element according to an embodiment of the present disclosure, converts an intensity of incident light focused on an imaging surface by the optical system 402 into an electrical signal in units of pixels, and outputs the result as a pixel signal.

The DSP circuit 406 processes the pixel signal transmitted from the solid-state image sensor 404 and outputs the result to the output unit 412, the frame memory 416, the recording unit 418 and the like. In addition, the control unit 408 includes, for example, an arithmetic processing circuit, and controls operations of each of the components of the electronic device 400.

The output unit 412 is, for example, a panel type display device such as a liquid crystal display and an organic electroluminescent display, and displays a video or a still image imaged by the solid-state image sensor 404. Here, the output unit 412 may also include a sound output device such as a speaker and a headphone. Here, the input unit 414 is, for example, a device for inputting a user's manipulation such as a touch panel and a button and issues manipulation commands for various functions of the electronic device 400 according to the user's manipulation.

The frame memory 416 temporarily stores the video, the still image and the like imaged by the solid-state image sensor 404. In addition, the recording unit 418 records the video, the still image and the like imaged by the solid-state image sensor 404 in a removable storage medium such as a magnetic disk, an optical disc, a magneto optical disc and a semiconductor memory.

The power supply unit 420 appropriately supplies various types of power serving as operating power of the DSP circuit 406, the control unit 408, the output unit 412, the input unit 414, the frame memory 416 and the recording unit 418 to these supply targets.

The electronic device 400 to which the photoelectric conversion element according to an embodiment of the present disclosure is applied has been described above. The electronic device 400 to which the photoelectric conversion element according to an embodiment of the present disclosure is applied may be, for example, an imaging apparatus.

6. Summary

As described above, when the photoelectric conversion film according to an embodiment of the present disclosure includes the above-described compound, it is possible to selectively absorb light of a specific wavelength band. Accordingly, since the photoelectric conversion element including the photoelectric conversion film according to an embodiment of the present disclosure has appropriate spectral characteristics as the photoelectric conversion element of the solid-state image sensor, it is possible to increase sensitivity and a resolution of the solid-state image sensor.

The photoelectric conversion film according to the first embodiment of the present disclosure includes the quinacridone derivative represented by the above General formula (1) and the subphthalocyanine derivative represented by the above General formula (2). The subphthalocyanine derivative represented by the above General formula (2) has a high heat resistance, selectively absorbs green light, and has spectral characteristics matching the quinacridone derivative. Therefore, the photoelectric conversion film according to the first embodiment of the present disclosure has sharp spectral characteristics in which green light is absorbed. Accordingly, since the photoelectric conversion film according to the first embodiment of the present disclosure can selectively absorb green light, it is appropriate for a green photoelectric conversion element of the solid-state image sensor. Therefore, it is possible to increase sensitivity and a resolution of the solid-state image sensor.

In addition, the photoelectric conversion film according to the second embodiment of the present disclosure includes the transparent compound represented by the above General formula (3) or (4) that does not absorb visible light. Since the transparent compound represented by the above General formula (3) or (4) that does not absorb visible light does not have an absorption band of visible light, there is no influence on spectral characteristics of the photoelectric conversion film. Therefore, the photoelectric conversion film formed to include the transparent compound represented by General formula (3) or (4) and the organic dye compound can have the same spectral characteristics as the organic dye compound. Accordingly, since the photoelectric conversion film according to the second embodiment of the present disclosure can selectively absorb light that is absorbed by the organic dye compound, it is appropriate for the photoelectric conversion element of the solid-state image sensor. Therefore, it is possible to increase sensitivity and a resolution of the solid-state image sensor.

Further, the photoelectric conversion element according to the third embodiment of the present disclosure includes the hole blocking layer in which the difference between an ionization potential of the hole blocking layer and the work function of the adjacent electrode is greater than or equal to 2.3 eV. Since such a hole blocking layer can suppress holes from being introduced from the electrode due to an external electric field, it is possible to decrease the dark current. Accordingly, since the photoelectric conversion element according to the third embodiment of the present disclosure can suppress the dark current, it is appropriate for the solid-state image sensor. It is possible to increase sensitivity and a resolution of the solid-state image sensor.

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present disclosure may also be configured as below.

(1)

A photoelectric conversion film including:
a quinacridone derivative represented by the following General formula (1); and
a subphthalocyanine derivative represented by the following General formula (2),

[Chem. 32]

General formula (1)

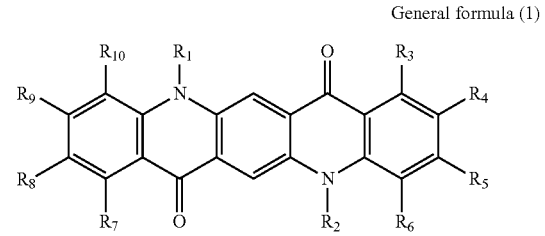

wherein, in General formula (1),
$R_1$ to $R_{10}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, or an aryl or heteroaryl group formed by condensing at least two or more of any adjacent $R_1$ to $R_{10}$, and

[Chem. 33]

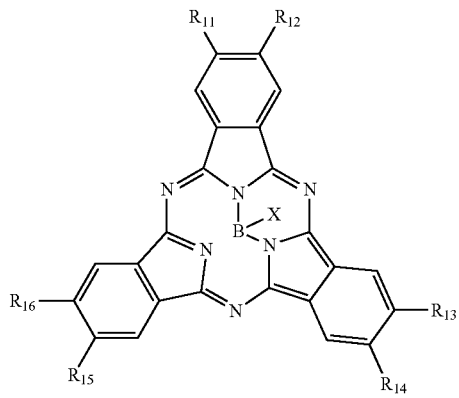

General formula (2)

in General formula (2), $R_1$ to $R_{16}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, X represents any substituent selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group, and at least one of $R_{11}$ to $R_{16}$ represents fluorine.

(2)
The photoelectric conversion film according to (1), wherein $R_{11}$ to $R_{16}$ represent fluorine.

(3)
The photoelectric conversion film according to (1) or (2), wherein X represents any substituent selected from the group consisting of a halogen, a hydroxy group, a substituted or unsubstituted alkoxy group, and a substituted or unsubstituted aryloxy group.

(4)
The photoelectric conversion film according to any one of (1) to (3), wherein a lowest unoccupied molecular orbital (LUMO) level of the subphthalocyanine derivative is deeper than an LUMO level of the quinacridone derivative, and a difference between the LUMO level of the subphthalocyanine derivative and the LUMO level of the quinacridone derivative is greater than or equal to 0.1 eV and less than or equal to 1.0 eV.

(5)
The photoelectric conversion film according to any one of (1) to (4), wherein the quinacridone derivative and the subphthalocyanine derivative form a bulk hetero film.

(6)
A photoelectric conversion film including:
a transparent compound that is represented by the following General formula (3) or (4) and does not absorb visible light,

[Chem. 34]

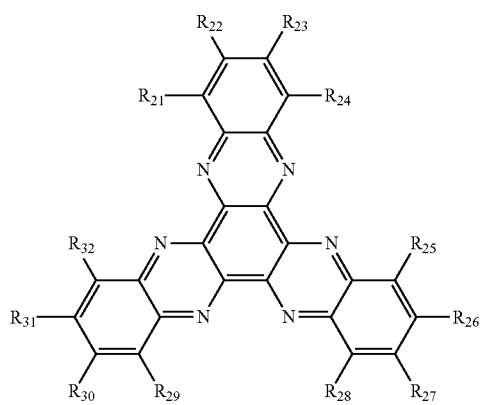

General formula (3)

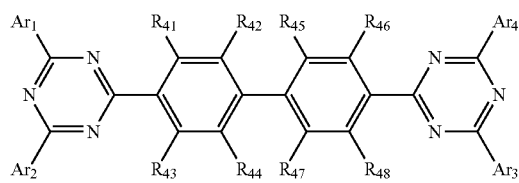

General formula (4)

wherein, in General formula (3), $R_{21}$ to $R_{32}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, or an aryl or heteroaryl group formed by condensing at least two or more of any adjacent $R_{21}$ to $R_{32}$, and in General formula (4), $R_{41}$ to $R_{48}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, an imide group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, or an aryl or heteroaryl group formed by condensing at least two or more of any adjacent $R_{41}$ to $R_{48}$, and Ar$_1$ to Ar$_4$ each independently represent a substituted or unsubstituted aryl group or a substituted or unsubstituted heteroaryl group.

(7)
The photoelectric conversion film according to (6), wherein R$_{21}$, R$_{24}$, R$_{25}$, R$_{28}$, R$_{29}$, and R$_{32}$ represent hydrogen in General formula (3).

(8)
The photoelectric conversion film according to (6), wherein at least one of substituents of Ar$_1$ to Ar$_4$ and R$_{41}$ to R$_{48}$ is an electron attracting group in General formula (4).

(9)
The photoelectric conversion film according to (8), wherein the electron attracting group is any substituent selected from the group consisting of a halogen, a cyano group, a nitro group, a sulfonyl group, an arylsulfonyl group, an alkylsulfonyl group, an acyl group, an acylamino group, an acyloxy group, an imide group, a carboxy group, a carboxamido group, a carboalkoxy group, a halogenated alkyl group, and a halogenated aryl group.

(10)
The photoelectric conversion film according to any one of (6) to (9), further including: an organic dye compound, wherein the organic dye compound and the compound represented by General formula (3) or General formula (4) form a bulk hetero film.

(11)
The photoelectric conversion film according to (10), wherein the organic dye compound is a compound that absorbs green light having a wavelength band of greater than or equal to 450 nm and less than or equal to 600 nm.

(12)
The photoelectric conversion film according to (10) or (11), wherein the organic dye compound is a quinacridone derivative represented by the following General formula (1),

[Chem. 35]

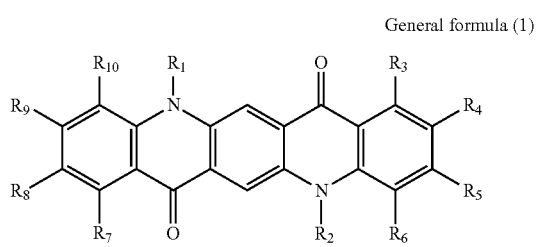

General formula (1)

wherein, in General formula (1),
R$_1$ to R$_{10}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, or an aryl or heteroaryl group formed by condensing at least two or more of any adjacent R$_1$ to R$_{10}$.

(13)
The photoelectric conversion film according to (12), wherein an LUMO level of the compound represented by General formula (3) or (4) is deeper than an LUMO level of the quinacridone derivative, and a difference between the LUMO level of the compound represented by General formula (3) or (4) and the LUMO level of the quinacridone derivative is greater than or equal to 0.1 eV and less than or equal to 1.0 eV.

(14)
A photoelectric conversion element including:
a photoelectric conversion film;
a pair of electrodes that are disposed at both sides of the photoelectric conversion film, which is interposed therebetween; and
a hole blocking layer disposed between the photoelectric conversion film and one of the electrodes,
wherein a difference between an ionization potential of the hole blocking layer and a work function of one of the electrodes, the one being adjacent to the hole blocking layer, is greater than or equal to 2.3 eV.

(15)
The photoelectric conversion element according to (14), wherein the hole blocking layer includes a compound represented by the following General formula (5),

[Chem. 36]

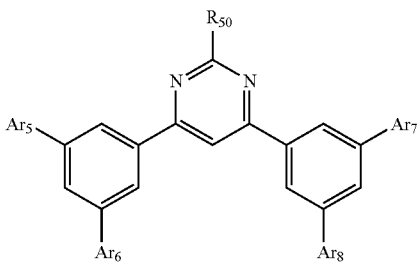

General formula (5)

wherein, in General formula (5),
R$_{50}$ represents any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, and Ar$_5$ to Ar$_{8s}$ represent a substituted or unsubstituted heteroaryl group.

(16)
The photoelectric conversion element according to (15), wherein at least one of substituents of Ar$_5$ to Ar$_8$ and R$_{50}$ is an electron attracting group.

(17)
The photoelectric conversion element according to (16), wherein the electron attracting group is any substituent selected from the group consisting of a halogen, a cyano group, a nitro group, a sulfonyl group, an arylsulfonyl group, an alkylsulfonyl group, an acyl group, an acylamino group, an acyloxy group, an imide group, a carboxy group, a carboxamido group, a carboalkoxy group, a halogenated alkyl group, and a halogenated aryl group.

(18)
The photoelectric conversion element according to (15), wherein the compound represented by General formula (5) is a compound represented by any of the following structural formulas.

-continued
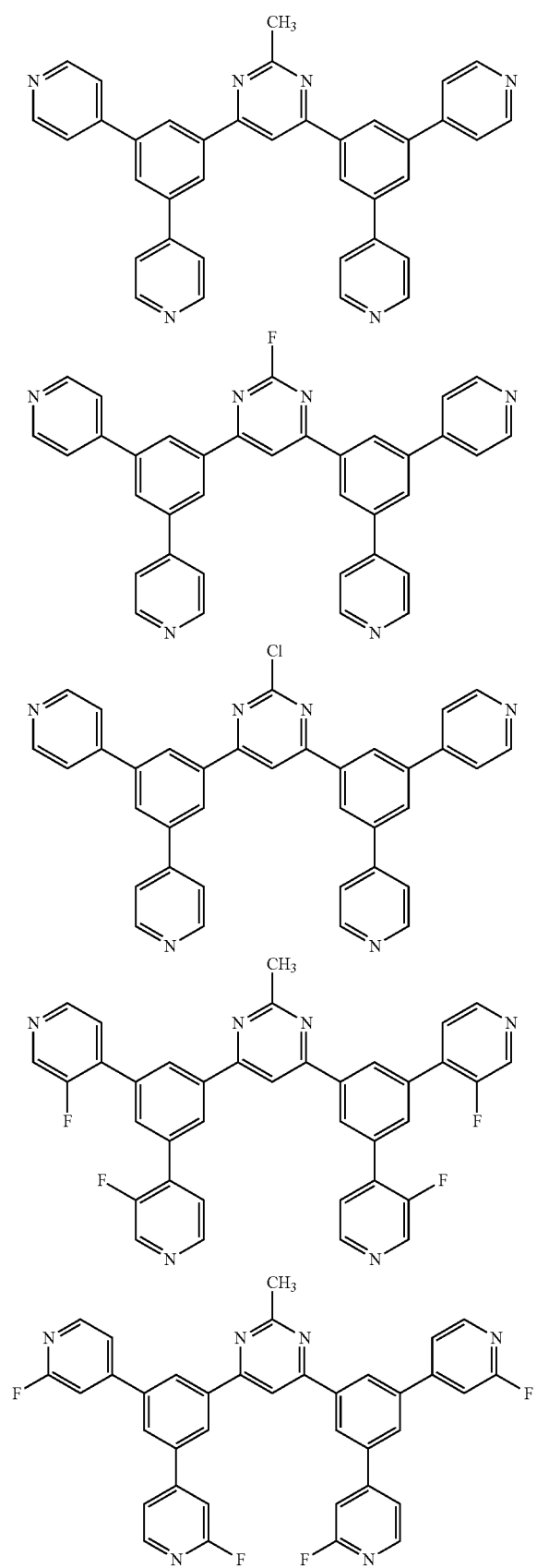
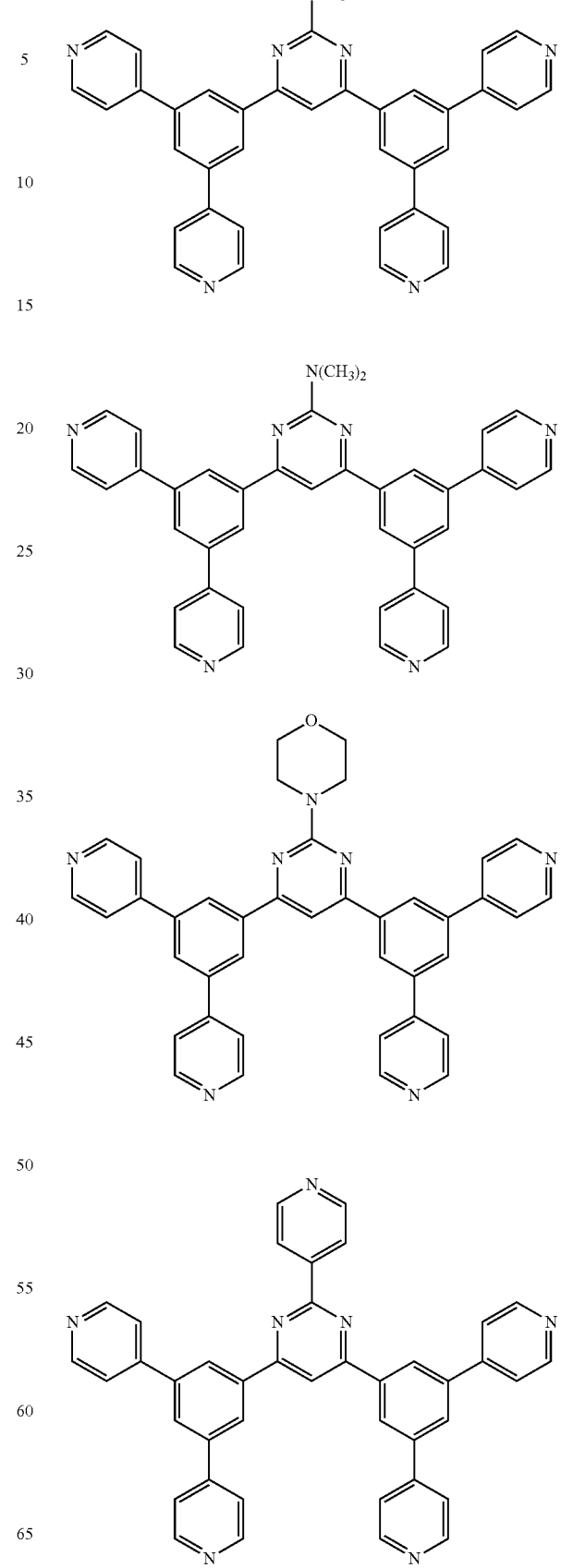

-continued

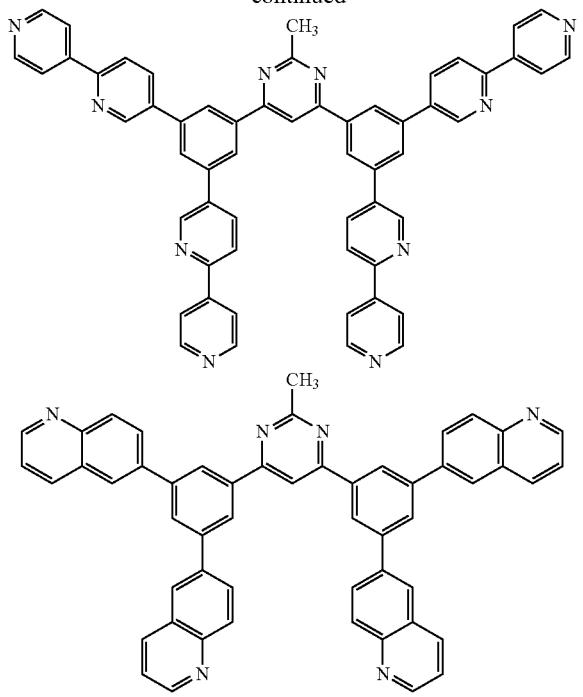

(19) The photoelectric conversion element according to any one of (14) to (18), wherein the hole blocking layer has a thickness of greater than or equal to 5 nm and less than or equal to 20 nm.

(20) The photoelectric conversion element according to any one of (14) to (19), wherein one adjacent electrode is a transparent electrode.

(21) The photoelectric conversion element according to (20), wherein one adjacent electrode includes at least one of indium tin oxide and indium zinc oxide.

(22) A solid-state image sensor including a photoelectric conversion film that includes a quinacridone derivative represented by the following General formula (1) and a subphthalocyanine derivative represented by the following General formula (2).

[Chem. 38]

General formula (1)

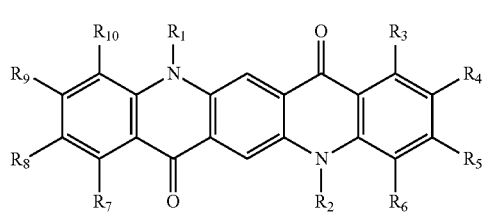

In General formula (1), $R_1$ to $R_{10}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group or an aryl or heteroaryl group formed by condensing at least two or more of any adjacent $R_1$ to $R_{10}$.

[Chem. 39]

General formula (2)

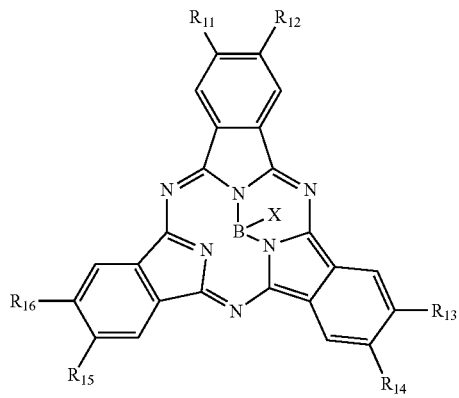

In General formula (2), $R_{11}$ to $R_{16}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group, X represents any substituent selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group and a substituted or unsubstituted arylthio group, and at least one of $R_{11}$ to $R_{16}$ represents fluorine.

(23) A solid-state image sensor including a photoelectric conversion film containing a transparent compound that is represented by the following General formula (3) or (4) and does not absorbs visible light.

[Chem.40]

General formula (3)

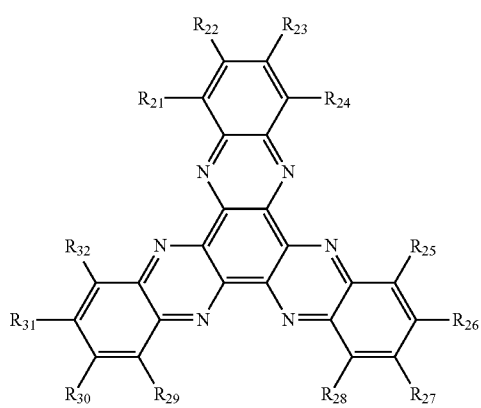

General formula (4)

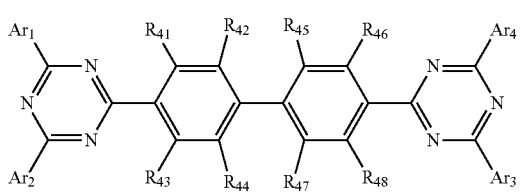

In General formula (3), $R_{21}$ to $R_{32}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group or an aryl or heteroaryl group formed by condensing at least two or more of any adjacent $R_{21}$ to $R_{32}$, in General formula (4), $R_{41}$ to $R_{48}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, an imide group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group or an aryl or heteroaryl group formed by condensing at least two or more of any adjacent $R_{41}$ to $R_{48}$, and $Ar_1$ to $Ar_4$ each independently represent a substituted or unsubstituted aryl group or a substituted or unsubstituted heteroaryl group.

(24)
A solid-state image sensor including:
a photoelectric conversion element containing,
a photoelectric conversion film,
a pair of electrodes that are disposed at both sides of the photoelectric conversion film, which is interposed therebetween, and
a hole blocking layer disposed between the photoelectric conversion film and one of the electrodes,
wherein a difference between an ionization potential of the hole blocking layer and a
work function of one adjacent electrode is greater than or equal to 2.3 eV.

(25)
The solid-state image sensor according to any one of (22) to (24), wherein the photoelectric conversion film includes an organic dye compound that absorbs green light having a wavelength of band of greater than or equal to 450 nm and less than or equal to 600 nm and performs photoelectric conversion on the absorbed green light.

(26)
The solid-state image sensor according to any one of (22) to (24) configured as a laminated type solid-state image sensor that includes a first chip in which the photoelectric conversion film is formed and a second chip in which a signal processing circuit configured to process a signal obtained by photoelectric conversion by the photoelectric conversion film is formed and that is laminated on the first chip.

(27)
An electronic device including:
a solid-state image sensor containing a photoelectric conversion film having a quinacridone derivative represented by the following General formula (1) and a subphthalocyanine derivative represented by the following General formula (2);
an optical system configured to guide incident light to the solid-state image sensor; and
an arithmetic processing circuit configured to arithmetically process a signal output from the solid-state image sensor.

[Chem.41]

General formula (1)

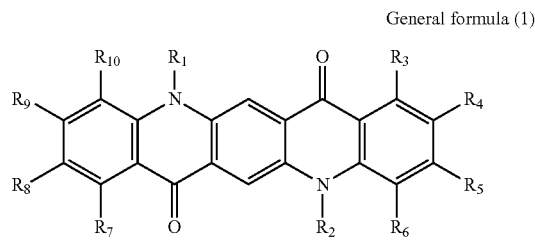

In General formula (1), $R_1$ to $R_{10}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group or an aryl or heteroaryl group formed by condensing at least two or more of any adjacent $R_1$ to $R_{10}$.

[Chem.42]

General formula (2)

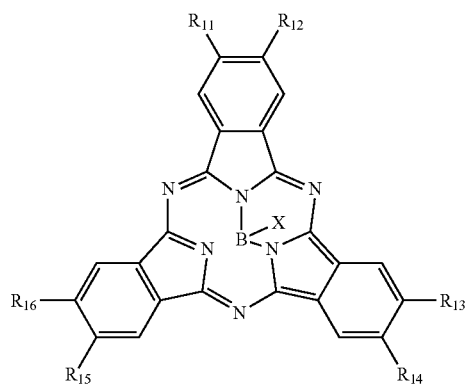

In General formula (2), $R_{11}$ to $R_{16}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group, X represents any substituent selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group and a substituted or unsubstituted arylthio group, and at least one of $R_{11}$ to $R_{16}$ represents fluorine.

(28)

An electronic device including:

a solid-state image sensor including a photoelectric conversion film containing a transparent compound that is represented by the following General formula (3) or (4) and does not absorb visible light;

an optical system configured to guide incident light to the solid-state image sensor; and an arithmetic processing circuit configured to arithmetically process a signal output from the solid-state image sensor.

[Chem.43]

General formula (3)

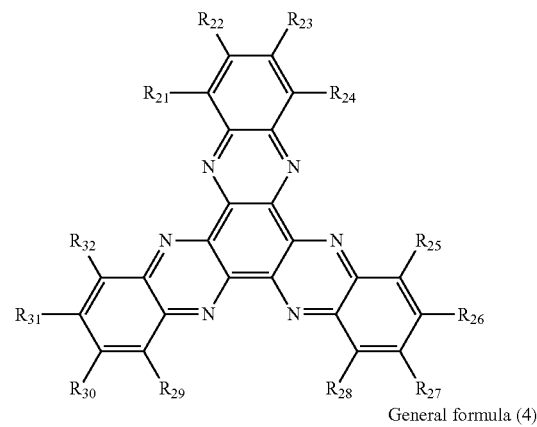

General formula (4)

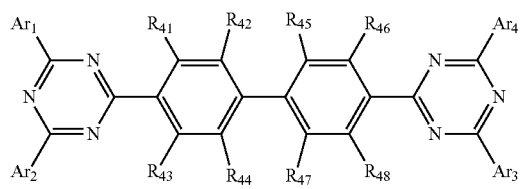

In General formula (3), $R_{21}$ to $R_{32}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group or an aryl or heteroaryl group formed by condensing at least two or more of any adjacent $R_{21}$ to $R_{32}$, and in General formula (4), $R_{41}$ to $R_{48}$ each independently represent any substituent selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, an imide group, a carboxy group, a carboxamido group, a carboalkoxy group, a substituted or unsubstituted alkyl group, a substituted or unsubstituted cycloalkyl group, a substituted or unsubstituted aryl group and a substituted or unsubstituted heteroaryl group or an aryl or heteroaryl group formed by condensing at least two or more of any adjacent $R_{41}$ to $R_{48}$, and Ar$_1$ to Ar$_4$ each independently represent a substituted or unsubstituted aryl group or a substituted or unsubstituted heteroaryl group.

(29)

An electronic device including:

a solid-state image sensor including a photoelectric conversion element that contains a photoelectric conversion film, a pair of electrodes that are disposed at both sides of the photoelectric conversion film, which is interposed therebetween, and a hole blocking layer disposed between the photoelectric conversion film and one of the electrodes, wherein the difference between an ionization potential of the hole blocking layer and a work function of one adjacent electrode is greater than or equal to 2.3 eV;

an optical system configured to guide incident light to the solid-state image sensor; and an arithmetic processing circuit configured to arithmetically process a signal output from the solid-state image sensor.

(30)

A photoelectric conversion film including:

a quinacridone derivative represented by General formula (1):

[Chem.44]

General formula (1)

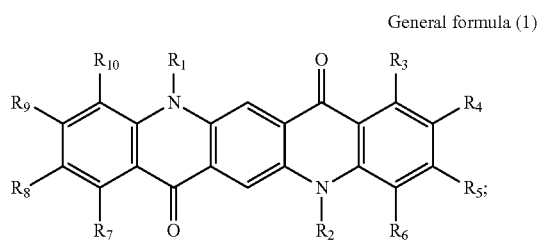

and a subphthalocyanine derivative represented by General formula (2):

[Chem.45]

General formula (2)

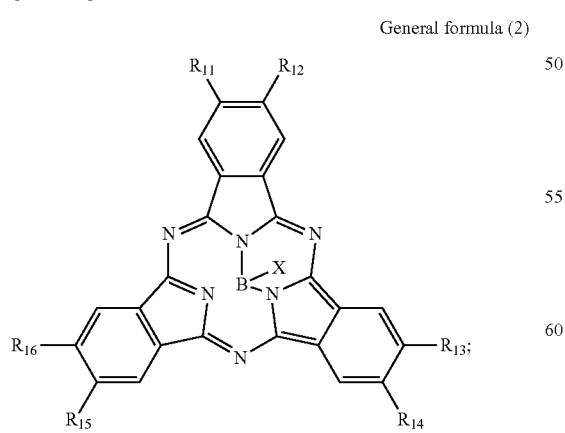

where in General formula (1), R$_1$ to R$_{10}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the R$_1$ to R$_{10}$ that are adjacent to one another, where in General formula (2), R$_{11}$ to R$_{16}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, where X is selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group, and where at least one of R$_{11}$ to R$_{16}$ represents fluorine.

(31) The photoelectric conversion film according to (30), where R$_{11}$ to R$_{16}$ are each fluorine.

(32)

The photoelectric conversion film according to any one of (30) to (31), where X is selected from the group consisting of a halogen, a hydroxy group, a substituted or unsubstituted alkoxy group, and a substituted or unsubstituted aryloxy group.

(33)

The photoelectric conversion film according to any one of (30) to (32), where a lowest unoccupied molecular orbital (LUMO) level of the subphthalocyanine derivative is deeper than a LUMO level of the quinacridone derivative, and a difference between the LUMO level of the subphthalocyanine derivative and the LUMO level of the quinacridone derivative is greater than or equal to 0.1 eV and less than or equal to 1.0 eV.

(34)

The photoelectric conversion film according to any one of (30) to (33), where the quinacridone derivative and the subphthalocyanine derivative are a bulk hetero film.

(35)
A photoelectric conversion film including:
a transparent compound that does not absorb visible light and that is represented by at least one of General formula (3) and General formula (4):

[Chem.46]

General formula (3)

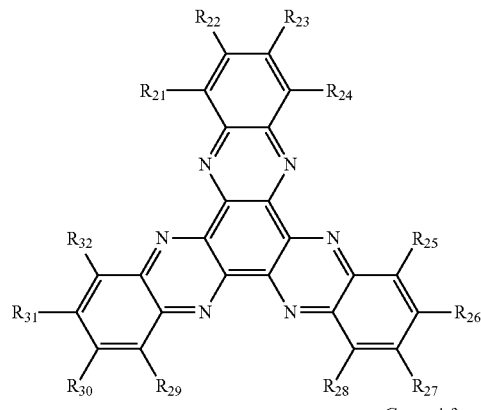

General formula (4)

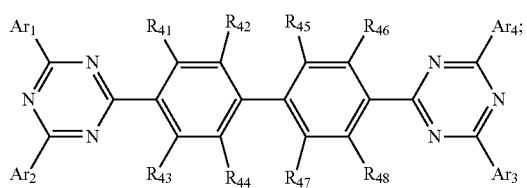

where in General formula (3), $R_{21}$ to $R_{32}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the $R_{21}$ to $R_{32}$ that are adjacent to one another, and
where in General formula (4), $R_{41}$ to $R_{48}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, an imide group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the $R_{41}$ to $R_{48}$ that are adjacent to one another, and
where $Ar_1$ to $Ar_4$ are each independently one of a substituted or unsubstituted aryl group and a substituted or unsubstituted heteroaryl group.

(36)
The photoelectric conversion film according to (35), where the transparent compound is represented by at least General formula (3) and $R_{21}$, $R_{24}$, $R_{25}$, $R_{28}$, $R_{29}$, and $R_{32}$ are each hydrogen in General formula (3).
(37)
The photoelectric conversion film according to any one of (35) to (36), where the transparent compound is represented by at least General formula (4) and at least one of $Ar_1$ to $Ar_4$ and $R_{41}$ to $R_{48}$ is an electron attracting group in General formula (4).
(38)
The photoelectric conversion film according to any one of (35) to (37), where the electron attracting group is selected from the group consisting of a halogen, a cyano group, a nitro group, a sulfonyl group, an arylsulfonyl group, an alkylsulfonyl group, an acyl group, an acylamino group, an acyloxy group, an imide group, a carboxy group, a carboxamido group, a carboalkoxy group, a halogenated alkyl group, and a halogenated aryl group.
(39)
The photoelectric conversion film according to any one of (35) to (38), further including:
an organic dye compound, where the organic dye compound and the compound represented by the at least one of General formula (3) and General formula (4) are a bulk hetero film.
(40)
The photoelectric conversion film according to any one of (35) to (39), where the organic dye compound absorbs green light having a wavelength band of greater than or equal to approximately 450 nm and less than or equal to approximately 600 nm.
(41)
The photoelectric conversion film according to any one of (35) to (40), where the organic dye compound is a quinacridone derivative represented by General formula (1):

[Chem.47]

General formula (1)

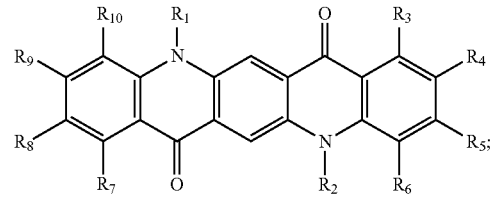

where in General formula (1), $R_1$ to $R_{10}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the $R_1$ to $R_{10}$ that are adjacent to one another.
(42)
The photoelectric conversion film according to any one of (35) to (41), where a LUMO level of the at least one of the General formula (3) and the General formula (4) is deeper than a LUMO level of the quinacridone derivative, and a difference between the LUMO level of the at least one of the General formula (3) and the General formula (4) and the LUMO level of the quinacridone derivative is greater than or equal to 0.1 eV and less than or equal to 1.0 eV.

(43)
A photoelectric conversion element including:
a photoelectric conversion film;
a pair of electrodes that are disposed at both sides of the photoelectric conversion film, which is interposed therebetween; and
a hole blocking layer disposed between the photoelectric conversion film and one of the electrodes,
where a difference between an ionization potential of the hole blocking layer and a work function of the one of the electrodes is greater than or equal to 2.3 eV.

(44)
The photoelectric conversion element according to (43), where the hole blocking layer includes a compound represented by General formula (5):

[Chem.48]

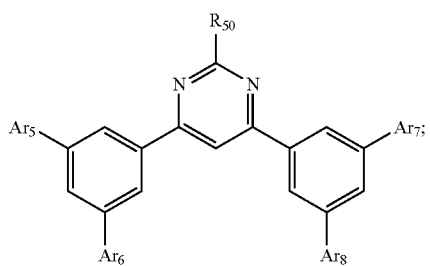

General formula (5)

where in General formula (5), $R_{50}$ is selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, and where $Ar_5$ to $Ar_8$ each represent a substituted or unsubstituted heteroaryl group.

(45)
The photoelectric conversion element according to any one of (43) to (44), where at least one of the $Ar_5$ to $Ar_8$ and $R_0$ is an electron attracting group.

(46)
The photoelectric conversion element according to any one of (43) to (45), where the electron attracting group is selected from the group consisting of a halogen, a cyano group, a nitro group, a sulfonyl group, an arylsulfonyl group, an alkylsulfonyl group, an acyl group, an acylamino group, an acyloxy group, an imide group, a carboxy group, a carboxamido group, a carboalkoxy group, a halogenated alkyl group, and a halogenated aryl group.

(47)
The photoelectric conversion element according to any one of (43) to (46), where the General formula (5) is any of the following structural formulas:

[Chem. 49]

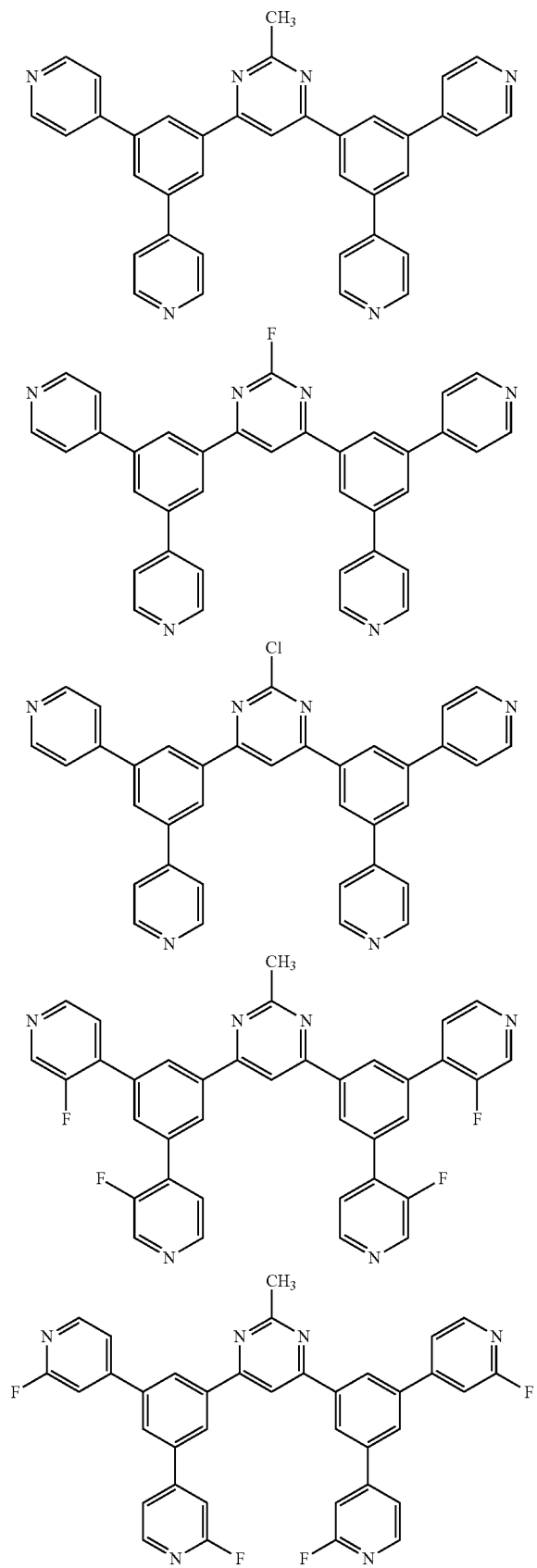

-continued

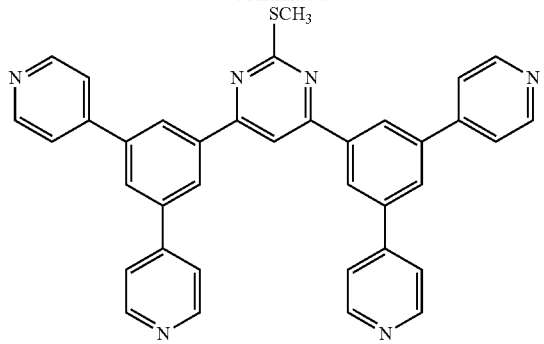

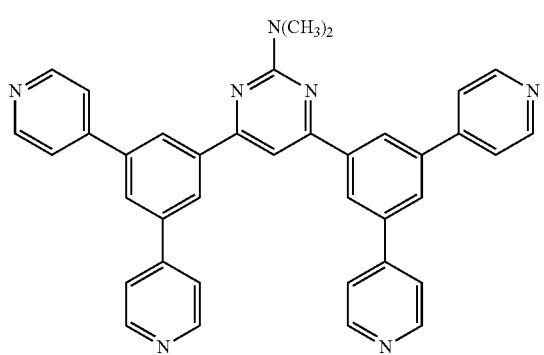

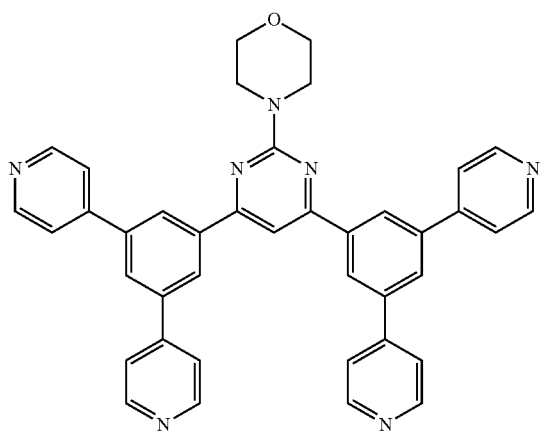

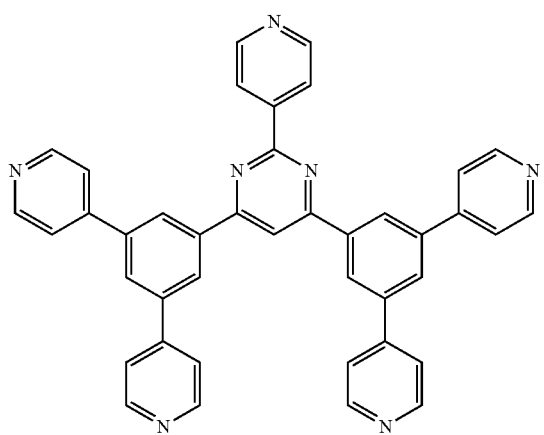

-continued

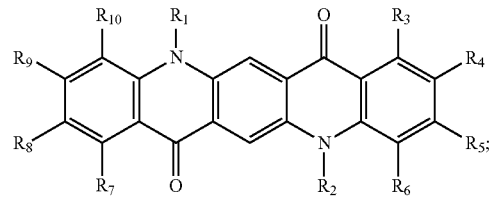

(48)

The photoelectric conversion element according to any one of (43) to (47), where the hole blocking layer has a thickness of greater than or equal to approximately 5 nm and less than or equal to approximately 20 nm.

(49)

An electronic device including:

a photoelectric conversion film that includes:

a quinacridone derivative represented by General formula (1):

[Chem.50]

General formula (1)

![General formula 1 structure with R1-R10 substituents on quinacridone core]

and a subphthalocyanine derivative represented by General formula (2):

[Chem.51]

General formula (2)

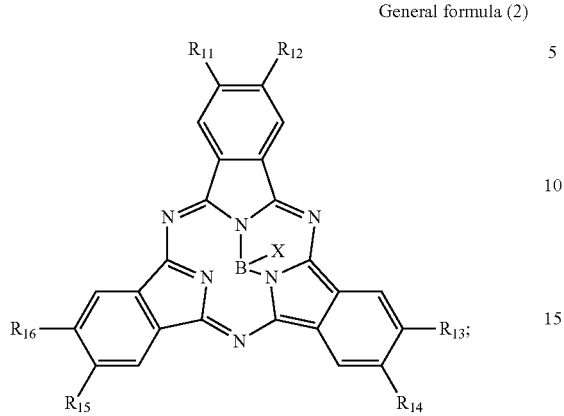

where in General formula (1), $R_1$ to $R_{10}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, a substituted or unsubstituted heteroaryl group, and an aryl or heteroaryl group formed by condensing at least two of the $R_1$ to $R_{10}$ that are adjacent to one another;

where in General formula (2), $R_1$ to $R_{16}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group;

where X is selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group; and where at least one of $R_{11}$ to $R_{16}$ represents fluorine.

REFERENCE SIGNS LIST 100 photoelectric conversion element
102 substrate
104 lower electrode
106 electron blocking layer
108 photoelectric conversion layer
110 hole blocking layer
112 upper electrode

The invention claimed is:

1. A light detecting device, comprising:
a first electrode and a second electrode;
a photoelectric conversion film that selectively absorbs light of a specific wavelength and disposed between the first electrode and the second electrode;
wherein the photoelectric conversion film includes a first compound and a second compound, and the first compound and the second compound are formed as a bulk hetero mixed film,
wherein the first compound is a subphthalocyanine derivative represented by a general formula:

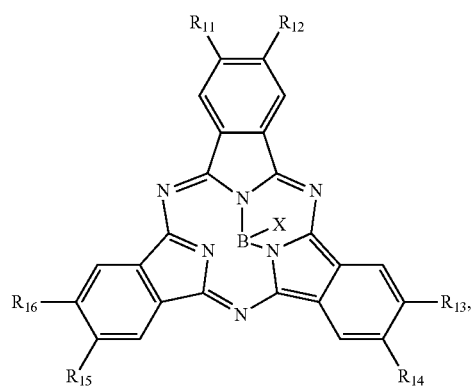

wherein $R_{11}$ to $R_{16}$ are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, and wherein at least one of $R_{11}$ to $R_{16}$ is fluorine,
wherein X is selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group,
wherein the second compound is configured to transport a hole or an electron,
and
wherein the photoelectric conversion film has a microstructure in which one of the first compound and the second compound is in a crystal fine particle state or in an amorphous state.

2. The light detecting device according to claim 1, wherein the photoelectric conversion film has a microstructure in which one of the first compound and the second compound is in a crystal fine particle state and the other of the first compound or the second compound is in an amorphous state or a crystal fine particle state.

3. The light detecting device according to claim 1, wherein the photoelectric conversion film has a microstructure in which the first compound is in a crystal fine particle state and the second compound is in an amorphous state.

4. The light detecting device according to claim 1, wherein the photoelectric conversion film has a microstructure in which the first compound is in an amorphous state and the second compound is in a crystal fine particle state.

5. The light detecting device according to claim 1, wherein each of $R_{11}$ to $R_{16}$ is fluorine.

6. The light detecting device according to claim 1, wherein at least one of $R_{11}$ and $R_{12}$ is fluorine, at least one of $R_{13}$ and $R_{14}$ is fluorine, and at least one of $R_{15}$ and $R_{16}$ is fluorine.

7. The light detecting device according to claim 1, wherein X is selected from the group consisting of a halogen, a hydroxy group, a substituted or unsubstituted alkoxy group, and a substituted or unsubstituted aryloxy group.

8. The light detecting according to claim 1, wherein the first compound is represented by one of the following formulas:

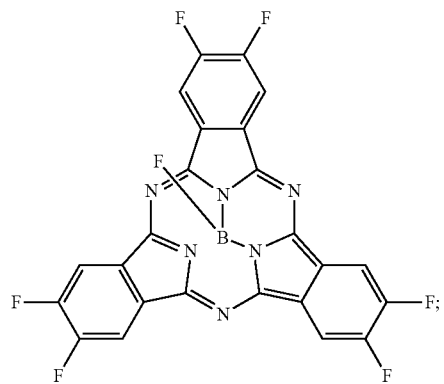

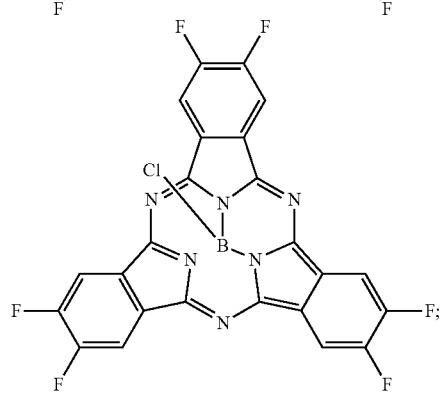

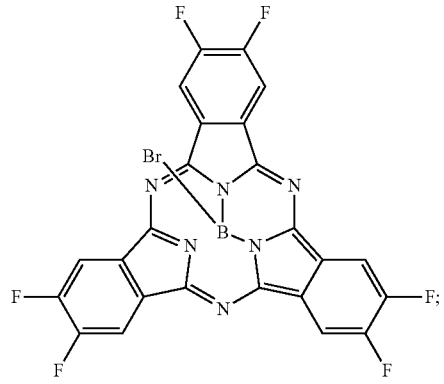

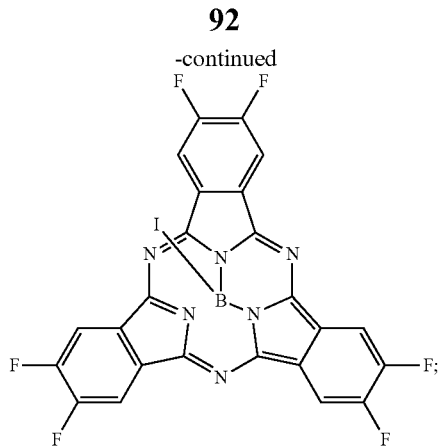

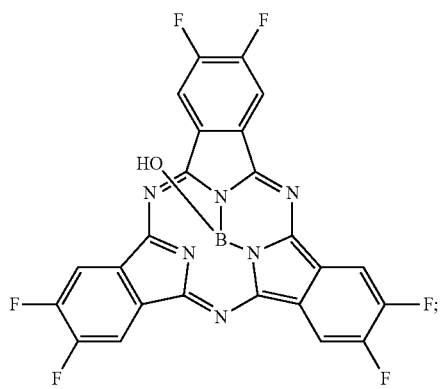

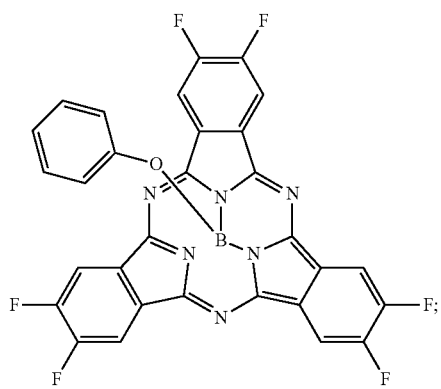

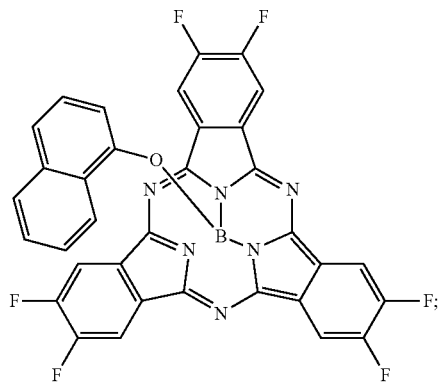

-continued

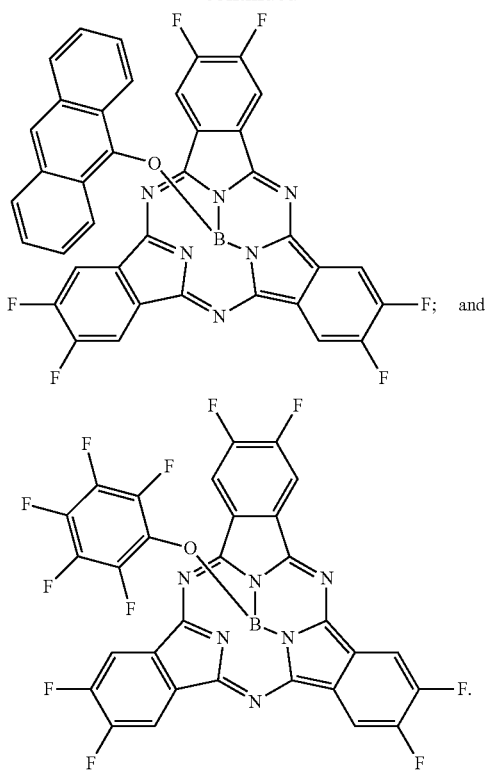

9. The light detecting device according to claim 1, wherein the first compound is represented by one of the following formulas:

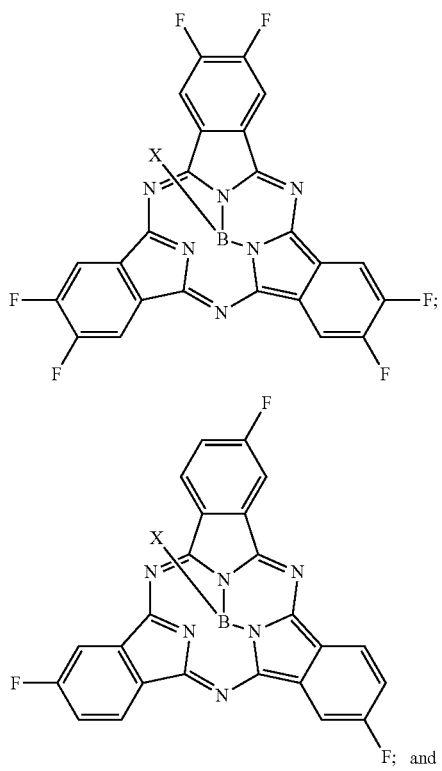

-continued

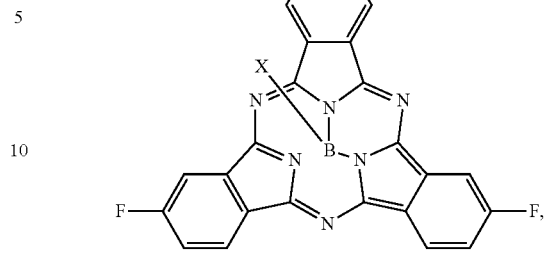

wherein X is selected from the group consisting of a halogen, a hydroxy group, a substituted or unsubstituted alkoxy group, and a substituted or unsubstituted aryloxy group.

10. The light device according to claim 1, further comprising a third compound to transport a hole or an electron.

11. The light detecting device according to claim 1, further comprising a third compound to block a hole from being introduced by the first electrode to the photoelectric conversion film.

12. The light detecting device according to claim 11, wherein the third compound is an electron accepting material selected from the group consisting of fullerene, carbon nanotubes, oxadiazole, a triazole compound, anthraquinodimethane, diphenylquinone, distyrylarylene, and a silole compound.

13. The light detecting device according to claim 11, wherein the third compound is fullerene.

14. The light detecting device according to claim 1, wherein the first compound absorbs green light having a wavelength band of greater than or equal to approximately 450 nm and less than or equal to approximately 600 nm.

15. The light detecting device according to claim 1, further comprising;
a semiconductor substrate disposed below the photoelectric conversion film,
wherein the semiconductor substrate includes a first photodiode and a second photodiode disposed below the first photodiode, and
wherein the first photodiode absorbs blue light, the second photodiode absorbs red light, and the first photodiode and the second photodiode perform photoelectric conversion.

16. The light detecting device according to claim 1, further comprising
a semiconductor substrate disposed below the photoelectric conversion film, wherein the semiconductor substrate includes a photoelectric conversion region.

17. The light detecting device according to claim 1, wherein the first compound has a lowest unoccupied molecular orbital (LUMO) level of greater than or equal to −4.8 eV and less than or equal to −3.5 eV.

18. The light detecting device according to claim 1, wherein the first compound has a highest occupied molecular orbital (HOMO) level of greater than or equal to −7.0 eV and less than or equal to −5.5 eV.

19. The light detecting device according to claim 1, wherein a lowest unoccupied molecular orbital (LUMO) level of the first compound is deeper than a LUMO level of the second compound, and a difference between the LUMO level of the first compound and the LUMO level of the second compound is greater than or equal to 0.1 eV and less than or equal to 1.0 eV.

20. The light detecting device according to claim 1, wherein the light detecting device is a solid-state image sensor.

21. A light detecting device, comprising:
a first electrode;
a second electrode; and
an organic region comprising a first material and a second material, the first material comprises a subphthalocyanine derivative represented by a general formula:

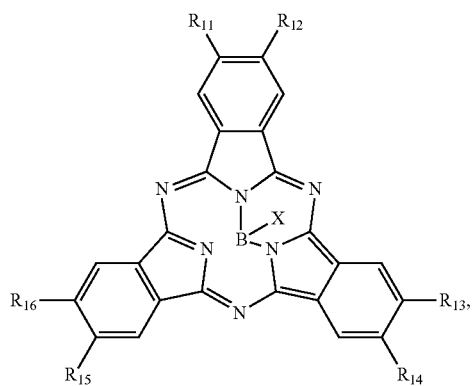

wherein $R_{11}$ to $R_{16}$ are each are each independently selected from the group consisting of hydrogen, a halogen, a hydroxy group, an alkoxy group, a cyano group, a nitro group, a silylalkyl group, a silylalkoxy group, an arylsilyl group, a thioalkyl group, a thioaryl group, a sulfonyl group, an arylsulfonyl group, an alkylsulfonyl group, an amino group, an alkylamino group, an arylamino group, an acyl group, an acylamino group, an acyloxy group, a carboxy group, a carboxamido group, a carboalkoxy group, a substituted or unsubstituted alkyl group, a substituted or unsubstituted cycloalkyl group, a substituted or unsubstituted aryl group, and a substituted or unsubstituted heteroaryl group, and wherein at least one of $R_{11}$ to $R_{16}$ represents fluorine,
wherein X is selected from the group consisting of a halogen, a hydroxy group, a thiol group, an imide group, a substituted or unsubstituted alkoxy group, a substituted or unsubstituted aryloxy group, a substituted or unsubstituted alkyl group, a substituted or unsubstituted alkylthio group, and a substituted or unsubstituted arylthio group,
wherein the second material transports a hole or an electron,
wherein the first material and the second material are formed as a bulk hetero mixed film having a microstructure in which one of the first material and the second material is in a crystal fine particle state or in an amorphous state.

22. The light detecting device according to claim 21, wherein the bulk hetero mixed film has a microstructure in which one of the first material and the second material is in a crystal fine particle state and the other of the first material or the second material is in an amorphous state or a crystal fine particle state.

23. The light detecting device according to claim 21, wherein the bulk hetero mixed film has a microstructure in which the first material is in a crystal fine particle state and the second material is in an amorphous state.

24. The light detecting device according to claim 21, wherein the bulk hetero mixed film has a microstructure in which the first material is in an amorphous state and the second material is in a crystal fine particle state.

25. The light detecting device according to claim 21, wherein each of $R_{11}$ to $R_{16}$ is fluorine.

26. The light detecting device according to claim 21, wherein at least one of $R_{11}$ and $R_{12}$ is fluorine, at least one of $R_{13}$ and $R_{14}$ is fluorine, and at least one of $R_{15}$ and $R_{16}$ is fluorine.

27. The light detecting device according to claim 21, wherein X is selected from the group consisting of a halogen, a hydroxy group, a substituted or unsubstituted alkoxy group, and a substituted or unsubstituted aryloxy group.

28. The light detecting according to claim 21, wherein the subphthalocyanine derivative is represented by one of the following formulas:

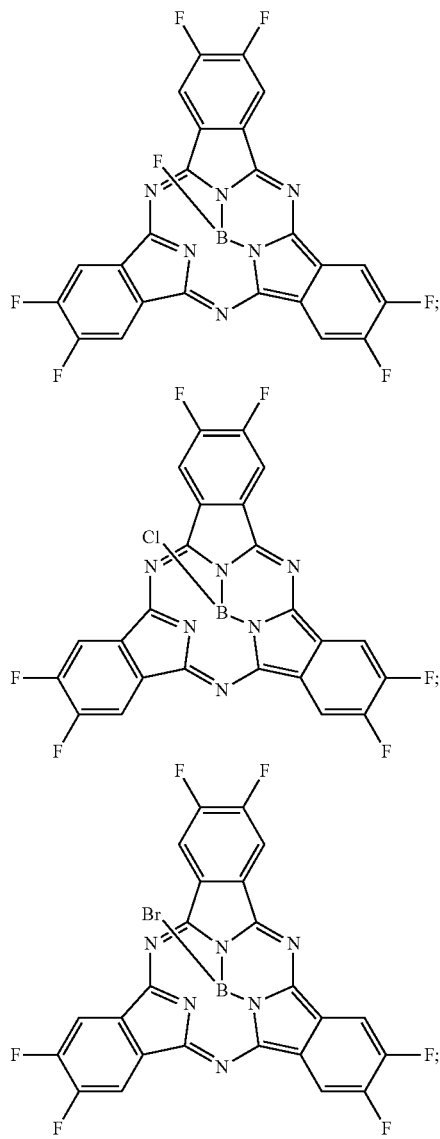

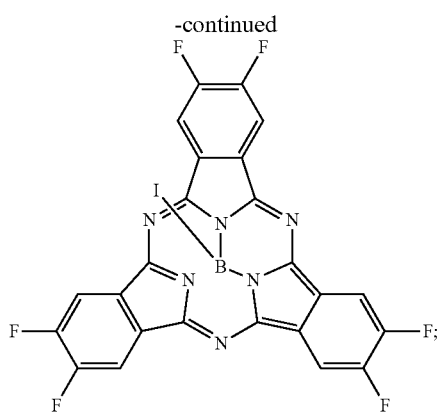
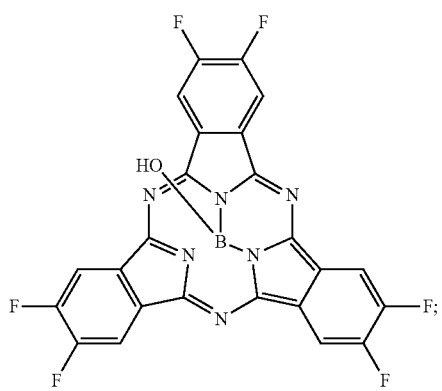
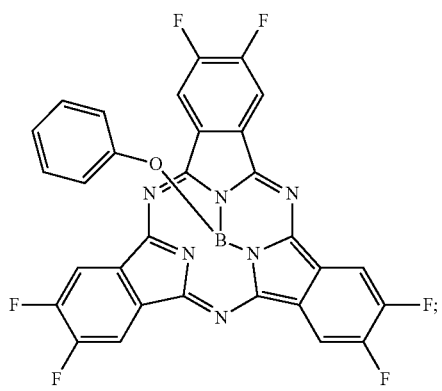
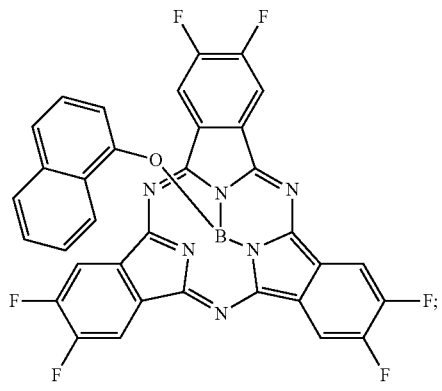
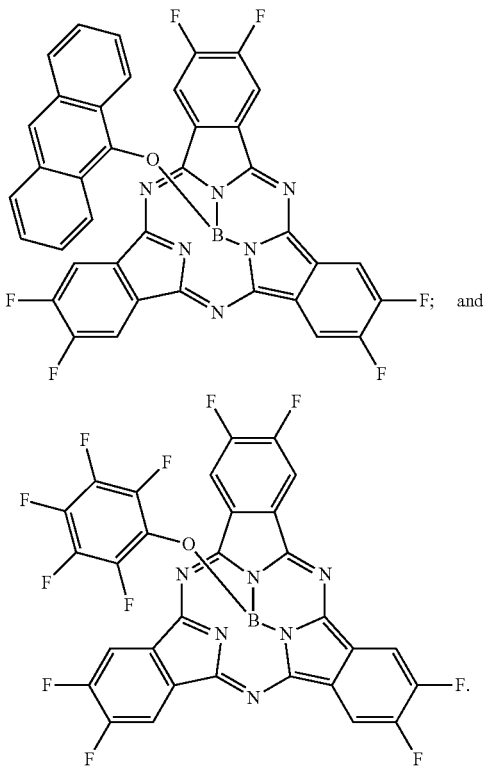
29. The light detecting device according to claim 21, wherein the subphthalocyanine derivative is represented by one of the following formulas:
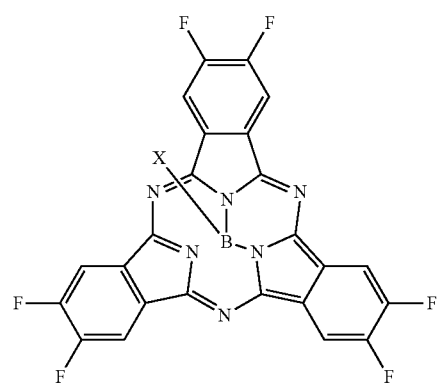
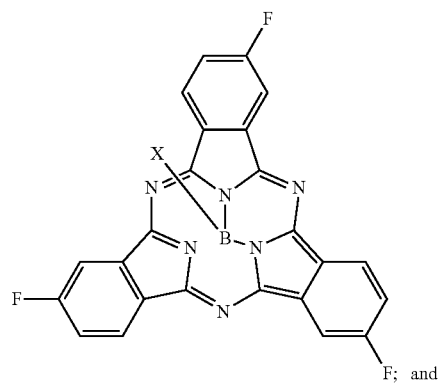

-continued

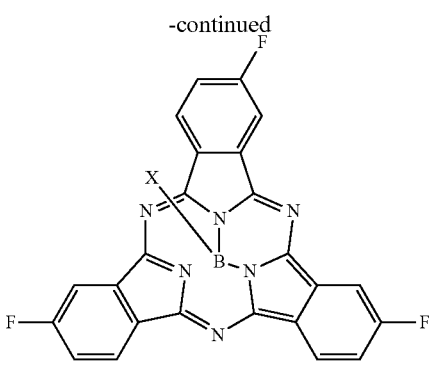

wherein X is selected from the group consisting of a halogen, a hydroxy group, a substituted or unsubstituted alkoxy group, and a substituted or unsubstituted aryloxy group.

30. The light detecting device according to claim 21, wherein the organic region further comprises a third material for blocking a hole introduced from the first electrode to the organic region and a fourth material for blocking an electron introduced from the second electrode to the organic region.

31. The light detecting device according to claim 30, wherein the bulk hetero mixed film is disposed between a hole blocking layer and an electron blocking layer, and wherein the hole blocking layer includes the third material and the electron blocking layer includes the fourth material.

32. The light detecting device according to claim 30, wherein the third material is an electron accepting material selected from the group consisting of fullerene, carbon nanotubes, oxadiazole, a triazole compound, anthraquinodimethane, diphenylquinone, distyrylarylene, and a silole compound.

33. The light detecting device according to claim 21, wherein the first material absorbs green light having a wavelength band of greater than or equal to approximately 450 nm and less than or equal to approximately 600 nm.

34. The light detecting device according to claim 21, further comprising;
a semiconductor substrate disposed below the organic region,
wherein the semiconductor substrate includes a first photodiode and a second photodiode disposed below the first photodiode, and
wherein the first photodiode absorbs blue light, the second photodiode absorbs red light, and the first photodiode and the second photodiode perform photoelectric conversion.

35. The light detecting device according to claim 21, further comprising a semiconductor substrate disposed below the organic region, wherein the semiconductor substrate includes a photoelectric conversion region.

36. The light detecting device according to claim 21, wherein the light detecting device is a solid-state image sensor.

37. A light detecting device, comprising:
a first electrode and a second electrode;
a photoelectric conversion film that selectively absorbs light of a specific wavelength and disposed between the first electrode and the second electrode;
wherein the photoelectric conversion film includes a first compound and a second compound, and the first compound and the second compound are formed as a bulk hetero mixed film,
wherein the first compound comprises a subphthalocyanine derivative having at least one fluorine group and a lowest unoccupied molecular orbital (LUMO) level of greater than or equal to −4.8 eV and less than or equal to −3.5 eV and a highest occupied molecular orbital (HOMO) level of greater than or equal to −7.0 eV and less than or equal to −5.5 eV,
wherein the second compound is configured to transport a hole or an electron,
and
wherein the photoelectric conversion film has a microstructure in which one of the first compound and the second compound is in a crystal fine particle state or in an amorphous state.

38. The light detecting device according to claim 37, wherein the photoelectric conversion film has microstructure in which one of the first compound and the second compound is in a crystal fine particle state and the other of the first compound or the second compound is in an amorphous state or a crystal fine particle state.

39. The light detecting device according to claim 37, wherein the first compound absorbs green light having a wavelength band of greater than or equal to approximately 450 nm and less than or equal to approximately 600 nm.

40. The light detecting device according to claim 37, wherein the lowest unoccupied molecular orbital (LUMO) level of the first compound is deeper than a LUMO level of the second compound, and a difference between the LUMO level of the first compound and the LUMO level of the second compound is greater than or equal to 0.1 eV and less than or equal to 1.0 eV.

41. The light detecting device according to claim 37, wherein the light detecting device is a solid-state image sensor.

* * * * *